US009523095B2

(12) United States Patent
Rönnow et al.

(10) Patent No.: US 9,523,095 B2
(45) Date of Patent: Dec. 20, 2016

(54) MICROORGANISM EXPRESSING XYLOSE ISOMERASE

(71) Applicant: TERRANOL A/S, Lyngby (DK)

(72) Inventors: Birgitte Rönnow, Copenhagen K (DK); Thomas Hvid Andersen, Frederiksberg (DK); Ole Sibbesen, Bagsärd (DK)

(73) Assignee: TERRANOL A/S, Lyngby (DK)

( * ) Notice: Subject to any disclaimer, the term of this patent is extended or adjusted under 35 U.S.C. 154(b) by 57 days.

(21) Appl. No.: 14/078,603

(22) Filed: Nov. 13, 2013

(65) Prior Publication Data

US 2014/0099720 A1    Apr. 10, 2014

Related U.S. Application Data

(62) Division of application No. 13/133,242, filed as application No. PCT/IB2009/055652 on Dec. 10, 2009, now abandoned.

(60) Provisional application No. 61/138,293, filed on Dec. 17, 2008.

(30) Foreign Application Priority Data

Dec. 16, 2008   (GB) .................................. 0822937.9

(51) Int. Cl.
| | | |
|---|---|---|
| C12N 9/92 | (2006.01) | |
| C12N 1/19 | (2006.01) | |
| C12N 15/81 | (2006.01) | |
| C12N 9/90 | (2006.01) | |
| C12P 7/06 | (2006.01) | |
| C12P 19/24 | (2006.01) | |

(52) U.S. Cl.
CPC ............... *C12N 15/81* (2013.01); *C12N 9/90* (2013.01); *C12N 9/92* (2013.01); *C12P 7/06* (2013.01); *C12P 19/24* (2013.01); *Y02E 50/17* (2013.01); *Y02P 20/52* (2015.11)

(58) Field of Classification Search
CPC ....................................................... C12N 9/90
See application file for complete search history.

(56) References Cited

FOREIGN PATENT DOCUMENTS

| | | |
|---|---|---|
| RU | 2283346 | 9/2006 |
| WO | WO 91/17243 | 11/1991 |
| WO | WO 03/062430 A1 | 7/2003 |
| WO | WO 2004/044129 A2 | 5/2004 |
| WO | WO 2004/099381 A2 | 11/2004 |
| WO | WO 2006/009434 A1 | 9/2006 |
| WO | WO 2006/096130 A1 | 9/2006 |
| WO | WO 2009/120731 A2 | 10/2009 |
| WO | WO 2010/000464 A1 | 1/2010 |
| WO | WO 2010/001363 A1 | 1/2010 |

OTHER PUBLICATIONS

Smith, P. K., et al., (1985) Measurement of protein using bicinchoninic acid. Anal. Biochem. 150, 76-85.
Tatusova, T. et al., Blast 2 Sequences, a new tool for comparing protein and nucleotide sequences, FEMS Microbiol Lett 1999 174(2): 247-250.
Tatusova, T. et al., Erratum to Blast 2 Sequences, a new tool comparing protein and nucleotide sequences, FEMS Microbiol Lett 1999 177(1): 187-188.
Trueman, L.T. et al., Heterlogous Expression in Yeast, Methods Molecular Biology (1995), vol. 49, p. 341-354.
Van Maris, Antonius J.A. et al., "Development of Efficient Xylose Fermentation in *Saccharomyces cerevisiae*: Xylose Isomerase as a Key Component", Adv. Biochem Engin/Biotechnol. (2007) 108: 179-204.
Verho, R., et al., (2004) A Novel NADH-linked L-Xylulose Reductase in the L-Arabinose Catabolic Pathway of Yeast. J. Biol. Chem. 279, 14746-14751.
*Walfridsson, M., et al., (1996) Ethanolic Fermentation of Xylose with *Saccharomyces cerevisiae* Harboring the Thermus thermophilus xylA Gene, Which Expresses an Active Xylose (Glucose) Isomerase. Appl. Environ. Microbiol. 62, 4648-4651.
Wang, P. Y., et al., (1980) Growth of yeasts on D-xylulose. Can. J. Microbiol. 26, 1165-1168.
Witteveen, C. F. B., et al., (1994) Isolation and characterisation of two xylitol dehydrogenases from Aspergillus niger. Microbiol. 140, 1679-1685.
Woodyer, R. et al., (2005) Heterologous Expression, Purification, and Characterization of a Highly Active Xylose Reductase from Neurospora crassa. Appl. Environ. Microbiol. 71, 1642-1647.
Yanase, Hideshi et al., "Genetic Engineering of Zymobacter palmae for Production of Ethanol from Xylose" Applied and Environmental Microbiology, vol. 73, No. 8, Apr. 2007, pp. 2592-2599.
Brat D. et al., "Functional Expression of a Bacterial Xylose Isomerase in *Saccharomyces cerevisiae*", Applied and Environmental Microbiology, 75(8), p. 2304-2111. Dec. 31, 2009.
Chiang L-C et al., "D-Xylulose Fermentation to Ethanol by *Saccharomyces cerevisiae*", Applied and Environmental Microbiology, vol. 42, No. 2, p. 284-289. Aug. 31, 1981.
Queen Mary University of London, "IUBMB Enzyme Nomenclature: EC 1.1.1.10," http://www.chem.qmul.ac.uk/iubmb/enzyme/EC1/1/1/10.html, retrieved from the Internet on Oct. 19, 2011.
Queen Mary University of London, "IUBMB Enzyme Nomenclature: EC 1.1.1.11," http://www.chem.qmul.ac.uk/iubmb/enzyme/EC1/1/1/11.html, retrieved from the Internet on Oct. 19, 2011.
Queen Mary University of London, "IUBMB Enzyme Nomenclature: EC 1.1.1.12," http://www.chem.qmul.ac.uk/iubmb/enzyme/EC1/1/1/12.html, retrieved from the Internet on Oct. 19, 2011.

(Continued)

*Primary Examiner* — Rebecca Prouty
(74) *Attorney, Agent, or Firm* — McKee, Voorhees & Sease, PLC

(57) ABSTRACT

The present invention relates to a transformed microorganism capable of (a) a higher xylose isomerase activity than the equivalent microorganism prior to transformation; and/or (b) a higher growth rate in or on a growth medium comprising xylose than the equivalent microorganism prior to transformation; and/or (c) a faster metabolism of xylose than the equivalent microorganism prior to transformation; and/or (d) a higher production of ethanol when grown anaerobically on xylose as the carbon source than the equivalent microorganism prior to transformation.

8 Claims, 7 Drawing Sheets

(56) References Cited

OTHER PUBLICATIONS

Figure 1:
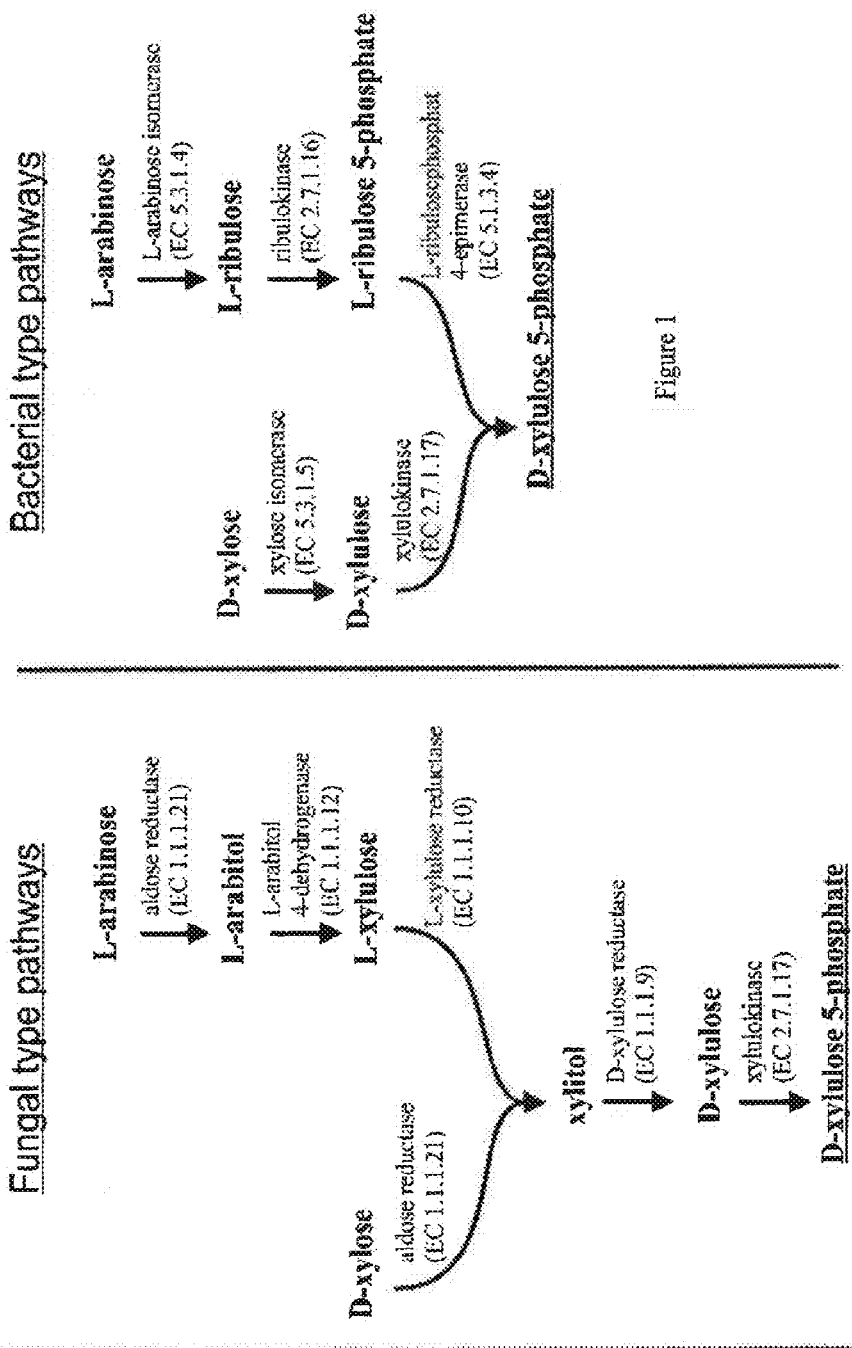

Queen Mary University of London, "IUBMB Enzyme Nomenclature: EC 1.1.1.21," http://www.chem.qmul.ac.uk/iubmb/enzyme/EC1/1/1/21.html, retrieved from the Internet on Oct. 19, 2011.
Queen Mary University of London, "IUBMB Enzyme Nomenclature: EC 1.1.1.56," http://www.chem.qmul.ac.uk/iubmb/enzyme/EC1/1/1/56.html, retrieved from the Internet on Oct. 19, 2011.
Queen Mary University of London, "IUBMB Enzyme Nomenclature: EC 1.1.1.9," http://www.chem.qmul.ac.uk/iubmb/enzyme/EC1/1/1/9.html, retrieved from the Internet on Oct. 19, 2011.
Queen Mary University of London, "IUBMB Enzyme Nomenclature: EC 2.2.1.1," http://www.chem.qmul.ac.uk/iubmb/enzyme/EC2/2/1/1.html, retrieved from the Internet on Oct. 19, 2011.
Queen Mary University of London, "IUBMB Enzyme Nomenclature: EC 2.2.1.2," http://www.chem.qmul.ac.uk/iubmb/enzyme/EC2/2/1/2.html, retrieved from the Internet on Oct. 19, 2011.
Queen Mary University of London, "IUBMB Enzyme Nomenclature: EC 2.7.1.16," http://www.chem.qmul.ac.uk/iubmb/enzyme/EC2/7/1/16.html, retrieved from the Internet on Oct. 19, 2011.
Queen Mary University of London, "IUBMB Enzyme Nomenclature: EC 2.7.1.17," http://www.chem.qmul.ac.uk/iubmb/enzyme/EC2/7/1/17.html, retrieved from the Internet on Oct. 19, 2011.
Queen Mary University of London, "IUBMB Enzyme Nomenclature: EC 2.7.1.47," http://www.chem.qmul.ac.uk/iubmb/enzyme/EC2/7/1/47.html, retrieved from the Internet on Oct. 19, 2011.
Queen Mary University of London, "IUBMB Enzyme Nomenclature: EC 5.1.3.1," http://www.chem.qmul.ac.uk/iubmb/enzyme/EC5/1/3/1.html, retrieved from the Internet on Oct. 19, 2011.
Queen Mary University of London, "IUBMB Enzyme Nomenclature: EC 5.1.3.3," http://www.chem.qmul.ac.uk/iubmb/enzyme/EC5/1/3/3.html, retrieved from the Internet on Oct. 19, 2011.
Queen Mary University of London, "IUBMB Enzyme Nomenclature: EC 5.1.3.4," http://www.chem.qmul.ac.uk/iubmb/enzyme/EC5/1/3/4.html, retrieved from the Internet on Oct. 19, 2011.
Queen Mary University of London, "IUBMB Enzyme Nomenclature: EC 5.3.1.15," http://www.chem.qmul.ac.uk/iubmb/enzyme/EC5/3/1/15.html, retrieved from the Internet on Oct. 19, 2011.
Queen Mary University of London, "IUBMB Enzyme Nomenclature: EC 5.3.1.20," http://www.chem.qmul.ac.uk/iubmb/enzyme/EC5/3/1/20.html, retrieved from the Internet on Oct. 19, 2011.
Queen Mary University of London, "IUBMB Enzyme Nomenclature: EC 5.3.1.4," http://www.chem.qmul.ac.uk/iubmb/enzyme/EC5/3/1/4.html, retrieved from the Internet on Oct. 19, 2011.
Queen Mary University of London, IUBMB Enzyme Nomenclature: EC 5.3.1.5, http://www.chem.qmul.ac.uk/iubmb/enzyme/EC5/3/1/5.html, retrieved from the Internet on Oct. 19, 2011.
Queen Mary University of London, IUBMB Enzyme Nomenclature: EC 5.3.1.6, http://www.chem.qmul.ac.uk/iubmb/enzyme/EC5/3/1/6.html, retrieved from the Internet on Oct. 19, 2011.
Jin Y-S et al., "Optimal Growth and Ethanol Production from Xylose by Recombinant *Saccharomyces cerevisiae* Require Moderate D-Xylulokinase Activity", Applied Environmental Microbiology, vol. 69, No. 1, p. 495-503. Jan. 31, 2003.
Krynetski E Y et al., "A single point mutation leading to loss of catalytic activity in human thiopuine S-methyltransferase", Proc Natl Acad Sci USA, Medical Sciences, vol. 92, p. 949-953. Feb. 28, 1995.
Liu X et al., "Fermentation of xylose to produce ethanol by recombinant *Saccharomyces cerevisiae* strain containing XYLA and XKS1", Chinese Science Bulletin, vol. 50, No. 7, p. 652-657. Dec. 31, 2005.
Madhaven A et al., "Xylose isomerase from polycentric fungus Orpinomyces: gene sequencing, cloning, and expression in *Saccharomycese cerevisiae* for bioconversion of xylose to ethanol", Applied Microbiol. Biotechnol., 82(6), p. 1067-78. Apr. 30, 2009.
Matsushika A et al., "Efficient Bioethanol Production from Xylose by Recombinant *Saccharomyces cerevisiae* Required High Activity of Xylose Reductase and Moderate Xylulokinase Activity", Journal of Bioscience and Bioengineering, vol. 16, No. 3, p. 306-309. Dec. 31, 2008.

Newcomb R D et al., "A single amino acid substitution converts a caroxylesterase to an organophosphorus hydrolase and confers insecticide resistance on a blowfly", Proc Natl Acad Sci USA, Genetics, vol. 94, p. 7464-7468. Jul. 31, 1997.
Pakula A A et al., "Genetic Analysis of protein stability and function", Annu. Rev. Genet., 23, p. 289-310. Dec. 31, 1989.
Porter T D et al., "Cytochrome P-450. Multiplicity of isoforms, substrates, and catalytic and regulatory mechanisms", The Journal of Biological Chemistry, vol. 266, No. 21, p. 12469-12472. Jul. 25, 1991.
Rodriguez-Penet J M et al., "The YGR194c (XKS1) gene encodes the xylulokinase from the budding yeast *Saccharomyces cerevisiae*", FEMS Microbiology Letters, 162, p. 155-160. Dec. 31, 1998.
Spencer JFT et al. (ed), "Yeast Genetics Fundamental and Applied Aspects", Springer Verlag, p. 468-469, ISBN 0-540-90793-9. Dec. 31, 1983.
RU 2283346, Nikolaevich et al.—English Translation. Sep. 10, 2006.
Amore, et al., "The fermentation of xylose—an analysis of the expression of Bacillus and Actinoplanes xylose isomerase genes in yeast", Appl Microbiol Biotechnol, 30, pp. 351-357. Dec. 31, 1989.
Briggs, et al., "Molecular cloning, DNA structure and expression of the *Escherichia coli* D-xylose isomerase", The EMBO Journal, vol. 3, No. 3, pp. 611-616. Dec. 31, 1984.
Gardonyi, et al., "The *Streptomyces rubiginosus* xylose isomerase is misfolded when expressed in *Saccharomyces cerevisiae*", Enzyme and Microbial Technology, 32, pp. 252-259. Dec. 31, 2003.
Ho, et al., "Purification and characterization of the D-xylose isomerase gene from *Escherichia coli*", Enzyme Microb. Technol., vol. 5, pp. 417-420. Jun. 3, 1983.
Jin, et al., "Xylitol production by a Pichia stipitis D-xylulokinase mutant", Appl Microbiol Biotechnol, 68, pp. 42-45. Dec. 31, 2005.
Park, et al., "Restoration of a Defective Lactococcus lactis Xylose Isomerase", Applied and Environmental Microbiology, vol. 70, No. 7, pp. 4318-4325. Jul. 31, 2004.
Sarthy, et al., "Expression of the *Escherichia coli* Xylose Isomerase Gene in *Saccharomyces cerevisiae*", Applied and Environmental Microbiology, vol. 53, No. 9, pp. 1996-2000. Sep. 30, 1987.
Toivari, et al., "Conversion of Xylose to Ethanol by Recombinant *Saccharomyces cerevisiae*: Importance of Xylulokinase (XKS1) and Oxygen Availability", Metabolic Engineering, 3, pp. 236-249. Dec. 31, 2001.
Traff, et al., "Deletion of the GRE3 Aldose Reductase Gene and Its Influence on Xylose Metabolism in Recombinant Strains of *Saccharomyces cerevisiae* Expressing the xylA and XKS1 Genes", Appl and Environ Microb, vol. 67, No. 12, pp. 5668-5674. Dec. 31, 2001.
Wang, et al., "Fermentation of a Pentose by Yeasts", Biochemical and Biophysical Research Communications, vol. 94, No. 1, pp. 248-254. May 14, 1980.
Wang, et al., "Fermentation of D-Xylose by Yeasts Using Glucose Isomerase", Biotechnology Letters, vol. 2, No. 6, pp. 273-278. Dec. 31, 1980.
UniProtBK/Swiss-Protdatabase P22842 (XYLA_THEP3), (D5) Aug. 1, 1991.
UniProtBK/Swiss-Protdatabase P22842 (XYLA_THEP3), (D5) Nov. 13, 2013.
UniProtKB/Swiss-Prot database Q9CFG7 (XYLA_LACLA), (D4) Jun. 1, 2001.
UniProtKB/Swiss-Prot database Q9CFG7 (XYLA_LACLA), (D4) Nov. 13, 2013.
Altschul SF et al., Basic Local Alignment Search Tool., J. Mol. Biol., 1990, vol. 215, p. 403-410.
Anderson, R. L. et al., (1965) Purification and Characterization of D-Lyxose Isomerase. J. Biol. Chem. 240, 2367-2372.
Ausubel et al., 1999 Short Protocols in Molecular Biology, 4th Ed—Chapter 18.
Ausubel et al., 1999, Short Protocols in Molecular Biology, pp. 7-58 to 7-6.
Bao X. et al. (1999) Expression of xylose isomerase gene (xyIA) in *Saccharomyces cerevisiae* from Clostridium thermohydrosulphuricum. Wei Sheng Wu Xue Bao 39, 49-54.

(56) References Cited

OTHER PUBLICATIONS

Becker D. M. et al., (1991) High-efficiency transformation of yeast by electroporation. Methods Enzymol. 194, 182-187.
Beggs, J.D., Transformation of yeast by a replicating hybrid plasmid, Nature, 1978, vol. 275, p. 104-109.
Cereghino, J.L. et al., Heterologous protein expression in the methylotrophic yeast Pichia pastoris, FEMS Microbiology Reviews, 2000, 24(1):45-66.
Cheng, H., et al., (2005) Molecular cloning and functional expression of D-arabitol dehydrogenase gene from Gluconobacter oxydans in *Escherichia coli*. FEMS Microbiol. Lett. 252, 35-42.
Devereux J. et al., A comprehensive set of sequence analysis programs for the VAX, Nucleic Acids Research, 1984, vol. 12, No. 1. p. 387-395.
Dische Z. et al., (1951) A new spectrophotometric method for the detection and determination of keto sugars and trioses. J. Biol. Chem. 192, 583.
Dothie, J. M., Giglio J. R., Moore C. B., Taylor S. S., and Hartley B. S. (1985) Ribitol dehydrogenase of Klebsiella aerogenes. Sequence and properties of wild-type and mutant strains. Biochem. J. 230, 569-578.
Eberts, T.J. et al., A Simplified, Colorimetric Micromethod for Xylose in Serum or Urine, with Phloroglucinol, 1979, Clin. Chem. 25, No. 8, pp. 1440-1443.
Erlandson, Karn A. et al., "Dissolution of Xylose Metabolism in Lactococcus lactis", Applied and Environmental Microbiology, vol. 66, No. 9, Sep. 2000, pp. 3974-3980.
GenBank accession No. AAD20249 (Sep. 12, 2000).
GenBank accession No. ABX75758 (May 3, 2010).
GenBank accession code AF092042 (Sep. 12, 2000).
GenBank accession code D00756 (Dec. 15, 2007).
GenBank accession code J05650 (Apr. 26, 1993).
GenBank accession No. AAD20245 (Sep. 12, 2000).
GenBank accession No. AAD20251 (Sep. 12, 2000).
GenBank accession No. AAD20257 (Sep. 12, 2000).
GenBank accession No. AAK05605 (Feb. 26, 2009).
GenBank accession No. AAO80762 (Mar. 5, 2010).
GenBank accession No. ABI49935 (Feb. 7, 2011).
GenBank accession No. ABJ73095 (Jan. 13, 2011).
GenBank accession No. ABX75760 (May 3, 2010).
GenBank accession No. AF127802 (Jun. 21, 2007).
GenBank accession No. X61377 (May 22, 2001).
Higgins, D.G. et al., Clustal: a package for performing multiple sequence alignment on a microcomputer, Gene, 1988, vol. 73, No. 1, p. 237-244.
Hinnen, A. et al., Transformation of yeast, Proceedings of the National Academy of Sciences of the USA, 1978, vol. 75, p. 1929-1933.
Hollenberg, C.P. et al., Production of recombinant proteins by methyltrophic yeasts, Current Opinion Biotechnology, Oct. 1997;8(5):554-60.
Horwell, D.C., The 'peptoid' approach to the design of non-peptide, small molecule agonists and antagonists of neuropeptides', Trends Biotechnol. (1995) 13(4), 132-134.
Ito, H. et al., Transformation of Intact Yeast Cells Treated with Alkali Cations, Journal of Bacteriology, 1983, vol. 153, No. 1, p. 163-168.

Izumori, K.,et al. (1975) Purification,Crystallization, and Properties of D-Ribose Isomerase from *Mycobacterium smegmatis*. J. Biol. Chem. 250, 8085-8087.
Richard, P., et al., (2001) Cloning and Expression of a Fungal L-Arabinitol 4-Dehydrogenase Gene. J. Biol. Chem. 276, 40631-40637.
Simon, R.J., et al., Peptoids: A modular approach to drug discovery, Proc. Natl. Acad. Sci. USA, (1992) 89(20), 9367-9371.
Shimonishi, T., et al., (1996) A new enzyme, L-ribose isomerase from *Acinetobacter* sp. strain DL-28. J. Ferment. Bioeng. 81, 493-497.
Ueng et al. "D-Xylulose Fermentation in Yeasts," Biotechnology Letters vol. 3, No. 6, 315-320 (1981).
Kavanagh K., et al., (2003) Structure of xylose reductase bound to NAD+ and the basis for single and dual co-substrate specificity in family 2 aldo-keto reductases. Biochem. J. 373, 319-326.
Kuyper, M. et al., (2003) High-level functional expression of a fungal xylose isomerase: the key to efficient ethanolic fermentation of xylose by *Saccharomyces cerevisiae*. FEMS Yeast Research 4, 69-78.
Kuyper, Marko et al., "Metabolic engineering of xylose-isomerase-expressing *Saccharomyces cerevisiae* strain for rapid anaerobic xylose fermentation" FEMS Yeast Research, 5 (2005), pp. 399-409.
Kuyper, M. et al., "Minimal metabolic engineering of *Saccharomyces verevisiae* for efficient anaerobic xylose fermentation: a proof of principle", FEMS Yeast Research, 2004, vol. 4, p. 655-664.
Lee C., et al., (1989) Catalytic Mechanism of Xylose (Glucose) Isomerase from Clostridium thermosulfurogenes. Characterization of the structural gene and function of active site histidine. J. Biol. Chem. 265, 19082-19090.
Lee C., et al., (1993) Taxonomic distinction of saccharolytic thermophilic anaerobes: description of *Thermoanaerobacterium xylanolyticum* gen. nov., sp. nov., and *Thermoanaerobacterium saccharolyticum* gen. nov., sp. nov.; reclassification of *Thermoanaerobium brockii, Clostridium thermosulfurogenes*, and *Clostridium thermohydrosulfuricum* E100-69 as *Thermoanaerobacter brockii* comb. nov., *Thermoanaerobacterium thermosulfurigenes* comb. nov., and *Thermoanaerobacter thermohydrosulfuricus* comb.nov., respectively; and transfer of Clostridium thermohydrosulfuricum 39E to Thermoanaerobacter ethanolicus. International Journal of Systemic Bacteriology 43:41-51 (1993).
Lonn, A., et al., (2002) Cold adaptation of xylose isomerase from Thermus thermophilus through random PCR mutagenesis. Eur. J. Biochem. 269, 157-163.
Meng, M., et al., (1993) The role of active-site aromatic and polar residues in catalysis and substrate discrimination by xylose isomerase. Proc. Natl. Acad. Sci. USA 90, 8459-8463.
Mumberg, D., et al., (1995) Yeast vectors for the controlled expression of heterologous proteins in different genetic backgrounds. Gene 156, 119-122.
Nakamura, Y. et al., (2000) Codon Usage tabulated from international DNA sequence databases: status for the year 2000. Nucleic Acids Res. 28, 292.
Park, J. H. et al., "Restoration of a Defective Lactococcus lactis Xylose Isomerase", Applied Environ, Microbiol. 70(7):4318-4325 (2004).

SEQUENCE LISTING

<160> NUMBER OF SEQ ID NOS: 28

<210> SEQ ID NO 1
<211> LENGTH: 1320
<212> TYPE: DNA
<213> ORGANISM: Lactococcus lactis subsp. lactis
<220> FEATURE:
<221> NAME/KEY: CDS
<222> LOCATION: (1)..(1320)

<400> SEQUENCE: 1

```
atg gct tac ttt aac gac atc gca cct atc aaa tac gaa ggt aca aaa         48
Met Ala Tyr Phe Asn Asp Ile Ala Pro Ile Lys Tyr Glu Gly Thr Lys
1               5                   10                  15 act aaa aat atg ttt gcc ttt cgc cat tat aat cca gaa gaa gta gtt         96
Thr Lys Asn Met Phe Ala Phe Arg His Tyr Asn Pro Glu Glu Val Val
                20                  25                  30 gct ggt aaa aca atg gaa gaa caa ctt cat ttt gcc ctt gca ttt tgg        144
Ala Gly Lys Thr Met Glu Glu Gln Leu His Phe Ala Leu Ala Phe Trp
            35                  40                  45 cat aca att aca atg gat ggg tca gat ccc ttt ggg gga gca aca atg        192
His Thr Ile Thr Met Asp Gly Ser Asp Pro Phe Gly Gly Ala Thr Met
        50                  55                  60 gaa cgc cct tgg gat ttg gaa ggt ggt tct gaa ctt gac cgt gct cac        240
Glu Arg Pro Trp Asp Leu Glu Gly Gly Ser Glu Leu Asp Arg Ala His
65                  70                  75                  80 cgt cga gta gat gct ttc ttt gaa att gct gaa aaa tta ggt gtt aaa        288
Arg Arg Val Asp Ala Phe Phe Glu Ile Ala Glu Lys Leu Gly Val Lys
                85                  90                  95 tat tat tgt ttc cat gat att gat att gca cct act gga aat tct ttg        336
Tyr Tyr Cys Phe His Asp Ile Asp Ile Ala Pro Thr Gly Asn Ser Leu
                100                 105                 110 aaa gaa ttt tat gct aat ttg gac gaa att act gac cac ctt ctt gaa        384
Lys Glu Phe Tyr Ala Asn Leu Asp Glu Ile Thr Asp His Leu Leu Glu
            115                 120                 125 aaa caa aaa gca aca ggg att aaa tta ctt tgg aat aca gca aac atg        432
Lys Gln Lys Ala Thr Gly Ile Lys Leu Leu Trp Asn Thr Ala Asn Met
        130                 135                 140 ttt tca aat ccc cgc tat atg aat ggt gtt tca act tct aat cgt gct        480
Phe Ser Asn Pro Arg Tyr Met Asn Gly Val Ser Thr Ser Asn Arg Ala
145                 150                 155                 160 gaa gtc ttt gct tat ggt gct gca caa gtt aaa aaa ggt ctt gaa ctt        528
```

| | | | | | | | | | | | | |
|---|---|---|---|---|---|---|---|---|---|---|---|---|
| Glu | Val | Phe | Ala | Tyr 165 | Gly | Ala | Ala | Gln | Val 170 | Lys | Lys | Gly | Leu | Glu 175 | Leu |

| | | | | | | | | | | | | | |
|---|---|---|---|---|---|---|---|---|---|---|---|---|---|
| tct | aaa | aaa | ctc | ggt | ggt | gaa | aat | tac | gtc | ttc | tgg | ggt | ggt | cgt | gaa | | 576 |
| Ser | Lys | Lys | Leu | Gly | Gly | Glu | Asn | Tyr | Val | Phe | Trp | Gly | Gly | Arg | Glu | | |
| | | | 180 | | | | | 185 | | | | | 190 | | | | |

| ggt | tat | gaa | tca | ctt | ttg | aat | aca | gat | atg | ggt | ctt | gaa | atg | gat | cat | | 624 |
|---|---|---|---|---|---|---|---|---|---|---|---|---|---|---|---|---|---|
| Gly | Tyr | Glu | Ser | Leu | Leu | Asn | Thr | Asp | Met | Gly | Leu | Glu | Met | Asp | His | | |
| | | | 195 | | | | | 200 | | | | | 205 | | | | |

| atg | gca | aaa | ttc | ttc | cat | ttg | gca | att | gat | tat | gca | aaa | tca | atc | aac | | 672 |
|---|---|---|---|---|---|---|---|---|---|---|---|---|---|---|---|---|---|
| Met | Ala | Lys | Phe | Phe | His | Leu | Ala | Ile | Asp | Tyr | Ala | Lys | Ser | Ile | Asn | | |
| 210 | | | | | 215 | | | | | 220 | | | | | | | |

| cac | ttg | ccc | att | ttc | ttg | att | gaa | cca | aaa | cca | aaa | gaa | cca | atg | act | | 720 |
|---|---|---|---|---|---|---|---|---|---|---|---|---|---|---|---|---|---|
| His | Leu | Pro | Ile | Phe | Leu | Ile | Glu | Pro | Lys | Pro | Lys | Glu | Pro | Met | Thr | | |
| 225 | | | | | 230 | | | | | 235 | | | | | 240 | | |

| cac | caa | tat | gat | ttt | gac | tca | gca | aca | gct | ctt | gct | ttc | ttg | caa | aaa | | 768 |
|---|---|---|---|---|---|---|---|---|---|---|---|---|---|---|---|---|---|
| His | Gln | Tyr | Asp | Phe | Asp | Ser | Ala | Thr | Ala | Leu | Ala | Phe | Leu | Gln | Lys | | |
| | | | | 245 | | | | | 250 | | | | | 255 | | | |

| tat | gat | ttg | gac | aaa | tat | ttc | aaa | ctc | aat | ctt | gaa | aca | aat | cat | gct | | 816 |
|---|---|---|---|---|---|---|---|---|---|---|---|---|---|---|---|---|---|
| Tyr | Asp | Leu | Asp | Lys | Tyr | Phe | Lys | Leu | Asn | Leu | Glu | Thr | Asn | His | Ala | | |
| | | | 260 | | | | | 265 | | | | | 270 | | | | |

| tgg | ttg | gct | gga | cac | act | ttt | gaa | cac | gaa | tta | aat | act | gct | cgt | act | | 864 |
|---|---|---|---|---|---|---|---|---|---|---|---|---|---|---|---|---|---|
| Trp | Leu | Ala | Gly | His | Thr | Phe | Glu | His | Glu | Leu | Asn | Thr | Ala | Arg | Thr | | |
| | | 275 | | | | | 280 | | | | | 285 | | | | | |

| ttc | aat | gct | ttg | ggt | tct | att | gat | gcc | aat | caa | gga | aat | tac | ttg | ctt | | 912 |
|---|---|---|---|---|---|---|---|---|---|---|---|---|---|---|---|---|---|
| Phe | Asn | Ala | Leu | Gly | Ser | Ile | Asp | Ala | Asn | Gln | Gly | Asn | Tyr | Leu | Leu | | |
| | 290 | | | | | 295 | | | | | 300 | | | | | | |

| ggt | tgg | gat | aca | gat | gaa | ttc | cca | aca | ctt | gtt | att | gat | atc | aca | ctt | | 960 |
|---|---|---|---|---|---|---|---|---|---|---|---|---|---|---|---|---|---|
| Gly | Trp | Asp | Thr | Asp | Glu | Phe | Pro | Thr | Leu | Val | Ile | Asp | Ile | Thr | Leu | | |
| 305 | | | | | 310 | | | | | 315 | | | | | 320 | | |

| gcg | atg | cac | caa | att | ctt | ttg | aac | ggt | gga | ctt | ggc | aaa | ggt | gga | att | | 1008 |
|---|---|---|---|---|---|---|---|---|---|---|---|---|---|---|---|---|---|
| Ala | Met | His | Gln | Ile | Leu | Leu | Asn | Gly | Gly | Leu | Gly | Lys | Gly | Gly | Ile | | |
| | | | | 325 | | | | | 330 | | | | | 335 | | | |

| aac | ttt | gat | gcg | aaa | gta | cgt | cgt | aca | agt | ttc | aaa | gca | gaa | gat | tta | | 1056 |
|---|---|---|---|---|---|---|---|---|---|---|---|---|---|---|---|---|---|
| Asn | Phe | Asp | Ala | Lys | Val | Arg | Arg | Thr | Ser | Phe | Lys | Ala | Glu | Asp | Leu | | |
| | | | 340 | | | | | 345 | | | | | 350 | | | | |

| att | ctt | gct | cat | att | gca | ggg | atg | gat | act | tat | gcg | cgt | gct | ttg | aaa | | 1104 |
|---|---|---|---|---|---|---|---|---|---|---|---|---|---|---|---|---|---|
| Ile | Leu | Ala | His | Ile | Ala | Gly | Met | Asp | Thr | Tyr | Ala | Arg | Ala | Leu | Lys | | |
| | | 355 | | | | | 360 | | | | | 365 | | | | | |

| ggt | gca | gca | gca | atc | att | gaa | gat | aaa | ttc | ttg | tct | gat | att | gtt | gac | | 1152 |
|---|---|---|---|---|---|---|---|---|---|---|---|---|---|---|---|---|---|
| Gly | Ala | Ala | Ala | Ile | Ile | Glu | Asp | Lys | Phe | Leu | Ser | Asp | Ile | Val | Asp | | |
| | 370 | | | | | 375 | | | | | 380 | | | | | | |

| gaa | cgt | tat | agt | tca | tac | aaa | aat | aca | gaa | gtt | ggt | caa | tcc | att | gaa | | 1200 |
|---|---|---|---|---|---|---|---|---|---|---|---|---|---|---|---|---|---|
| Glu | Arg | Tyr | Ser | Ser | Tyr | Lys | Asn | Thr | Glu | Val | Gly | Gln | Ser | Ile | Glu | | |
| 385 | | | | | 390 | | | | | 395 | | | | | 400 | | |

| aat | gga | aca | gca | act | ttt | gaa | agt | ctt | gcc | gca | ttt | gca | ctt | gaa | tat | | 1248 |
|---|---|---|---|---|---|---|---|---|---|---|---|---|---|---|---|---|---|
| Asn | Gly | Thr | Ala | Thr | Phe | Glu | Ser | Leu | Ala | Ala | Phe | Ala | Leu | Glu | Tyr | | |
| | | | | 405 | | | | | 410 | | | | | 415 | | | |

| ggt | gat | gat | att | gaa | ctt | gat | tct | aat | cac | ttg | gaa | tac | atc | aaa | tca | | 1296 |
|---|---|---|---|---|---|---|---|---|---|---|---|---|---|---|---|---|---|
| Gly | Asp | Asp | Ile | Glu | Leu | Asp | Ser | Asn | His | Leu | Glu | Tyr | Ile | Lys | Ser | | |
| | | | 420 | | | | | 425 | | | | | 430 | | | | |

| gta | ttg | aat | gac | tat | ctt | gtt | taa | | | | | | | | | | 1320 |
|---|---|---|---|---|---|---|---|---|---|---|---|---|---|---|---|---|---|
| Val | Leu | Asn | Asp | Tyr | Leu | Val | | | | | | | | | | | |
| | | 435 | | | | | | | | | | | | | | | |

<210> SEQ ID NO 2
<211> LENGTH: 37
<212> TYPE: DNA
<213> ORGANISM: Artificial Sequence
<220> FEATURE:
<223> OTHER INFORMATION: Primer

```
<400> SEQUENCE: 2
gctagccatg gcttacttta acgacatcgc acctatc                              37

<210> SEQ ID NO 3
<211> LENGTH: 43
<212> TYPE: DNA
<213> ORGANISM: Artificial Sequence
<220> FEATURE:
<223> OTHER INFORMATION: Primer

<400> SEQUENCE: 3
ctcgagccta ggctaaacaa gatagtcatt caatactgat ttg                       43

<210> SEQ ID NO 4
<211> LENGTH: 40
<212> TYPE: DNA
<213> ORGANISM: Artificial Sequence
<220> FEATURE:
<223> OTHER INFORMATION: Primer

<400> SEQUENCE: 4
gctagccatg gccactaccc catttgatgc tccagataag                           40

<210> SEQ ID NO 5
<211> LENGTH: 43
<212> TYPE: DNA
<213> ORGANISM: Artificial Sequence
<220> FEATURE:
<223> OTHER INFORMATION: Primer

<400> SEQUENCE: 5
ctcgagccta ggctagtgtt tcaattcact ttccatcttg gcc                       43

<210> SEQ ID NO 6
<211> LENGTH: 1383
<212> TYPE: DNA
<213> ORGANISM: Artificial Sequence
<220> FEATURE:
<223> OTHER INFORMATION: Artificial Thermoanaerobacter
      thermohydrosulfuricus xylose isomerase gene
<220> FEATURE:
<221> NAME/KEY: CDS
<222> LOCATION: (49)..(1365)

<400> SEQUENCE: 6
```

| | | | | | | | | | |
|---|---|---|---|---|---|---|---|---|---|
| gaattcctag aaataatttt gtttaacttt aagaaggagg agctagcc atg gaa tat | | | | | | | | | 57 |
| | | | | | | | Met Glu Tyr | | |
| | | | | | | | 1 | | |

| ttc | aaa | aac | gtg | cca | cag | atc | aag | tat | gaa | ggt | cct | aaa | agc | aat | aac | 105 |
|---|---|---|---|---|---|---|---|---|---|---|---|---|---|---|---|---|
| Phe | Lys | Asn | Val | Pro | Gln | Ile | Lys | Tyr | Glu | Gly | Pro | Lys | Ser | Asn | Asn | |
| 5 | | | | 10 | | | | | 15 | | | | | | | |

| cct | tat | gca | ttt | aag | ttc | tat | aac | cca | gat | gaa | att | ata | gat | gga | aaa | 153 |
|---|---|---|---|---|---|---|---|---|---|---|---|---|---|---|---|---|
| Pro | Tyr | Ala | Phe | Lys | Phe | Tyr | Asn | Pro | Asp | Glu | Ile | Ile | Asp | Gly | Lys | |
| 20 | | | | 25 | | | | | 30 | | | | | 35 | | |

| cca | tta | aaa | gaa | cac | tta | aga | ttt | agc | gta | gcc | tac | tgg | cat | aca | ttt | 201 |
|---|---|---|---|---|---|---|---|---|---|---|---|---|---|---|---|---|
| Pro | Leu | Lys | Glu | His | Leu | Arg | Phe | Ser | Val | Ala | Tyr | Trp | His | Thr | Phe | |
| | | | 40 | | | | | 45 | | | | | 50 | | | |

| acc | gct | aac | gga | acg | gat | cca | ttt | ggt | gca | ccg | act | atg | cag | cgt | cct | 249 |
|---|---|---|---|---|---|---|---|---|---|---|---|---|---|---|---|---|
| Thr | Ala | Asn | Gly | Thr | Asp | Pro | Phe | Gly | Ala | Pro | Thr | Met | Gln | Arg | Pro | |
| | | 55 | | | | | 60 | | | | | 65 | | | | |

| tgg | gat | cat | ttt | acc | gac | cct | atg | gac | ata | gca | aaa | gca | cgt | gtg | gaa | 297 |
|---|---|---|---|---|---|---|---|---|---|---|---|---|---|---|---|---|
| Trp | Asp | His | Phe | Thr | Asp | Pro | Met | Asp | Ile | Ala | Lys | Ala | Arg | Val | Glu | |
| | 70 | | | | | 75 | | | | | 80 | | | | | |

| gcc | gca | ttc | gag | ctt | ttt | gaa | aaa | ttg | gat | gtt | cca | ttc | ttc | tgt | ttt | 345 |
|---|---|---|---|---|---|---|---|---|---|---|---|---|---|---|---|---|

```
Ala Ala Phe Glu Leu Phe Glu Lys Leu Asp Val Pro Phe Phe Cys Phe
    85                  90                  95 cat gac aga gat ata gct ccg gaa ggt gaa aca ttg aga gaa acc aac         393
His Asp Arg Asp Ile Ala Pro Glu Gly Glu Thr Leu Arg Glu Thr Asn
100                 105                 110                 115 aaa aac tta gat act atc gtt gct atg att aaa gac tac tta aaa acg         441
Lys Asn Leu Asp Thr Ile Val Ala Met Ile Lys Asp Tyr Leu Lys Thr
                    120                 125                 130 tca aag act aaa gtt ctt tgg ggc act gct aat ttg ttt tct aat cca         489
Ser Lys Thr Lys Val Leu Trp Gly Thr Ala Asn Leu Phe Ser Asn Pro
                135                 140                 145 cgt ttc gtg cat ggc gct gcc aca tca tgt aat gca gac gta ttt gct         537
Arg Phe Val His Gly Ala Ala Thr Ser Cys Asn Ala Asp Val Phe Ala
            150                 155                 160 tat gca gcc gct caa gtt aaa aag gcc tta gag att acc aaa gag tta         585
Tyr Ala Ala Ala Gln Val Lys Lys Ala Leu Glu Ile Thr Lys Glu Leu
            165                 170                 175 gga ggc cag aat tat gtt ttc tgg ggt ggt cgt gag gga tat gag aca         633
Gly Gly Gln Asn Tyr Val Phe Trp Gly Gly Arg Glu Gly Tyr Glu Thr
180                 185                 190                 195 ctt tta aat act gat atg gag ttg gaa tta gat aat tta gca aga ttc         681
Leu Leu Asn Thr Asp Met Glu Leu Glu Leu Asp Asn Leu Ala Arg Phe
                    200                 205                 210 tta cac atg gca gta gaa tat gct cag gaa att ggt ttt gaa gga cag         729
Leu His Met Ala Val Glu Tyr Ala Gln Glu Ile Gly Phe Glu Gly Gln
                215                 220                 225 ttc ttg atc gag cct aaa cca aag gaa cca aca aag cat cag tat gat         777
Phe Leu Ile Glu Pro Lys Pro Lys Glu Pro Thr Lys His Gln Tyr Asp
            230                 235                 240 ttc gac gct gct tct gta cac gcc ttt ttg aag aag tat gat ttg gat         825
Phe Asp Ala Ala Ser Val His Ala Phe Leu Lys Lys Tyr Asp Leu Asp
            245                 250                 255 aaa tac ttt aag ttg aac ata gag gct aat cac gca acg ttg gca ggt         873
Lys Tyr Phe Lys Leu Asn Ile Glu Ala Asn His Ala Thr Leu Ala Gly
260                 265                 270                 275 cac gat ttt caa cac gaa ttg aga tac gcc cgt att aat aac atg tta         921
His Asp Phe Gln His Glu Leu Arg Tyr Ala Arg Ile Asn Asn Met Leu
                    280                 285                 290 ggt tcc ata gat gcc aac atg ggt gac atg ttg ctg ggt tgg gat act         969
Gly Ser Ile Asp Ala Asn Met Gly Asp Met Leu Leu Gly Trp Asp Thr
                295                 300                 305 gat caa tac cca acg gat att aga atg aca act tta gca atg tac gag         1017
Asp Gln Tyr Pro Thr Asp Ile Arg Met Thr Thr Leu Ala Met Tyr Glu
            310                 315                 320 gtc att aaa atg gga ggt ttt aac aaa gga ggt ttg aat ttc gat gct         1065
Val Ile Lys Met Gly Gly Phe Asn Lys Gly Gly Leu Asn Phe Asp Ala
            325                 330                 335 aaa gtg cgt cgt gcc tct ttt gaa cct gaa gac ctt ttt ctt gga cat         1113
Lys Val Arg Arg Ala Ser Phe Glu Pro Glu Asp Leu Phe Leu Gly His
340                 345                 350                 355 att gcc gga atg gat gca ttt gca aaa ggt ttc aag gtc gct tat aag         1161
Ile Ala Gly Met Asp Ala Phe Ala Lys Gly Phe Lys Val Ala Tyr Lys
                    360                 365                 370 ctt gtt aag gat ggt gta ttt gat aga ttc att gaa gag aga tac aaa         1209
Leu Val Lys Asp Gly Val Phe Asp Arg Phe Ile Glu Glu Arg Tyr Lys
                375                 380                 385 tcc tat cgt gaa ggt ata ggt gct gaa atc gtt tca ggt aag gcc aat         1257
Ser Tyr Arg Glu Gly Ile Gly Ala Glu Ile Val Ser Gly Lys Ala Asn
            390                 395                 400
```

-continued

```
ttt aag act tta gag gaa tat gca ttg aat aac cca aaa atc gaa aac      1305
Phe Lys Thr Leu Glu Glu Tyr Ala Leu Asn Asn Pro Lys Ile Glu Asn
    405                 410                 415 aaa agc ggt aaa cag gaa ctg ctg gaa tct att ttg aat caa tat ttg      1353
Lys Ser Gly Lys Gln Glu Leu Leu Glu Ser Ile Leu Asn Gln Tyr Leu
420                 425                 430                 435 ttc tct gaa tag cctaggctcg aggaattc                                  1383
Phe Ser Glu
```

<210> SEQ ID NO 7
<211> LENGTH: 1386
<212> TYPE: DNA
<213> ORGANISM: Artificial Sequence
<220> FEATURE:
<223> OTHER INFORMATION: Artificial Thermoanaerobacter
      thermosulphurigenes xylose isomerase gene
<220> FEATURE:
<221> NAME/KEY: CDS
<222> LOCATION: (49)..(1368)

<400> SEQUENCE: 7

```
gaattcctag aaataatttt gtttaacttt aagaaggagg agctagcc atg gcc aag       57
                                                    Met Ala Lys
                                                    1 tat ttt gag aat gtt tcc aag att aag tat gaa ggt cct aag tca aac      105
Tyr Phe Glu Asn Val Ser Lys Ile Lys Tyr Glu Gly Pro Lys Ser Asn
    5                   10                  15 aac cct tac tcc ttc aaa ttc tat aat cca gaa gaa gtt ata gac ggt      153
Asn Pro Tyr Ser Phe Lys Phe Tyr Asn Pro Glu Glu Val Ile Asp Gly
20                  25                  30                  35 aaa acg atg gag gaa cac tta aga ttt tct att gct tac tgg cac aca      201
Lys Thr Met Glu Glu His Leu Arg Phe Ser Ile Ala Tyr Trp His Thr
                40                  45                  50 ttt act gcc gac ggc aca gac caa ttc gga aag gct act atg caa aga      249
Phe Thr Ala Asp Gly Thr Asp Gln Phe Gly Lys Ala Thr Met Gln Arg
            55                  60                  65 ccg tgg aac cat tac act gat cca atg gac ata gcc aaa gcc aga gtg      297
Pro Trp Asn His Tyr Thr Asp Pro Met Asp Ile Ala Lys Ala Arg Val
        70                  75                  80 gag gct gca ttc gag ttc ttc gat aag ata aac gcc cct tac ttc tgc      345
Glu Ala Ala Phe Glu Phe Phe Asp Lys Ile Asn Ala Pro Tyr Phe Cys
    85                  90                  95 ttc cat gat cgt gac att gct ccg gaa ggc gat acc ttg aga gaa acc      393
Phe His Asp Arg Asp Ile Ala Pro Glu Gly Asp Thr Leu Arg Glu Thr
100                 105                 110                 115 aac aaa aat ctt gac acc att gtc gca atg ata aaa gat tat ttg aag      441
Asn Lys Asn Leu Asp Thr Ile Val Ala Met Ile Lys Asp Tyr Leu Lys
                120                 125                 130 acg tct aaa acc aaa gtt ttg tgg ggt acg gca aac tta ttt tct aat      489
Thr Ser Lys Thr Lys Val Leu Trp Gly Thr Ala Asn Leu Phe Ser Asn
            135                 140                 145 ccg aga ttt gtt cat ggt gct tcc aca tcc tgc aac gca gat gtc ttt      537
Pro Arg Phe Val His Gly Ala Ser Thr Ser Cys Asn Ala Asp Val Phe
        150                 155                 160 gct tat tcc gct gct caa gtc aaa aag gct ctt gag ata acc aaa gaa      585
Ala Tyr Ser Ala Ala Gln Val Lys Lys Ala Leu Glu Ile Thr Lys Glu
    165                 170                 175 tta ggt ggt gaa aac tac gtt ttc tgg ggt ggc aga gaa ggt tat gag      633
Leu Gly Gly Glu Asn Tyr Val Phe Trp Gly Gly Arg Glu Gly Tyr Glu
180                 185                 190                 195 act ctt tta aat aca gat atg gaa ttt gaa ctt gac aat ttc gca aga      681
Thr Leu Leu Asn Thr Asp Met Glu Phe Glu Leu Asp Asn Phe Ala Arg
```

```
                          200                 205                 210
ttc ttg cac atg gct gtc gat tat gcc aag gag ata ggt ttt gaa ggc      729
Phe Leu His Met Ala Val Asp Tyr Ala Lys Glu Ile Gly Phe Glu Gly
            215                 220                 225 cag ttc ttg att gaa ccg aaa cca aag gaa cct acc aaa cat cag tat      777
Gln Phe Leu Ile Glu Pro Lys Pro Lys Glu Pro Thr Lys His Gln Tyr
        230                 235                 240 gac ttt gat gtc gca aat gtt ttg gct ttc ttg aga aaa tac gat tta      825
Asp Phe Asp Val Ala Asn Val Leu Ala Phe Leu Arg Lys Tyr Asp Leu
    245                 250                 255 gat aag tat ttc aaa gta aat att gaa gct aat cat gca acg ttg gcc      873
Asp Lys Tyr Phe Lys Val Asn Ile Glu Ala Asn His Ala Thr Leu Ala
260                 265                 270                 275 ttc cat gat ttc cag cac gag ttg aga tac gct aga atc aat gga gtc      921
Phe His Asp Phe Gln His Glu Leu Arg Tyr Ala Arg Ile Asn Gly Val
                280                 285                 290 tta gga tct atc gat gct aat acc ggt gat atg ctg ctg gga tgg gat      969
Leu Gly Ser Ile Asp Ala Asn Thr Gly Asp Met Leu Leu Gly Trp Asp
            295                 300                 305 act gat caa ttt ccg acc gat att cgt atg act acc ctg gca atg tat     1017
Thr Asp Gln Phe Pro Thr Asp Ile Arg Met Thr Thr Leu Ala Met Tyr
        310                 315                 320 gaa gtt att aag atg ggt gga ttt gat aaa ggc ggt ctg aac ttc gat     1065
Glu Val Ile Lys Met Gly Gly Phe Asp Lys Gly Gly Leu Asn Phe Asp
    325                 330                 335 gca aaa gta aga aga gct tct ttt gaa cct gaa gat ttg ttt tta gga     1113
Ala Lys Val Arg Arg Ala Ser Phe Glu Pro Glu Asp Leu Phe Leu Gly
340                 345                 350                 355 cac atc gct ggc atg gac gca ttt gct aaa ggt ttt aag gta gcc tat     1161
His Ile Ala Gly Met Asp Ala Phe Ala Lys Gly Phe Lys Val Ala Tyr
                360                 365                 370 aag ctt gta aaa gat aga gtg ttc gac aaa ttc atc gaa gag aga tat     1209
Lys Leu Val Lys Asp Arg Val Phe Asp Lys Phe Ile Glu Glu Arg Tyr
            375                 380                 385 gct tct tat aag gac gga ata gga gcc gat ata gtt tcc ggt aag gcc     1257
Ala Ser Tyr Lys Asp Gly Ile Gly Ala Asp Ile Val Ser Gly Lys Ala
        390                 395                 400 gat ttc aga tct ctt gag aaa tac gcc ttg gaa aga tca caa atc gtg     1305
Asp Phe Arg Ser Leu Glu Lys Tyr Ala Leu Glu Arg Ser Gln Ile Val
    405                 410                 415 aac aaa tca ggc cgt caa gaa ttg tta gaa tca att ctt aat caa tac     1353
Asn Lys Ser Gly Arg Gln Glu Leu Leu Glu Ser Ile Leu Asn Gln Tyr
420                 425                 430                 435 ctg ttc gct gaa tag cctaggctcg aggaattc                             1386
Leu Phe Ala Glu
```

```
<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
tagctagcat gtcgtacttc cccactgtcg ac                                   32

<210> SEQ ID NO 9
<211> LENGTH: 33
<212> TYPE: DNA
<213> ORGANISM: Artificial Sequence
<220> FEATURE:
```

<223> OTHER INFORMATION: Primer

<400> SEQUENCE: 9
ataagctttc aggtgtagat aaagcggttg acc    33

<210> SEQ ID NO 10
<211> LENGTH: 1320
<212> TYPE: DNA
<213> ORGANISM: Lactococcus lactis subsp. lactis

<400> SEQUENCE: 10

```
atggcttact ttaacgacat cgcacctatc aaatacgaag gtacaaaaac taaaaatatg    60
tttgccttc gtcattataa tccagaagaa gtagttgctg gtaaaacaat ggaagaacaa   120
cttcattttg cccttgcatt ttggcataca attacgatgg atgggtcaga tccctttggg   180
ggagcaacaa tggaacgtcc ttgggatttg aaggtggtt ctgaacttga ccgtgctcac   240
cgtcgagtag atgctttctt tgaaattgct gaaaaattag gtgttaaata ttattgtttc   300
catgatattg atattgcacc tactggaaat tctttgaaag aattttatgc taatttggac   360
gaaattactg accaccttct tgaaaaacaa aaagcaacag gcattaaatt actttggaat   420
acagcaaaca tgttttcaaa tccccgctat atgaatggtg tttcaacttc taatcgtgct   480
gaagtctttg cttatggtgc tgcacaagtt aaaaaaggtc ttgaactttc taaaaaactc   540
ggtggtgaaa attatgtctt ctggggtggt cgtgaaggtt atgaatcact tttgaataca   600
gatatgggtc ttgaaatgga tcatatggca aaattcttcc atttggcaat tgattatgca   660
aaatcaatca accacttgcc tattttcttg attgaaccaa aaccaaaaga accaatgact   720
caccaatatg attttgactc agcaacagct cttgctttct tgcaaaaata tgacttggac   780
aaaatacttca aactcaatct tgaaacaaat catgcttggt tggctgggca cacttttgaa   840
cacgaattaa atactgcacg tactttcaat gctttgggtt ctattgatgc caatcaagga   900
aattacttgc ttggttggga tacagatgaa ttcccaacac ttgttattga tatcacactt   960
gcgatgcacc aaattctttt gaacggtgga cttggcaaag gtggaattaa ctttgatgcg  1020
aaagtacgtc gtacaagttt caaagcagaa gatttaattc ttgctcatat tgcagggatg  1080
gatacttatg cgcgtgcttt gaaaggtgca gcagcaatca ttgaagataa attcttgtct  1140
gatattgttg acgaacgtta tagttcatac aaaaatacag aagttggtca atccattgaa  1200
aatggaacag caacttttga agtcttgct gcatttgcac ttgaacatgg tgacgatatt  1260
gaacttgatt ctaatcactt ggaatacatc aaatcagtat tgaatgacta tcttgtttaa  1320
```

<210> SEQ ID NO 11
<211> LENGTH: 439
<212> TYPE: PRT
<213> ORGANISM: Lactococcus lactis subsp. lactis

<400> SEQUENCE: 11

```
Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
```

```
                65                  70                  75                  80
           Arg Arg Val Asp Ala Phe Phe Glu Ile Ala Glu Lys Leu Gly Val Lys
                           85                  90                  95

Tyr Tyr Cys Phe His Asp Ile Asp Ile Ala Pro Thr Gly Asn Ser Leu
                          100                 105                 110

Lys Glu Phe Tyr Ala Asn Leu Asp Glu Ile Thr Asp His Leu Leu Glu
                          115                 120                 125

Lys Gln Lys Ala Thr Gly Ile Lys Leu Leu Trp Asn Thr Ala Asn Met
                          130                 135                 140

Phe Ser Asn Pro Arg Tyr Met Asn Gly Val Ser Thr Ser Asn Arg Ala
           145                 150                 155                 160

Glu Val Phe Ala Tyr Gly Ala Ala Gln Val Lys Lys Gly Leu Glu Leu
                          165                 170                 175

Ser Lys Lys Leu Gly Gly Glu Asn Tyr Val Phe Trp Gly Gly Arg Glu
                          180                 185                 190

Gly Tyr Glu Ser Leu Leu Asn Thr Asp Met Gly Leu Glu Met Asp His
                          195                 200                 205

Met Ala Lys Phe Phe His Leu Ala Ile Asp Tyr Ala Lys Ser Ile Asn
                          210                 215                 220

His Leu Pro Ile Phe Leu Ile Glu Pro Lys Pro Lys Glu Pro Met Thr
           225                 230                 235                 240

His Gln Tyr Asp Phe Asp Ser Ala Thr Ala Leu Ala Phe Leu Gln Lys
                          245                 250                 255

Tyr Asp Leu Asp Lys Tyr Phe Lys Leu Asn Leu Glu Thr Asn His Ala
                          260                 265                 270

Trp Leu Ala Gly His Thr Phe Glu His Glu Leu Asn Thr Ala Arg Thr
                          275                 280                 285

Phe Asn Ala Leu Gly Ser Ile Asp Ala Asn Gln Gly Asn Tyr Leu Leu
                          290                 295                 300

Gly Trp Asp Thr Asp Glu Phe Pro Thr Leu Val Ile Asp Ile Thr Leu
           305                 310                 315                 320

Ala Met His Gln Ile Leu Leu Asn Gly Gly Leu Gly Lys Gly Gly Ile
                          325                 330                 335

Asn Phe Asp Ala Lys Val Arg Arg Thr Ser Phe Lys Ala Glu Asp Leu
                          340                 345                 350

Ile Leu Ala His Ile Ala Gly Met Asp Thr Tyr Ala Arg Ala Leu Lys
                          355                 360                 365

Gly Ala Ala Ile Ile Glu Asp Lys Phe Leu Ser Asp Ile Val Asp
                          370                 375                 380

Glu Arg Tyr Ser Ser Tyr Lys Asn Thr Glu Val Gly Gln Ser Ile Glu
           385                 390                 395                 400

Asn Gly Thr Ala Thr Phe Glu Ser Leu Ala Ala Phe Ala Leu Glu His
                          405                 410                 415

Gly Asp Asp Ile Glu Leu Asp Ser Asn His Leu Glu Tyr Ile Lys Ser
                          420                 425                 430

Val Leu Asn Asp Tyr Leu Val
                          435

<210> SEQ ID NO 12
<211> LENGTH: 1320
<212> TYPE: DNA
<213> ORGANISM: Lactococcus lactis subsp. lactis

<400> SEQUENCE: 12
```

```
atggcttact ttaacgacat cgcacctatc aaatacgaag gtacaaaaac taaaaatatg      60 tttgccttc gccattataa tccagaagaa gtagttgctg gtaaaacaat ggaagaacaa      120
cttcattttg cccttgcatt tggcataca attacaatgg atgggtcaga ccccttgggg      180
ggagcaacaa tggaacgtcc ttgggatttg aaggtggtt ctgaacttga ccgtgctcac      240
cgtcgagtag atgctttctt tgaaattgct gaaaaattag gtgttaaata ttattgtttc      300
catgatattg atattgcacc tactggaaat tctttgaaag aatttatgc taatttggac      360 gaaattactg accaccttct tgaaaaacaa aaagcaacag ggattaaatt actttggaat      420
acagcaaaca tgttttcaaa tccccgctat atgaatggtg tttcaacttc taaccgtgct      480
gaagtctttg cttatggtgc tgcacaagtt aaaaaaggtc ttgaactttc taaaaaactc      540
ggtggtgaaa attacgtctt ctgggtggt cgtgaaggtt atgaatcact tttgaataca      600
gatatgggtc ttgaaatgga tcatatggca aaattcttcc atttggcaat tgattatgca      660
aaatcaatca accacttgcc catttcttg atcgaaccaa aaccaaaaga accaatgact      720
caccaatatg attttgactc agcaacagct cttgctttct tgcaaaaata tgatttggac      780
aaatatttca aactcaatct tgaaacaaat catgcttggt tggctggaca cacttttgaa      840
cacgaattaa atactgctcg tactttcaat gctttgggtt ctattgatgc caatcaagga      900
aattacttgc ttggttggga tacagatgaa ttcccaacac ttgttattga tatcacactt      960
gcgatgcacc aaaattctttt gaacggtgga cttggcaaag gtggaattaa ctttgatgcg      1020
aaagtacgtc gtacaagttt caaagcagaa gatttaattc ttgctcatat gcagggatg       1080 gatacttatg cgcgtgctttt gaaaggtgca gcagcaatca ttgaagataa attcttgtct      1140
gatattgttg acgaacgtta tagttcatac aaaaatacag aagttggaca atccattgaa      1200
aatggaacag caacttttaa aagtcttgcc gcatttgcac ttgaacatgg tgacgatatt      1260
gaacttgatt ctaatcactt ggaatacatc aaatcagtat tgaatgacta tcttgtttaa      1320
```

<210> SEQ ID NO 13
<211> LENGTH: 439
<212> TYPE: PRT
<213> ORGANISM: Lactococcus lactis subsp. lactis

<400> SEQUENCE: 13

```
Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
                85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
    130                 135                 140
```

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
            165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
            195                 200                 205

Met Ala Lys Phe Phe His Leu Ala Ile Asp Tyr Ala Lys Ser Ile Asn
            210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
            275                 280                 285

Phe Asn Ala Leu Gly Ser Ile Asp Ala Asn Gln Gly Asn Tyr Leu Leu
290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
            340                 345                 350

Ile Leu Ala His Ile Ala Gly Met Asp Thr Tyr Ala Arg Ala Leu Lys
            355                 360                 365

Gly Ala Ala Ile Ile Glu Asp Lys Phe Leu Ser Asp Ile Val Asp
            370                 375                 380

Glu Arg Tyr Ser Ser Tyr Lys Asn Thr Glu Val Gly Gln Ser Ile Glu
385                 390                 395                 400

Asn Gly Thr Ala Thr Phe Lys Ser Leu Ala Ala Phe Ala Leu Glu His
                405                 410                 415

Gly Asp Asp Ile Glu Leu Asp Ser Asn His Leu Glu Tyr Ile Lys Ser
            420                 425                 430

Val Leu Asn Asp Tyr Leu Val
            435

<210> SEQ ID NO 14
<211> LENGTH: 439
<212> TYPE: PRT
<213> ORGANISM: Lactococcus lactis subsp. lactis

<400> SEQUENCE: 14

Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
            85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
            115                 120                 125

Lys Gln Lys Ala Thr Gly Ile Lys Leu Leu Trp Asn Thr Ala Asn Met
        130                 135                 140

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
    210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
    290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
            340                 345                 350

Ile Leu Ala His Ile Ala Gly Met Asp Thr Tyr Ala Arg Ala Leu Lys
        355                 360                 365

Gly Ala Ala Ile Ile Glu Asp Lys Phe Leu Ser Asp Ile Val Asp
370                 375                 380

Glu Arg Tyr Ser Ser Tyr Lys Asn Thr Glu Val Gly Gln Ser Ile Glu
385                 390                 395                 400

Asn Gly Thr Ala Thr Phe Glu Ser Leu Ala Ala Phe Ala Leu Glu Tyr
                405                 410                 415

Gly Asp Asp Ile Glu Leu Asp Ser Asn His Leu Glu Tyr Ile Lys Ser
            420                 425                 430

Val Leu Asn Asp Tyr Leu Val
        435

<210> SEQ ID NO 15
<211> LENGTH: 438
<212> TYPE: PRT
<213> ORGANISM: Artificial Sequence
<220> FEATURE:
<223> OTHER INFORMATION: Synthetic Construct

<400> SEQUENCE: 15

-continued

```
Met Glu Tyr Phe Lys Asn Val Pro Gln Ile Lys Tyr Glu Gly Pro Lys
1               5                   10                  15

Ser Asn Asn Pro Tyr Ala Phe Lys Phe Tyr Asn Pro Asp Glu Ile Ile
                20                  25                  30

Asp Gly Lys Pro Leu Lys Glu His Leu Arg Phe Ser Val Ala Tyr Trp
            35                  40                  45

His Thr Phe Thr Ala Asn Gly Thr Asp Pro Phe Gly Ala Pro Thr Met
        50                  55                  60

Gln Arg Pro Trp Asp His Phe Thr Asp Pro Met Asp Ile Ala Lys Ala
65                      70                  75                  80

Arg Val Glu Ala Ala Phe Glu Leu Phe Glu Lys Leu Asp Val Pro Phe
                85                  90                  95

Phe Cys Phe His Asp Arg Asp Ile Ala Pro Glu Gly Glu Thr Leu Arg
            100                 105                 110

Glu Thr Asn Lys Asn Leu Asp Thr Ile Val Ala Met Ile Lys Asp Tyr
        115                 120                 125

Leu Lys Thr Ser Lys Thr Lys Val Leu Trp Gly Thr Ala Asn Leu Phe
    130                 135                 140

Ser Asn Pro Arg Phe Val His Gly Ala Ala Thr Ser Cys Asn Ala Asp
145                 150                 155                 160

Val Phe Ala Tyr Ala Ala Ala Gln Val Lys Lys Ala Leu Glu Ile Thr
                165                 170                 175

Lys Glu Leu Gly Gly Gln Asn Tyr Val Phe Trp Gly Gly Arg Glu Gly
            180                 185                 190

Tyr Glu Thr Leu Leu Asn Thr Asp Met Glu Leu Glu Leu Asp Asn Leu
        195                 200                 205

Ala Arg Phe Leu His Met Ala Val Glu Tyr Ala Gln Glu Ile Gly Phe
    210                 215                 220

Glu Gly Gln Phe Leu Ile Glu Pro Lys Pro Lys Glu Pro Thr Lys His
225                 230                 235                 240

Gln Tyr Asp Phe Asp Ala Ala Ser Val His Ala Phe Leu Lys Lys Tyr
                245                 250                 255

Asp Leu Asp Lys Tyr Phe Lys Leu Asn Ile Glu Ala Asn His Ala Thr
            260                 265                 270

Leu Ala Gly His Asp Phe Gln His Glu Leu Arg Tyr Ala Arg Ile Asn
        275                 280                 285

Asn Met Leu Gly Ser Ile Asp Ala Asn Met Gly Asp Met Leu Leu Gly
    290                 295                 300

Trp Asp Thr Asp Gln Tyr Pro Thr Asp Ile Arg Met Thr Thr Leu Ala
305                 310                 315                 320

Met Tyr Glu Val Ile Lys Met Gly Gly Phe Asn Lys Gly Gly Leu Asn
                325                 330                 335

Phe Asp Ala Lys Val Arg Arg Ala Ser Phe Glu Pro Glu Asp Leu Phe
            340                 345                 350

Leu Gly His Ile Ala Gly Met Asp Ala Phe Ala Lys Gly Phe Lys Val
        355                 360                 365

Ala Tyr Lys Leu Val Lys Asp Gly Val Phe Asp Arg Phe Ile Glu Glu
    370                 375                 380

Arg Tyr Lys Ser Tyr Arg Glu Gly Ile Gly Ala Glu Ile Val Ser Gly
385                 390                 395                 400

Lys Ala Asn Phe Lys Thr Leu Glu Glu Tyr Ala Leu Asn Asn Pro Lys
                405                 410                 415
```

```
Ile Glu Asn Lys Ser Gly Lys Gln Glu Leu Leu Glu Ser Ile Leu Asn
            420                 425                 430

Gln Tyr Leu Phe Ser Glu
            435

<210> SEQ ID NO 16
<211> LENGTH: 439
<212> TYPE: PRT
<213> ORGANISM: Artificial Sequence
<220> FEATURE:
<223> OTHER INFORMATION: Synthetic Construct

<400> SEQUENCE: 16

Met Ala Lys Tyr Phe Glu Asn Val Ser Lys Ile Lys Tyr Glu Gly Pro
1               5                   10                  15

Lys Ser Asn Asn Pro Tyr Ser Phe Lys Phe Tyr Asn Pro Glu Glu Val
            20                  25                  30

Ile Asp Gly Lys Thr Met Glu Glu His Leu Arg Phe Ser Ile Ala Tyr
            35                  40                  45

Trp His Thr Phe Thr Ala Asp Gly Thr Asp Gln Phe Gly Lys Ala Thr
        50                  55                  60

Met Gln Arg Pro Trp Asn His Tyr Thr Asp Pro Met Asp Ile Ala Lys
65                  70                  75                  80

Ala Arg Val Glu Ala Ala Phe Glu Phe Phe Asp Lys Ile Asn Ala Pro
                85                  90                  95

Tyr Phe Cys Phe His Asp Arg Asp Ile Ala Pro Glu Gly Asp Thr Leu
            100                 105                 110

Arg Glu Thr Asn Lys Asn Leu Asp Thr Ile Val Ala Met Ile Lys Asp
            115                 120                 125

Tyr Leu Lys Thr Ser Lys Thr Lys Val Leu Trp Gly Thr Ala Asn Leu
        130                 135                 140

Phe Ser Asn Pro Arg Phe Val His Gly Ala Ser Thr Ser Cys Asn Ala
145                 150                 155                 160

Asp Val Phe Ala Tyr Ser Ala Ala Gln Val Lys Lys Ala Leu Glu Ile
                165                 170                 175

Thr Lys Glu Leu Gly Gly Glu Asn Tyr Val Phe Trp Gly Gly Arg Glu
            180                 185                 190

Gly Tyr Glu Thr Leu Leu Asn Thr Asp Met Glu Phe Glu Leu Asp Asn
        195                 200                 205

Phe Ala Arg Phe Leu His Met Ala Val Asp Tyr Ala Lys Glu Ile Gly
    210                 215                 220

Phe Glu Gly Gln Phe Leu Ile Glu Pro Lys Pro Lys Glu Pro Thr Lys
225                 230                 235                 240

His Gln Tyr Asp Phe Asp Val Ala Asn Val Leu Ala Phe Leu Arg Lys
                245                 250                 255

Tyr Asp Leu Asp Lys Tyr Phe Lys Val Asn Ile Glu Ala Asn His Ala
            260                 265                 270

Thr Leu Ala Phe His Asp Phe Gln His Glu Leu Arg Tyr Ala Arg Ile
        275                 280                 285

Asn Gly Val Leu Gly Ser Ile Asp Ala Asn Thr Gly Asp Met Leu Leu
    290                 295                 300

Gly Trp Asp Thr Asp Gln Phe Pro Thr Asp Ile Arg Met Thr Thr Leu
305                 310                 315                 320

Ala Met Tyr Glu Val Ile Lys Met Gly Gly Phe Asp Lys Gly Gly Leu
                325                 330                 335
```

Asn Phe Asp Ala Lys Val Arg Arg Ala Ser Phe Glu Pro Glu Asp Leu
            340                 345                 350

Phe Leu Gly His Ile Ala Gly Met Asp Ala Phe Ala Lys Gly Phe Lys
        355                 360                 365

Val Ala Tyr Lys Leu Val Lys Asp Arg Val Phe Asp Lys Phe Ile Glu
370                 375                 380

Glu Arg Tyr Ala Ser Tyr Lys Asp Gly Ile Gly Ala Asp Ile Val Ser
385                 390                 395                 400

Gly Lys Ala Asp Phe Arg Ser Leu Glu Lys Tyr Ala Leu Glu Arg Ser
                405                 410                 415

Gln Ile Val Asn Lys Ser Gly Arg Gln Glu Leu Leu Glu Ser Ile Leu
            420                 425                 430

Asn Gln Tyr Leu Phe Ala Glu
        435

<210> SEQ ID NO 17
<211> LENGTH: 1320
<212> TYPE: DNA
<213> ORGANISM: Lactococcus lactis

<400> SEQUENCE: 17
atggcttact ttaacgacat cgcacctatc aaatacgaag gtacaaaaac taaaaatatg      60
tttgcctttc gccattataa tccagaagaa gtagttgctg gtaaaacaat ggaagaacaa     120
cttcattttg cccttgcatt ttggcataca attacaatgg atgggtcaga tcccttgggg     180
ggagcaacaa tggaacgccc ttgggatttg aaggtggtt ctgaacttga ccgtgctcac     240
cgtcgagtag atgctttctt tgaaattgct gaaaaattag gtgttaaata ttattgtttc     300
catgatattg atattgcacc tactggaaat tctttgaaag aattttatgc taatttggac     360
gaaattactg accaccttct tgaaaaacaa aaagcaacag ggattaaatt actttggaat     420
acagcaaaca tgttttcaaa tccccgctat atgaatggtg tttcaacttc taatcgtgct     480
gaagtctttg cttatggtgc tgcacaagtt aaaaaaggtc ttgaactttc taaaaaactc     540
ggtggtgaaa attacgtctt ctggggtggt cgtgaaggtt atgaatcact tttgaataca     600
gatatgggtc ttgaaatgga tcatatggca aaattcttcc atttggcaat tgattatgca     660
aaatcaatca accacttgcc catttttctt gattgaaccaa aaccaaaaga accaatgact     720
caccaatatg atttttgactc agcaacagct cttgcttttct tgcaaaaata tgatttggac     780
aaatatttca aactcaatct tgaaacaaat catgcttggt tggctggaca cacttttgaa     840
cacgaattaa atactgctcg tactttcaat gctttgggtt ctattgatgc caatcaagga     900
aattacttgc ttggttggga tacagatgaa ttcccaacac ttgttattga tatcacactt     960
gcgatgcacc aaattctttt gaacggtgga cttggcaaag gtggaattaa ctttgatgcg    1020
aaagtacgtc gtacaagttt caaagcagaa gatttaattc ttgctcatat gcagggatg    1080 gatacttatg cgcgtgcttt gaaaggtgca gcagcaatca ttgaagataa attcttgtct    1140
gatattgttg acgaacgtta tagttcatac agaaaaatacag aagttggtca atccattgaa    1200
aatggaacag caacttttga aagtcttgcc gcatttgcac ttgaatatgg tgatgatatt    1260
gaacttgatt ctaatcactt ggaatacatc aaatcagtat tgaatgacta tcttgtttaa    1320

<210> SEQ ID NO 18
<211> LENGTH: 439
<212> TYPE: PRT
<213> ORGANISM: Lactococcus lactis

```
<400> SEQUENCE: 18

Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
                85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
130                 135                 140

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
    210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
            340                 345                 350

Ile Leu Ala His Ile Ala Gly Met Asp Thr Tyr Ala Arg Ala Leu Lys
        355                 360                 365

Gly Ala Ala Ala Ile Ile Glu Asp Lys Phe Leu Ser Asp Ile Val Asp
370                 375                 380

Glu Arg Tyr Ser Ser Tyr Arg Asn Thr Glu Val Gly Gln Ser Ile Glu
385                 390                 395                 400

Asn Gly Thr Ala Thr Phe Glu Ser Leu Ala Ala Phe Ala Leu Glu Tyr
                405                 410                 415
```

-continued

Gly Asp Asp Ile Glu Leu Asp Ser Asn His Leu Glu Tyr Ile Lys Ser
        420                 425                 430

Val Leu Asn Asp Tyr Leu Val
        435

<210> SEQ ID NO 19
<211> LENGTH: 439
<212> TYPE: PRT
<213> ORGANISM: Artificial Sequence
<220> FEATURE:
<223> OTHER INFORMATION: Variant of Lactococcus xylose isomerase

<400> SEQUENCE: 19

Met Ala Tyr Phe Asn Asp Ile Ala Pro Ile Lys Tyr Glu Gly Thr Lys
1               5                   10                  15

Thr Lys Asn Met Phe Ala Phe Arg His Tyr Asn Pro Glu Glu Val Val
            20                  25                  30

Ala Gly Lys Thr Met Glu Glu Gln Leu His Phe Ala Leu Ala Phe Trp
        35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Lys Leu Gly Val Lys
                85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
    130                 135                 140

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
    210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
    290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Gly Leu Gly Lys Gly Gly Ile
                325                 330                 335

Asn Phe Asp Ala Lys Val Arg Arg Thr Ser Phe Lys Ala Glu Asp Leu
                340                 345                 350

Ile Leu Ala His Ile Ala Gly Met Asp Thr Tyr Ala Arg Ala Leu Lys
            355                 360                 365

Gly Ala Ala Ile Ile Glu Asp Lys Phe Leu Ser Asp Ile Val Asp
370                 375                 380

Glu Arg Tyr Ser Ser Tyr Arg Asn Thr Glu Val Gly Gln Ser Ile Glu
385                 390                 395                 400

Asn Gly Thr Ala Thr Phe Lys Ser Leu Ala Ala Phe Ala Leu Glu His
                405                 410                 415

Gly Asp Asp Ile Glu Leu Asp Ser Asn His Leu Glu Tyr Ile Lys Ser
            420                 425                 430

Val Leu Asn Asp Tyr Leu Val
        435

<210> SEQ ID NO 20
<211> LENGTH: 439
<212> TYPE: PRT
<213> ORGANISM: Artificial Sequence
<220> FEATURE:
<223> OTHER INFORMATION: Variant of Lactococcus xylose isomerase

<400> SEQUENCE: 20

Met Ala Tyr Phe Asn Asp Ile Ala Pro Ile Tyr Glu Gly Thr Lys
1               5                   10                  15

Thr Lys Asn Met Phe Ala Phe Arg His Tyr Asn Pro Glu Glu Val Val
                20                  25                  30

Ala Gly Lys Thr Met Glu Glu Gln Leu His Phe Ala Leu Ala Phe Trp
            35                  40                  45

His Thr Ile Thr Met Asp Gly Ser Asp Pro Phe Gly Gly Ala Thr Met
    50                  55                  60

Glu Arg Pro Trp Asp Leu Glu Gly Gly Ser Glu Leu Asp Arg Ala His
65                  70                  75                  80

Arg Arg Val Asp Ala Phe Phe Glu Ile Ala Glu Lys Leu Gly Val Lys
                85                  90                  95

Tyr Tyr Cys Phe His Asp Ile Asp Ile Ala Pro Thr Gly Asn Ser Leu
            100                 105                 110

Lys Glu Phe Tyr Ala Asn Leu Asp Glu Ile Thr Asp His Leu Leu Glu
        115                 120                 125

Lys Gln Lys Ala Thr Gly Ile Lys Leu Leu Trp Asn Thr Ala Asn Met
130                 135                 140

Phe Ser Asn Pro Arg Tyr Met Asn Gly Val Ser Thr Ser Asn Arg Ala
145                 150                 155                 160

Glu Val Phe Ala Tyr Gly Ala Ala Gln Val Lys Lys Gly Leu Glu Leu
                165                 170                 175

Ser Lys Lys Leu Gly Gly Glu Asn Tyr Val Phe Trp Gly Gly Arg Glu
            180                 185                 190

Gly Tyr Glu Ser Leu Leu Asn Thr Asp Met Gly Leu Glu Met Asp His
        195                 200                 205

Met Ala Lys Phe Phe His Leu Ala Ile Asp Tyr Ala Lys Ser Ile Asn
210                 215                 220

His Leu Pro Ile Phe Leu Ile Glu Pro Lys Pro Lys Glu Pro Met Thr
225                 230                 235                 240

His Gln Tyr Asp Phe Asp Ser Ala Thr Ala Leu Ala Phe Leu Gln Lys
                245                 250                 255

-continued

Tyr Asp Leu Asp Lys Tyr Phe Lys Leu Asn Leu Glu Thr Asn His Ala
            260                 265                 270

Trp Leu Ala Gly His Thr Phe Glu His Glu Leu Asn Thr Ala Arg Thr
        275                 280                 285

Phe Asn Ala Leu Gly Ser Ile Asp Ala Asn Gln Gly Asn Tyr Leu Leu
    290                 295                 300

Gly Trp Asp Thr Asp Glu Phe Pro Thr Leu Val Ile Asp Ile Thr Leu
305                 310                 315                 320

Ala Met His Gln Ile Leu Leu Asn Gly Leu Gly Lys Gly Gly Ile
                325                 330                 335

Asn Phe Asp Ala Lys Val Arg Arg Thr Ser Phe Lys Ala Glu Asp Leu
                340                 345                 350

Ile Leu Ala His Ile Ala Gly Met Asp Thr Tyr Ala Arg Ala Leu Lys
                355                 360                 365

Gly Ala Ala Ala Ile Ile Glu Asp Lys Phe Leu Ser Asp Ile Val Asp
370                 375                 380

Glu Arg Tyr Ser Ser Tyr Arg Asn Thr Glu Val Gly Gln Ser Ile Glu
385                 390                 395                 400

Asn Gly Thr Ala Thr Phe Lys Ser Leu Ala Ala Phe Ala Leu Glu Tyr
                405                 410                 415

Gly Asp Asp Ile Glu Leu Asp Ser Asn His Leu Glu Tyr Ile Lys Ser
                420                 425                 430

Val Leu Asn Asp Tyr Leu Val
        435

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
gttgacgaac gatatagttc atacaaaaat acagaagttg g            41

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
ccaacttctg tattttttgta tgaactatat cgttcgtcaa c            41

<210> SEQ ID NO 23
<211> LENGTH: 55
<212> TYPE: DNA
<213> ORGANISM: Artificial Sequence
<220> FEATURE:
<223> OTHER INFORMATION: Primer

<400> SEQUENCE: 23
acagcaactt ttaaaagctt agccgcattt gcacttgaat atggtgatga tattg            55

<210> SEQ ID NO 24
<211> LENGTH: 55
<212> TYPE: DNA
<213> ORGANISM: Artificial Sequence
<220> FEATURE:

<223> OTHER INFORMATION: Primer

<400> SEQUENCE: 24
caatatcatc accatattca agtgcaaatg cggctaagct tttaaaagtt gctgt        55

<210> SEQ ID NO 25
<211> LENGTH: 55
<212> TYPE: DNA
<213> ORGANISM: Artificial Sequence
<220> FEATURE:
<223> OTHER INFORMATION: Primer

<400> SEQUENCE: 25
acagcaactt ttaaaagctt agccgcattt gcacttgaac atggtgatga tattg        55

<210> SEQ ID NO 26
<211> LENGTH: 55
<212> TYPE: DNA
<213> ORGANISM: Artificial Sequence
<220> FEATURE:
<223> OTHER INFORMATION: Primer

<400> SEQUENCE: 26
caatatcatc accatgttca agtgcaaatg cggctaagct tttaaaagtt gctgt        55

<210> SEQ ID NO 27
<211> LENGTH: 1320
<212> TYPE: DNA
<213> ORGANISM: Artificial Sequence
<220> FEATURE:
<223> OTHER INFORMATION: Variant of Lactococcus xylose isomerase

<400> SEQUENCE: 27
atggcttact ttaacgacat cgcacctatc aaatacgaag gtacaaaaac taaaaatatg        60
tttgcctttc gccattataa tccagaagaa gtagttgctg gtaaaacaat ggaagaacaa       120
cttcattttg cccttgcatt ttggcataca attacaatgg atgggtcaga tccctttggg       180
ggagcaacaa tggaacgccc ttgggatttg aaggtggtt ctgaacttga ccgtgctcac        240
cgtcgagtag atgctttctt tgaaattgct gaaaaattag tgttaaaata ttattgtttc       300
catgatattg atattgcacc tactggaaat tctttgaaag aatttttatg caatttggac       360
gaaattactg accaccttct tgaaaaacaa aaagcaacag ggattaaatt acttgaat        420 acagcaaaca tgttttcaaa tccccgctat atgaatggtg tttcaacttc taatcgtgct       480
gaagtctttg cttatggtgc tgcacaagtt aaaaaaggtc ttgaactttc taaaaaactc       540
ggtggtgaaa attcgtctt ctggggtggt cgtgaaggtt atgaatcact tttgaataca       600
gatatgggtc ttgaaatgga tcatatggca aaattcttcc atttggcaat tgattatgca       660
aaatcaatca accacttgcc cattttcttg attgaaccaa aaccaaaaga accaatgact       720
caccaatatg attttgactc agcaacagct cttgctttct tgcaaaaata tgatttggac       780
aaatatttca aactcaatct tgaaacaaat catgcttggt ggctggaca cacttttgaa        840 cacgaattaa atactgctcg tactttcaat gctttgggtt ctattgatgc caatcaagga       900
aattacttgc ttggttggga tacagatgaa ttcccaacac ttgttattga tatcacactt       960
gcgatgcacc aaattctttt gaacggtgga cttggcaaag gtggaattaa ctttgatgcg      1020
aaagtacgtc gtacaagttt caagcagaa gatttaattc ttgctcatat gcagggatg       1080 gatacttatg cgcgtgcttt gaaaggtgca gcagcaatca ttgaagataa attcttgtct      1140
gatattgttg acgaacgtta tagttcatac agaaatacag aagttggtca atccattgaa      1200

```
aatggaacag caacttttaa aagcttagcc gcatttgcac ttgaacatgg tgatgatatt    1260
gaacttgatt ctaatcactt ggaatacatc aaatcagtat tgaatgacta tcttgtttaa    1320
```

<210> SEQ ID NO 28
<211> LENGTH: 1320
<212> TYPE: DNA
<213> ORGANISM: Artificial Sequence
<220> FEATURE:
<223> OTHER INFORMATION: Variant of Lactococcus xylose isomerase

<400> SEQUENCE: 28

```
atggcttact ttaacgacat cgcacctatc aaatacgaag gtacaaaaac taaaaatatg      60
tttgcctttc gccattataa tccagaagaa gtagttgctg gtaaaacaat ggaagaacaa     120
cttcattttg cccttgcatt ttggcataca attacaatgg atgggtcaga tcccttggg     180 ggagcaacaa tggaacgccc ttgggatttg gaaggtggtt ctgaacttga ccgtgctcac     240
cgtcgagtag atgctttctt tgaaattgct gaaaaattag gtgttaaata ttattgtttc     300
catgatattg atattgcacc tactggaaat tctttgaaag aattttatgc taatttggac     360
gaaattactg accaccttct tgaaaaacaa aaagcaacag ggattaaatt actttggaat     420
acagcaaaca tgttttcaaa tccccgctat atgaatggtg tttcaacttc taatcgtgct     480
gaagtctttg cttatggtgc tgcacaagtt aaaaaaggtc ttgaactttc taaaaaactc     540
ggtggtgaaa attacgtctt ctggggtggt cgtgaaggtt atgaatcact tttgaataca     600
gatatgggtc ttgaaatgga tcatatggca aaattcttcc atttggcaat tgattatgca     660
aaatcaatca accacttgcc catttttcttg attgaaccaa aaccaaaaga accaatgact     720
caccaatatg attttgactc agcaacagct cttgctttct tgcaaaaata tgatttggac     780
aaatatttca aactcaatct tgaaacaaat catgcttggt tggctggaca cactttgaa     840 cacgaattaa atactgctcg tactttcaat gctttgggtt ctattgatgc caatcaagga     900
aattacttgc ttggttggga tacagatgaa ttcccaacac ttgttattga tatcacactt     960
gcgatgcacc aaattctttt gaacggtgga cttggcaaag gtggaattaa ctttgatgcg    1020
aaagtacgtc gtacaagttt caaagcagaa gatttaattc ttgctcatat tgcagggatg    1080
gatacttatg cgcgtgcttt gaaaggtgca gcagcaatca ttgaagataa attcttgtct    1140
gatattgttg acgaacgtta tagttcatac agaaatacag aagttggtca atccattgaa    1200
aatggaacag caacttttaa aagcttagcc gcatttgcac ttgaatatgg tgatgatatt    1260
gaacttgatt ctaatcactt ggaatacatc aaatcagtat tgaatgacta tcttgtttaa    1320
```

MICROORGANISM EXPRESSING XYLOSE ISOMERASE

CROSS-REFERENCE TO RELATED APPLICATIONS

This is a Divisional application of U.S. Ser. No. 13/133,242 filed Jun. 7, 2011, which is a national phase application claiming priority to PCT/IB2009/055652 filed Dec. 10, 2009, which claims priority under 35 U.S.C. §119 to provisional application U.S. Ser. No. 61/138,293 filed Dec. 17, 2008 and GB 0822937.9, all of which are herein incorporated by reference in their entirety.

FIELD OF THE INVENTION

The present invention relates to a microorganism.

In particular, the present invention relates to a transformed microorganism capable of: a higher xylose isomerase activity than the equivalent microorganism prior to transformation; and/or a higher growth rate in or on a growth medium comprising xylose than the equivalent microorganism prior to transformation; and/or a faster metabolism of xylose than the equivalent microorganism prior to transformation; and/or a higher production of ethanol when grown anaerobically on xylose as the carbon source than the equivalent microorganism prior to transformation.

The present invention further relates to a method for preparing transformed microorganisms capable of: a higher xylose isomerase activity than the microorganism prior to transformation; and/or a higher growth rate in or on a growth medium comprising xylose than the microorganism prior to transformation; and/or a faster metabolism of xylose than the microorganism prior to transformation; and/or a higher production of ethanol when grown anaerobically on xylose as the carbon source than the microorganism prior to transformation.

Further, the present invention relates to inocula and culture media comprising a microorganism according to the present invention or a microorganism prepared by a method according to the present invention.

In another aspect, the present invention relates to a fermentation method comprising culturing in a culture medium a microorganism according to the present invention or a microorganism prepared by the method of the present invention.

The present invention additionally relates to methods for producing a biofuel and/or a product derived from xylose comprising culturing in a culture medium a microorganism of the present invention or a microorganism prepared by the method of the present invention.

In addition the present invention relates to a biofuel and/or a product derived from xylose obtained by a method of the present invention.

Further, the present invention relates to the use of a microorganism according to the present invention or a microorganism prepared by the method of the present invention for the production of a product derived from xylose and/or a biofuel.

BACKGROUND

Ethanol is considered an attractive alternative transportation fuel that may be used as an additive to, a supplement to or a part replacement for the fossil fuel gasoline, which is an ultimately limited resource.

Ethanol may be used in smaller concentrations instead of Methyl tert-butyl ether (MTBE) as a cleaner octane booster or oxygenating additive to gasoline, or it may be used for blending into gasoline in higher amounts from 10 to 85%, where the mixtures can be used in only slightly modified automobile engines as we know them today. It therefore has a tremendous advantage over other alternative transportation fuels. Any fractional substitution can be done with maximum flexibility, and this without drastic changes in transportation engine technology as we know it today.

Ethanol has the advantage of being a renewable resource, as it can be produced in very large amounts from plant material. From this also follows the advantage of having a low net contribution to the release of carbon dioxide to the atmosphere as the carbon dioxide released by the use of the ethanol is reabsorbed by the necessary production of the plant material to regenerate the used ethanol.

In traditional ethanol production by fermentation, the plant material used is 6-carbon sugar, either directly extracted from plants containing free monosaccharides or disaccharides, or generated by the hydrolysis of starch from starch containing plant parts. These sugars are from plant parts that are also used for human or for animal consumption. Traditional ethanol production is, therefore, competing directly for plant material which would otherwise be used for food or feed. The conversion of food into fuel raises ethical concerns in a world where millions of people are starving; calculations show that the amount of corn necessary to produce a tank-full of fuel for one very common off-roader type car in the USA is approximately the amount needed to feed one otherwise starving person for one full year.

An alternative solution is to use lignocellulosic plant material that is otherwise regarded as waste for generation of energy and fuel. This is, in general, regarded in a very positive way, and the development of ways to use lignocellulosic plant material for ethanol production has, therefore, in many countries attracted strong support, both politically and by the general public. Another advantage is the abundance of lignocellulosic material, actually making the substitution of 50% or more of the current gasoline consumption with ethanol theoretically feasible.

There are numerous sources of lignocellulosic material that may be used for ethanol production—provided that an efficient and economical collection and conversion process can be established. A few examples, where the collection is already being done today, include sugar cane bagasse, wood chips, corn stover and wheat straw.

The two primary technical problems encountered in the use of lignocellulosic material for ethanol production through fermentation are:

1. the difficulties in hydrolysing the 6-carbon sugar containing cellulose into glucose without generating side-products that hamper or prevent further microbial conversion of the glucose into ethanol; and
2. the lack of an organism that is capable of efficient conversion of 5-carbon sugars (e.g. xylose and arabinose) present in the hemicellulose part of the lignocellulosic material into ethanol.

*Saccharomyces cerevisiae* has for more than 6000 years been the preferred microorganism for conversion of 6-carbon sugars derived from plant material into ethanol. This is due to a favourable combination of high ethanol yield, high specific productivity and high ethanol tolerance together with the ability to grow and ferment at low pH, where other competing microorganisms have trouble just surviving. When the difficulties in cellulose hydrolysis has been overcome, then *S. cerevisiae* will most likely continue to be the preferred organism to be used for generating ethanol by fermentation of the released 6-carbon sugar monomers. But, unfortunately, *S. cerevisiae* is unable to metabolize 5-carbon sugars that constitute up to one-third of the lignocellulosic sugar material.

Work has consequently been made during the last two decades to seek ways to genetically engineer *S. cerevisiae* in order to introduce 5-carbon sugar fermenting capacity. This work has primarily focused on xylose fermentation, as xylose constitutes the dominant part of 5-carbon sugars in lignocellulose. Although *S. cerevisiae* cannot metabolize xylose, it is capable of metabolizing the isomer xylulose (Wang and Schneider, 1980), which is the metabolite constituting an entry point into the pentose phosphate pathway. So in principle, the problem can be solved by providing *S. cerevisiae* with the ability to convert xylose into xylulose.

Two different, existing biochemical pathways have been successfully introduced into *S. cerevisiae* in order to channel xylose into the pentose phosphate pathway through xylulose. In natural xylose-metabolizing fungi, xylose is converted into xylulose in a two-step process (see FIG. 1). Xylose is first reduced to xylitol by a xylose reductase (XR-EC 1.1.1.21). Xylitol is then dehydrogenated to xylulose by xylitol dehydrogenase (XDH-EC 1.1.1.9). The reductase and the dehydrogenase are not present in *S. cerevisiae*, but it has been possible to transfer and express genes encoding those two enzymes from *Pichia stipitis* into *S. cerevisiae*, and the resulting, modified *S. cerevisiae* strain is able to metabolize xylose.

The activity of the two enzymes requires NADPH and NAD+ and generates NADP+ and NADH, so it is necessary for the organism to regenerate the NAD+-NADH and the NADP+-NADPH balance by redox processes elsewhere in the metabolism, otherwise the xylose metabolism will cease to function when NADPH and NAD+ has been depleted. A fairly low rate of xylose metabolism and the generation of significant amounts of xylitol by *S. cerevisiae* strains modified this way has been attributed to this inherent problem in the xylose reductase-xylitol dehydrogenase pathway.

In xylose metabolizing bacteria, conversion of xylose into xylulose is different: a single enzyme, xylose isomerase (EC 5.3.1.5), converts xylose directly into xylulose (see FIG. 1). This appears to be simpler, and it does not generate the NAD+-NADPH imbalance as mentioned above. It was therefore also the first strategy to be proposed for conferring xylose metabolism ability into *S. cerevisiae*. But it has proven difficult to make this strategy work. Expression of most xylose isomerase genes from bacteria does not result in the presence of an active xylose isomerase in *S. cerevisiae*, and the exact reason for this is still not known. Various studies have revealed that often a protein produced from expression of a bacterial gene can be detected, but the expressed protein apparently fails to fold into an active enzyme in *S. cerevisiae*.

Heat stable enzymes are often also more stable in other types of extreme conditions, such as high salt and extreme pH values. This may indicate that heat stable enzymes are more likely to maintain (and probably also to obtain) a correct fold. And it has indeed been possible to find examples of bacterial xylose isomerase genes isolated from thermophilic organisms that express active xylose isomerases in *S. cerevisiae* (see: Walfridsson et al, 1996; and Bao et al, 1999). These genes have been shown to enable *S. cerevisiae* to metabolize xylose, but at a very low rate. The low rate has been attributed to the fact that the heat-stable xylose isomerases has an optimal activity at 80-90° C. but the temperatures that permit the survival of most *S. cerevisiae* strains are 30-35° C.

STATEMENTS OF THE INVENTION

The present invention relates to a transformed microorganism capable of:
(a) a higher xylose isomerase activity than the equivalent microorganism prior to transformation; and/or
(b) a higher growth rate in or on a growth medium comprising xylose than the equivalent microorganism prior to transformation; and/or
(c) a faster metabolism of xylose than the equivalent microorganism prior to transformation; and/or
(d) a higher production of ethanol when grown anaerobically on xylose as the carbon source than the equivalent microorganism prior to transformation.

In another aspect, the present invention relates to an inoculum comprising a microorganism according to the present invention.

The present invention relates to, in another aspect, a culture medium comprising a microorganism according to the present invention.

In a further aspect, the present invention relates to a method for preparing a transformed microorganism, said method comprising the step of transforming a microorganism such that said transformed microorganism is capable of:
(a) a higher xylose isomerase activity than the microorganism prior to transformation; and/or
(b) a higher growth rate in or on a growth medium comprising xylose than the microorganism prior to transformation; and/or
(c) a faster metabolism of xylose than the microorganism prior to transformation; and/or
(d) a higher production of ethanol when grown anaerobically on xylose as the carbon source than the microorganism prior to transformation.

In another aspect, the present invention relates to a fermentation method comprising culturing in a culture medium a microorganism according to the present invention or a microorganism prepared by the method of the present invention.

The present invention provides, in a further aspect, a method for producing a product derived from xylose comprising culturing in a culture medium a microorganism according to the present invention or a microorganism prepared by the method of the present invention.

The present invention provides, in another aspect, a method for producing a biofuel wherein said method comprises the step of culturing in a culture medium a microorganism of the present invention or a microorganism prepared by the method of the present invention.

There is provided, in another aspect of the present invention, a biofuel obtained by a method of the present invention.

There is provided, in a further aspect of the present invention, a product derived from xylose obtained by a method of the present invention.

There is provided in a further aspect of the present invention, the use of a microorganism according to the present invention or a microorganism prepared by the method of the present invention for the production of a product derived from xylose.

Further, the present invention provides the use of a microorganism according to the present invention or a microorganism prepared by the method of the present invention for the production of a biofuel.

In another aspect, the present invention provides a transformed microorganism wherein said transformed microorganism comprises an exogenous nucleotide sequence encoding a xylose isomerase.

DISCUSSION

Figure 4:
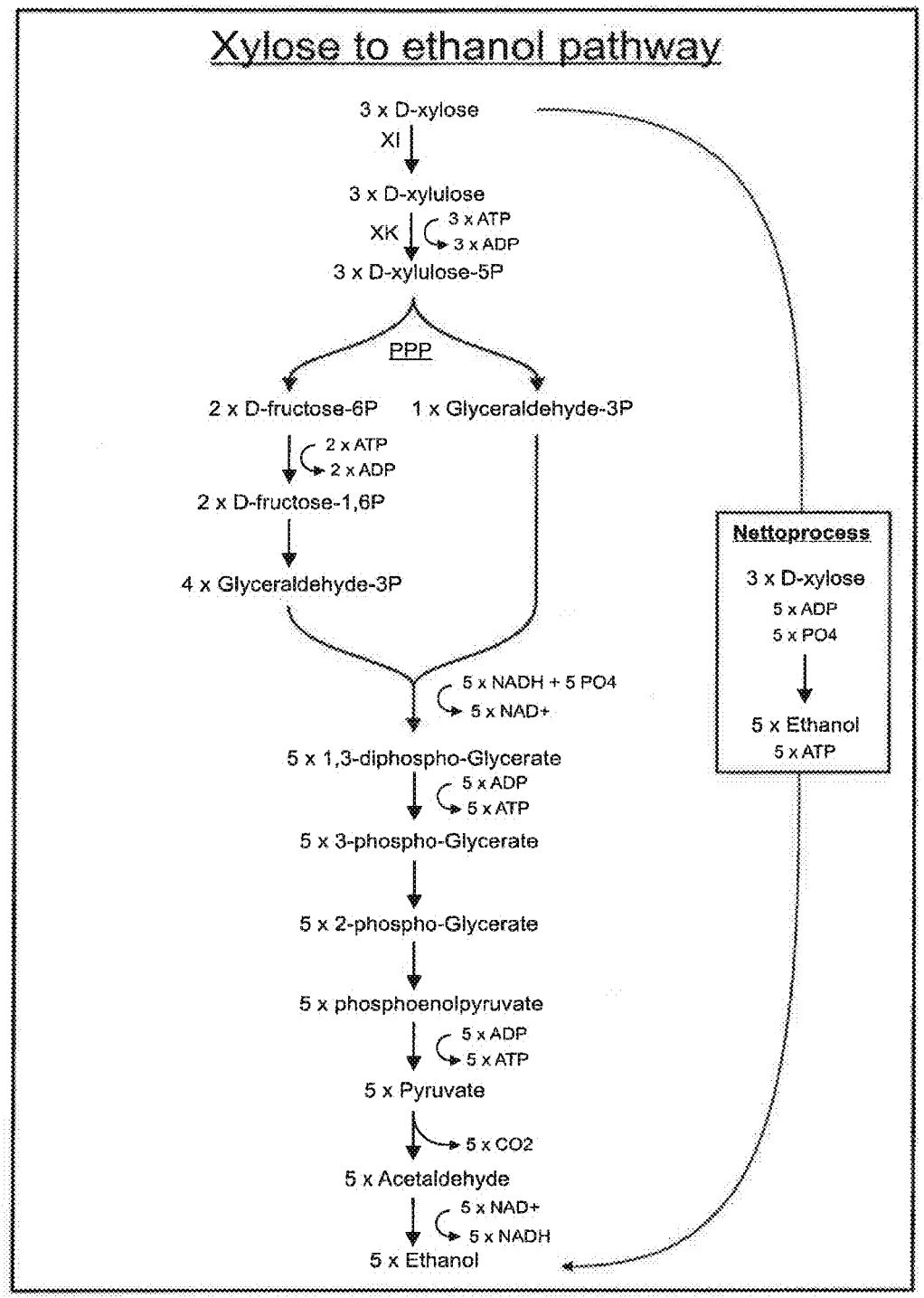

Earlier efforts to find bacterial xylose isomerase genes of mesophilic origin with high activity when expressed in, for example, *Saccharomyces cerevisiae* have been unsuccessful. Unexpectedly, as disclosed herein, the inventors have now succeeded in identifying bacteria, in particular mesophilic bacteria, that contain nucleotide sequences encoding xylose isomerase which upon expression in, for example, *S. cerevisiae*, give rise to a high intracellular xylose isomerase activity in the organism. Such sequences may be used, for example, to engineer strains of the *Saccharomyces* family to enable the yeast to convert xylose into xylulose and thereby facilitate the efficient production and/or metabolism of xylose into ethanol. FIG. 4 details the metabolism of xylose into ethanol; xylulose-5-phosphate—an intermediate which may be derived from D-xylose—enters into the pentose phosphate pathway and is further metabolized into ethanol under anaerobic conditions. But in addition to that, such sequences may also be used to engineer strains of, for example, *S. cerevisiae* to be efficient producers of other compounds derived from xylose through the pentose phosphate pathway. Examples of such compounds include, but are not limited to, aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene.

SOME ADVANTAGES

Advantageously, the present invention relates to the transformation (engineering) of microorganisms, such as those of the *Saccharomyces* family, to enable the microorganisms to metabolise xylose. This, in turn, advantageously increases the efficiency of the microorganisms—in particular *Saccharomyces* strains—to produce ethanol from xylose-containing feedstock (such as lignocellulosic material). In addition, it advantageously increases the efficiency of microorganisms to produce other natural or engineered metabolites derived from intermediates in the pentose phosphate pathway such as aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene. Further, it facilitates the general use of xylose-containing material as feedstock for the growth of strains of the *Saccharomyces* family for industrial purposes.

A further advantage is that the nucleotide sequence encoding xylose isomerase is derived from a mesophilic organism and/or is capable of high activity at mesophilic temperatures.

Another advantage is that the microorganisms according to the present invention produce an active xylose isomerase.

Advantageously, by using the microorganisms according to the present invention, biofuels (such as ethanol) can be produced.

More advantageously, by using the microorganisms according to the present invention, biofuels can be produced from waste materials such as agricultural wastes (including cereal straw—such as wheat straw; sugar beet pulp; sugar cane bagasse; stovers—such as sorghum, Soya beans, maize or corn stovers; and wood chips). With the present invention there is no need (or there is a reduced need) to use materials (such as sugar cane extract, sugar beet extract, sorghum starch, maize starch, wheat starch or corn starch) which could otherwise be used as a food source for humans and/or as an animal feed.

Advantageously, the microorganisms according to the present invention enable the optimum use of the sugars released by hydrolysis of lignocellulosic material by the fermentation of pentose sugars—in particular xylose.

The present invention enables the production of a biofuel which is more $CO_2$ neutral in comparison with petroleum based transportation fuel. With the present invention, $CO_2$ emissions will be low (even lower) when producing the biofuel according to the present invention than compared to the production of a typical petroleum based transportation fuel (fossil fuels).

FIGURES

FIG. 1. A schematic representation of the metabolic pathways detailing the metabolism of the two aldopentoses, D-xylose and L-arabinose. Both aldopentoses are converted into a ketopentose, and further into D-xylulose 5-phosphate. Without wishing to be bound by theory, as indicated on the figure, one type of pathway (aldose reductase type) is found in fungi whereas the other type of pathway (isomerase type) is found in bacteria. In the fungal pathway type, the first enzymes may be called "D-xylose reductase" and "L-arabinose reductase", but often the same enzyme can reduce both D-xylose and L-arabinose and may then serve both pathways and be referred to by the less specific name "aldose reductase".

Figure 2:
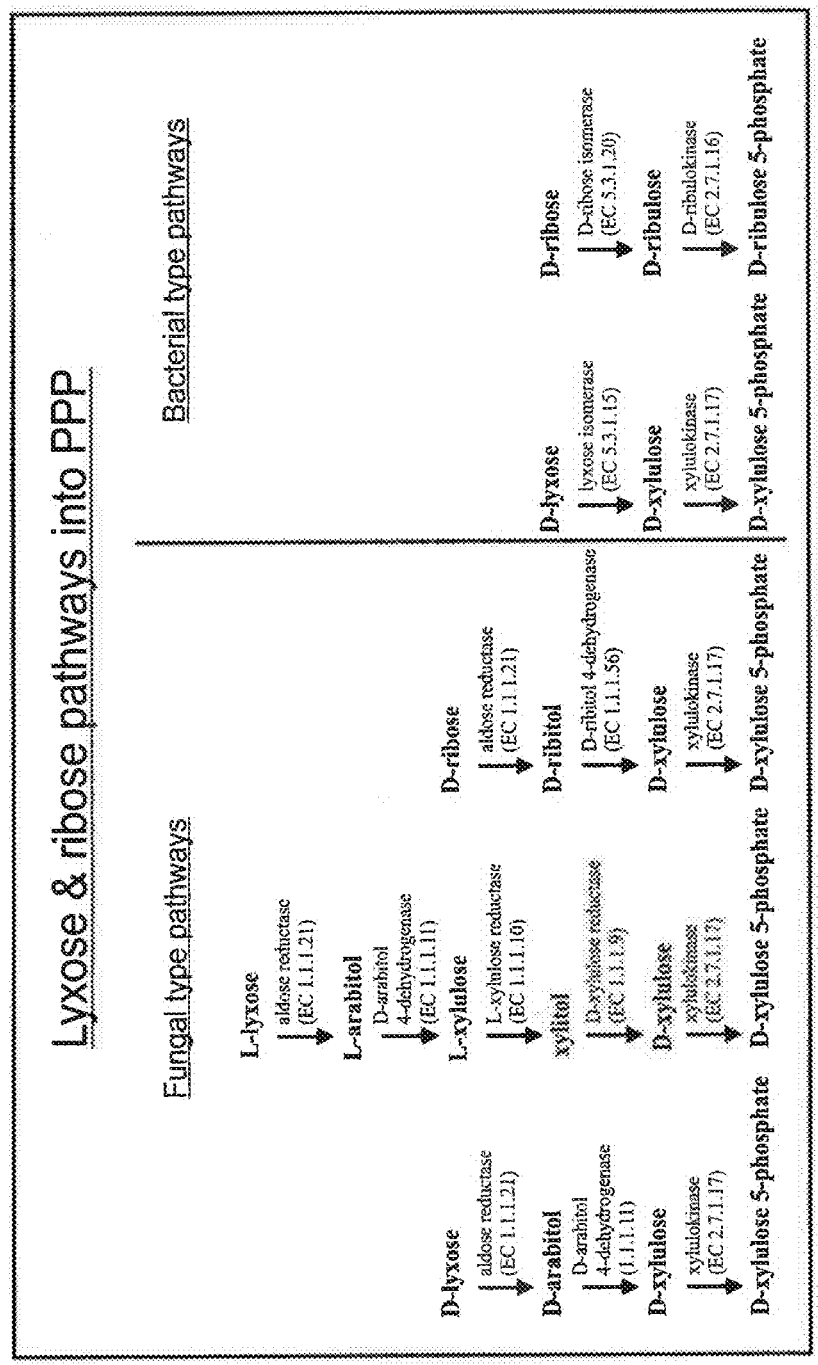

FIG. 2. Without wishing to be bound by theory, FIG. 2 shows a schematic representation of fungal and bacterial types of metabolic pathways of some less abundant pentoses (D- and L-lyxose, D-ribose) detailing the initial metabolism until the entry into the pentose phosphate pathway.

Figure 3:
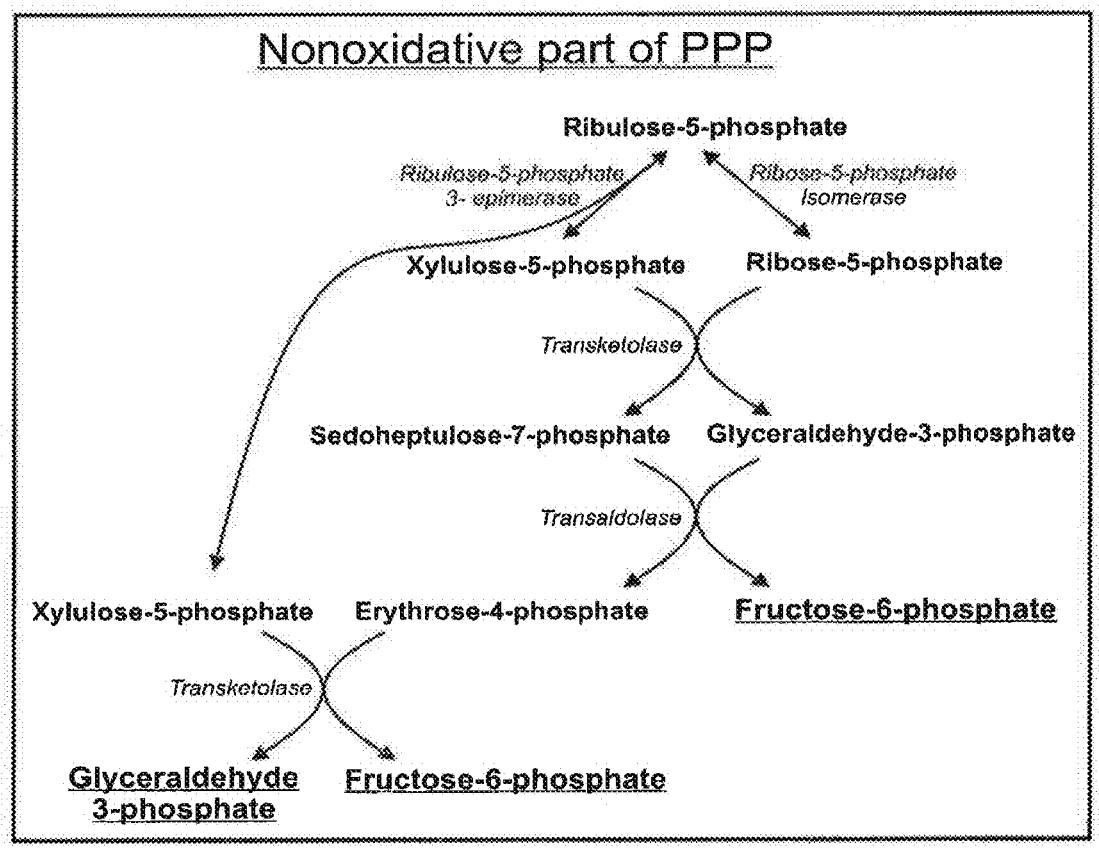

FIG. 3. A schematic representation of the non-oxidative part of the pentose phosphate pathway (PPP).

FIG. 4. A schematic representation of the metabolic conversion of xylose into ethanol. Here, ketopentose xylulose-5-phosphate, which may be derived from D-xylose, is further metabolized into ethanol under anaerobic conditions. XI is xylose isomerase and XK is xylulokinase. The net input of xylose into the process and the net output of ethanol from the process is shown (nettoprocess).

Figure 5:
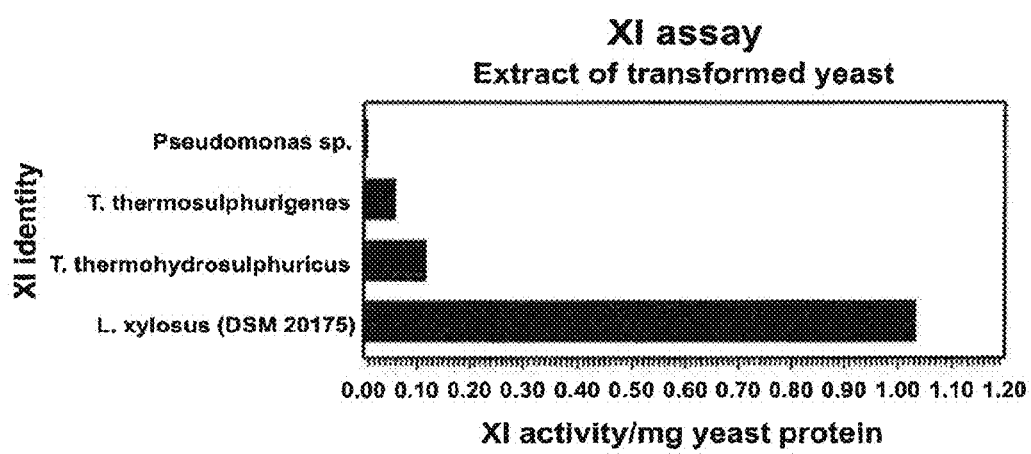

FIG. 5. Xylose isomerase (XI) activity in *Saccharomyces cerevisiae* transformed with a nucleotide sequence encoding a bacterial xylose isomerase. The bacterial xylose isomerase is derived from (i) *Pseudomonas syringae*, (ii) *Thermoanaerobacter thermohydrosulfuricus*, (iii) *Thermoanaero-*

*bacter thermohydrosulfurigenes* or (iv) *Lactococcus lactis* subsp. *lactis* (*Lactobacillus xylosus*).

Figure 6:
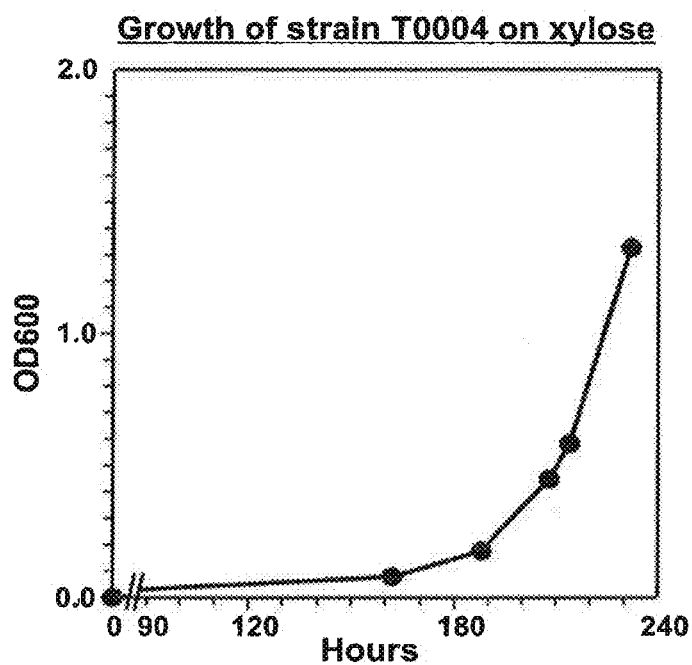

FIG. 6. The growth on xylose of *Saccharomyces cerevisiae* transformed with a nucleotide sequences encoding and expressing a bacterial xylose isomerase and a nucleotide sequence encoding and expressing a xylulose kinase cloned from *Pichia stipitis*.

Figure 7:
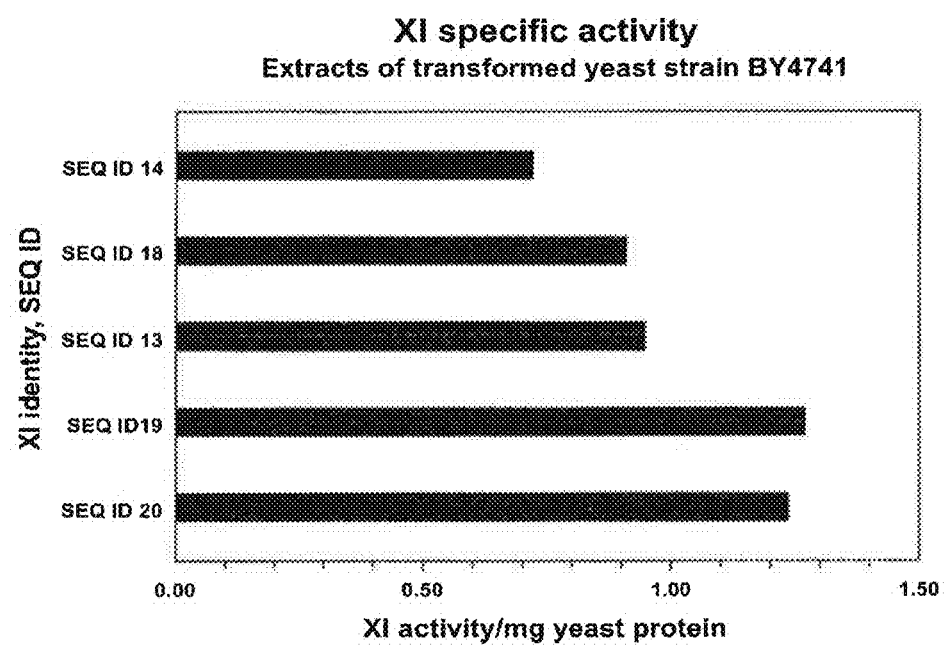

FIG. 7. The specific xylose isomerase activity of *Saccharomyces cerevisiae* transformed with a nucleotide sequence encoding and expressing a variant *Lactococcus* xylose isomerase. The variant *Lactococcus* xylose isomerase (XI) has the amino sequence SEQ ID No 14, SEQ ID No 18, SEQ ID No 13, SEQ ID No 19 or SEQ ID No 20.

DESCRIPTION OF THE INVENTION

As used herein the phrases "a higher xylose isomerase activity than the equivalent microorganism prior to transformation" and "a higher xylose isomerase activity than the microorganism prior to transformation" refer to a transformed microorganism which has an xylose isomerase activity of at least 0.16, 0.2, 0.4, 0.5, 0.6, 0.7, 0.8, 0.9 or 1.0 xylose isomerase units per mg microorganism protein, when cultured under suitable culture conditions permitting at least the maintenance of said microorganism; for instance, said culture medium may comprise one or more substrates (e.g. xylose) capable of activating the expression of the nucleotide sequence encoding the xylose isomerase but said culture medium does not comprise any substrate which is capable of inhibiting the expression of the nucleotide sequence encoding the xylose isomerase. One example of suitable culture conditions is described in Example 5. Said xylose isomerase activity is measured using the cysteine-carbazole assay described by Dische and Borenfreund (1951). The xylose isomerase activity of the transformed microorganism is higher than that of the equivalent microorganism prior to transformation, or the microorganism prior to transformation, when cultured under the same culture conditions as the transformed microorganism.

As used herein the phrases "a higher growth rate in or on a growth medium comprising xylose than the equivalent microorganism prior to transformation" and "a higher growth rate in or on a growth medium comprising xylose than the microorganism prior to transformation" refer to a transformed microorganism capable of an increased rate of growth such that the time taken for a doubling in the number of microorganisms is at least 10%, 15%, 20% or 25% lower than that of the equivalent microorganism prior to transformation, or the microorganism prior to transformation, when cultured under the same conditions.

The phrases "a faster metabolism of xylose than the equivalent microorganism prior to transformation" and "a faster metabolism of xylose than the equivalent microorganism prior to transformation", as used herein, refer to a transformed microorganism which is capable of metabolising xylose such that the consumed amount of xylose in the culture medium is at least 10%, 20%, 25%, 30% or 35% higher per cell than that of the equivalent microorganism prior to transformation, or the microorganism prior to transformation, when cultured under the same conditions for a given time period within the exponential growth phase. Said transformed microorganism is cultured under suitable culture conditions permitting at least the maintenance of said microorganism; for instance, said culture medium may comprise one or more substrates (e.g. xylose) capable of activating the expression of the nucleotide sequence encoding the xylose isomerase but said culture medium does not comprise any substrate which is capable of inhibiting the expression of the nucleotide sequence encoding the xylose isomerase.

As used herein the phrases "a higher production of ethanol when grown anaerobically on xylose as the carbon source than the equivalent microorganism prior to transformation" and "a higher production of ethanol when grown anaerobically on xylose as the carbon source than the microorganism prior to transformation" refer to a transformed microorganism which is capable of producing at least 10%, 20% or 30% more ethanol per cell than that of the equivalent microorganism prior to transformation when cultured under anaerobic conditions, with xylose as the carbon source, for a given time period.

The term "equivalent microorganism prior to transformation" as used herein includes references to the microorganism prior to transformation with a nucleotide sequence that encodes xylose isomerase or prior to transformation with a nucleotide sequence that causes the upregulation (e.g. overexpression) of xylose isomerase.

In one embodiment the microorganism according to the present invention has been transformed with a nucleotide sequence that causes the microorganism to overexpress xylose isomerase. For example, a promoter is inserted into the genome of a microorganism which enables the microorganism to overexpress an endogenous nucleotide sequence encoding xylose isomerase.

In another embodiment the microorganism according to the present invention has been transformed with a nucleotide sequence encoding xylose isomerase. For example, the microorganism is transformed with an expression vector comprising a nucleotide sequence encoding xylose isomerase operably linked to a regulatory sequence.

Preferably, the microorganism according to the present invention has been transformed with a nucleotide sequence encoding a xylose isomerase.

Preferably, the microorganism according to the present invention has been transformed with a nucleotide sequence encoding an exogenous xylose isomerase.

Preferably, the microorganism according to the present invention has been transformed with a nucleotide sequence encoding an exogenous xylose isomerase derived from a *Lactococcus* species.

In a preferred embodiment, the microorganism according to the present invention has been transformed with a nucleotide sequence encoding the amino acid sequence shown as SEQ ID No 14, SEQ ID No 11, SEQ ID No 18, SEQ ID No 13, SEQ ID No 19 or SEQ ID No 20, or a variant, homologue or derivative thereof.

In a more preferred embodiment, the microorganism according to the present invention has been transformed with a nucleotide sequence encoding the amino acid sequence shown as SEQ ID No 19 or SEQ ID No 20, or a variant, homologue or derivative thereof.

In a preferred embodiment, the microorganism according to the present invention has been transformed with the nucleotide sequence shown as SEQ ID No 1, SEQ ID No 10, SEQ ID No 17, SEQ ID No 12, SEQ ID No 27 or SEQ ID No 28, or a variant, homologue or derivative thereof.

In a more preferred embodiment, the microorganism according to the present invention has been transformed with the nucleotide sequence shown as SEQ ID No 27 or SEQ ID No 28, or a variant, homologue or derivative thereof.

In one aspect, the microorganism according to the present invention has been transformed with two or more nucleotide sequences encoding xylose isomerase.

Preferably the nucleotide sequence encoding xylose isomerase mentioned herein is in an expression vector encoding same.

Preferably the expression vector mentioned herein comprises a promoter capable of overexpressing the nucleotide sequence encoding xylose isomerase. Examples of such promoters include the GPD promoter, the TEF promoter and the ADP promoter. Preferred promoters which may be used to overexpress xylose isomerase can be any of the regulatory elements controlling the expression of nucleotide sequences encoding proteins involved in glycolysis and glucose fermentation.

In one embodiment, in the method according to the present invention, the microorganism is transformed with a nucleotide sequence that causes the microorganism to overexpress xylose isomerase. For example, a promoter is inserted into the genome of a microorganism which enables the microorganism to overexpress an endogenous nucleotide sequence encoding xylose isomerase. In a further example, a promoter is inserted into the genome of a microorganism which enables the microorganism to constitutively express an endogenous nucleotide sequence encoding xylose isomerase.

In another embodiment in the method according to the present invention, the microorganism is transformed with a nucleotide sequence encoding xylose isomerase. For example, the microorganism is transformed with an expression vector comprising a nucleotide sequence encoding xylose isomerase operably linked to a regulatory sequence. In a further example, the microorganism is transformed with an expression vector comprising a nucleotide sequence encoding xylose isomerase operably linked to a regulatory sequence wherein said regulatory sequence enables the constitutive expression of the nucleotide sequence encoding xylose isomerase.

Preferably, in the method according to the present invention, the microorganism is transformed with a nucleotide sequence encoding a xylose isomerase.

Preferably, in the method according to the present invention, the microorganism is transformed with a nucleotide sequence encoding an exogenous xylose isomerase.

In a preferred embodiment, in the method according to the present invention the microorganism is transformed with a nucleotide sequence, encoding a xylose isomerase, comprising the nucleotide sequence shown as SEQ ID No 1, SEQ ID No 10, SEQ ID No 17, SEQ ID No 12, SEQ ID No 27 or SEQ ID No 28, or a variant, homologue or derivative thereof.

In a preferred embodiment, in the method according to the present invention the microorganism is transformed with a nucleotide sequence encoding a xylose isomerase comprising the amino acid sequence shown as SEQ ID No 14, SEQ ID No 11, SEQ ID No 18, SEQ ID No 13, SEQ ID No 19 or SEQ ID No 20, or a variant, homologue or derivative thereof.

In one aspect, in the method according to the present invention, the microorganism is transformed with two or more nucleotide sequences encoding xylose isomerase.

In the method according to the present invention, preferably the nucleotide sequence encoding a xylose isomerase is in an expression vector encoding same.

As used herein the term "fermentation method" refers to culturing a microorganism or microorganisms under aerobic and anaerobic conditions.

In one embodiment, the culture medium comprises xylose and/or a source of xylose.

In one embodiment, the culture medium comprises a pentose sugar and/or a source of pentose sugar. Preferably, the pentose sugar is xylose. In one embodiment, the pentose sugar is derived and/or derivable from lignocellulosic material.

Alternatively, or in addition, the culture medium comprises material derived from lignocellulosic material.

Preferably, the method according to the present invention further comprises the step of obtaining the biofuel from the culture medium.

In one embodiment the product derived from xylose is selected from the group consisting of xylulose, xylulose-5-phosphate, ethanol, aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene.

Preferably, the product derived from xylose is selected from the group consisting of xylulose, xylulose-5-phosphate, ethanol, aromatic amino acids, lactic acid, succinic acid, acetic acid, acetaldehyde, furfural, itaconic acid, glutamic acid, citric acid, cresol, lysine, 3-hydroxypropionic acid and poly-3-hydroxyalkanoates.

In a highly preferred embodiment, the product derived from xylose is ethanol.

As used herein, the term "overexpress" in the phrase "a nucleotide sequence that causes the microorganism to overexpress xylose isomerase" and "a promoter capable of overexpressing the nucleotide sequence encoding xylose isomerase" refers to an increase in expression from zero to a level of expression or going from a lower level of expression to a higher level of expression (e.g. upregulation) when the transformed microorganism is compared to the equivalent microorganism prior to transformation. Microorganisms overexpressing xylose isomerase have an increased ability to catalyse the conversion of xylose to xylulose. The ability to convert xylose to xylulose may be confirmed by determining the ability of cell lysate to produce xylulose from xylose by assaying the produced xylulose using, for example, a ketopentose assay as described by Dische and Borenfreund (Dische and Borenfreund, 1951), also described in the example section herein.

Preferably the transformed microorganism which overexpresses xylose isomerase is capable of:
 (a) a higher xylose isomerase activity than the equivalent microorganism prior to transformation; and/or
 (b) a higher growth rate in or on a growth medium comprising xylose than the equivalent microorganism prior to transformation; and/or
 (c) a faster metabolism of xylose than the equivalent microorganism prior to transformation; and/or
 (d) a higher production of ethanol when grown anaerobically on xylose as the carbon source than the equivalent microorganism prior to transformation.

Examples of microorganisms overexpressing xylose isomerase include: (i) microorganisms transformed with an expression vector encoding xylose isomerase (prior to transformation said microorganism was not capable of expressing xylose isomerase); and (ii) microorganisms transformed to upregulate the expression of an endogenous xylose isomerase (prior to transformation said microorganism was capable of expressing said xylose isomerase for a given set of culture conditions during exponential growth but after transformation said microorganism is capable of expressing said xylose isomerase at a higher level, in the same culture conditions, during exponential growth).

The term "a nucleotide sequence encoding xylose isomerase" as used herein encompasses nucleotide sequences comprising regulatory sequences enabling the expression of the nucleotide sequence encoding xylose isomerase such as promoters and enhancers which may be natively or non-natively associated with the nucleotide sequence encoding xylose isomerase.

In one aspect, the present invention provides a genetically modified yeast cell having a functional exogenous xylose isomerase gene derived from a microorganism of the *Lactococcus* family, wherein the exogenous xylose isomerase gene is operatively linked to promoter and terminator sequences that are functional in the yeast.

In another aspect, the present invention provides a fermentation process in which a microorganism as described herein is cultured under fermentation conditions in a fermentation broth that includes material derived from lignocellulosic material.

In yet another aspect, the present invention provides a fermentation process utilising a microorganism according to the present invention wherein the fermentation broth (i.e. the culture medium) comprises a pentose sugar.

Transformed Microorganism

As mentioned herein, the term "transformed microorganism" refers to a microorganism that has been genetically altered by recombinant DNA technology. The term "transformed" as used herein is synonymous with terms such as "transfected", "recombinant", "genetically engineered" and "genetically modified".

The term "transformed microorganism" in relation to the present invention includes any microorganism that comprises an expression vector(s) comprising the nucleotide sequence(s) mentioned herein and/or a promoter(s) that is capable of allowing the expression (in particular overexpression i.e. upregulation) of the nucleotide sequence(s) mentioned herein. In one embodiment the nucleotide sequence(s) is incorporated in the genome of the microorganism. In another embodiment, the promoter is incorporated in the genome of the microorganism. These features enable the transformed microorganism (when compared to equivalent microorganism prior to transformation) to have (a) a higher xylose isomerase activity; and/or (b) a higher growth rate in or on a growth medium comprising xylose; and/or (c) a faster metabolism of xylose; and/or (d) a higher production of ethanol when grown anaerobically on xylose as the carbon source.

The term "transformed microorganism" does not cover native nucleotide coding sequences in their natural environment when they are under the control of their native promoter which is also in its natural environment.

Therefore, the transformed microorganism of the present invention includes a microorganism comprising any one of, or combinations of, the nucleotide sequences coding for the enzymes mentioned herein, constructs comprising said nucleotide sequences, vectors comprising said nucleotide sequences, plasmids comprising said nucleotide sequences and expression vectors comprising said nucleotide sequences.

Thus, a further embodiment of the present invention provides microorganisms transformed or transfected with a nucleotide sequence(s) that expresses the enzyme(s) mentioned herein. The microorganism will be chosen to be compatible with the vector and may be, for example, bacterial, fungal or yeast cells.

Examples of suitable bacterial host organisms are gram positive or gram negative bacterial species.

Depending on the nature of the nucleotide sequence(s) encoding the enzyme(s) mentioned herein, eukaryotic hosts such as yeasts or other fungi may be preferred. In general, yeast cells are preferred over fungal cells because they are easier to manipulate.

The use of suitable microorganisms—such as yeast and fungal host cells—may provide for post-translational modifications (e.g. myristoylation, glycosylation, truncation, lipidation and tyrosine, serine or threonine phosphorylation) as may be needed to confer optimal biological activity on recombinant expression products mentioned herein.

Suitable microorganisms include bacteria, fungi and yeasts. Preferably the microorganism is a yeast.

Preferably said transformed microorganism is a transformed yeast. Preferably said transformed yeast is derived from the genus *Saccharomyces*. More preferably said transformed yeast is *Saccharomyces cerevisiae*.

In one embodiment, the transformed microorganism described herein is capable of a higher xylose isomerase activity than the equivalent microorganism prior to transformation.

In another aspect, the transformed microorganism described herein is capable of a higher growth rate in or on a growth medium comprising xylose than the equivalent microorganism prior to transformation.

In a further aspect, the transformed microorganism described herein is capable of a faster metabolism of xylose than the equivalent microorganism prior to transformation.

In another aspect, the transformed microorganism described herein is capable of a higher production of ethanol when grown anaerobically on xylose as the carbon source than the equivalent microorganism prior to transformation.

The microorganism may be transformed using techniques which are routine in the art such as electroporation (Sambrook et al 1989). Further, the presence of a sequence in a transformed microorganism may be determined by growth selection on suitable media which select for the growth of the transformed microorganism. Alternatively or in addition, the presence of inserted, heterologous DNA sequences may be determined by direct colony PCR using primers specifically designed for the inserted sequence. Such techniques are well known and routine in the art (see, for example, Sambrook et al 1989 and Ausubel et al 1995).

The transformed microorganisms according to the present invention may be used in combination with one or more further microorganisms. For example, one or more transformed microorganisms according to the present invention may cultured in combination with at least one microorganism capable of producing, under certain culture conditions, one of more components selected from the list consisting of: ethanol, aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene.

In a further aspect, there is provided a combination of (i) one or more transformed microorganisms according to the present invention and (ii) at least one further microorganism capable of producing, under certain culture conditions, one of more components selected from the list consisting of: ethanol, aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene.

Additionally, the present invention provides an inoculum comprising a combination of a transformed microorganism according to the present invention and one or more further microorganisms.

Further, there is provided a culture medium comprising a combination of a transformed microorganism according to the present invention and one or more further microorganisms.

In addition, the present invention provides a kit comprising an inoculum comprising one or more microorganisms according to the present invention.

In addition, the present invention provides a kit comprising (i) an inoculum comprising one or more microorganisms according to the present invention and (ii) an inoculum comprising one or more further microorganisms.

Transformed Yeast

In a preferred embodiment, the transgenic microorganism is a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

Expression Vector

The term "expression vector" means a construct capable of in vivo or in vitro expression.

In one aspect, the expression vector is incorporated into the genome of a suitable microorganism. The term "incorporated" preferably covers stable incorporation into the genome.

The nucleotide sequences mentioned herein may be present in a vector in which the nucleotide sequence is operably linked to regulatory sequences capable of providing for the expression of the nucleotide sequence by a suitable host microorganism.

The vectors are transformed into a suitable host microorganism as described herein.

The choice of vector e.g. a plasmid, cosmid, or phage vector will often depend on the microorganism into which it is to be introduced.

The vectors for use herein may contain one or more selectable marker nucleotide sequences—such as a nucleotide sequence which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example to transfect, transform, transduce or infect a host microorganism.

The vector may further comprise a nucleotide sequence enabling the vector to replicate in the host microorganism in question. Examples of such sequences are the origins of replication of plasmids pUC19, pACYC177, pUB110, pE194, pAMB1 and pIJ702.

In a preferred aspect, the microorganism capable of converting xylose to xylulose as mentioned herein comprises a nucleotide sequence encoding xylose isomerase.

Preferably an expression vector as mentioned herein comprises a nucleotide sequence encoding xylose isomerase.

In a further aspect, preferably the microorganism capable of converting xylose to xylulose as mentioned herein comprises at least one expression vector encoding xylose isomerase.

Preferably, in another aspect, the microorganism capable of converting xylose to xylulose as mentioned herein may further comprise at least one expression vector encoding one or more enzymes selected from the group consisting of xylulokinase, D-ribulokinase, ribose-5-phosphate isomerase, ribulose-5-phosphate epimerase, transaldolase, transketolase and any other enzyme of the pentose phosphate pathway. More preferably, said microorganism capable of converting an aldopentose to a ketopentose as mentioned herein further comprises at least one expression vector encoding xylulokinase.

In one aspect, an expression vector as mentioned herein, may further encode one or more enzymes selected from the group consisting of an aldose-1-epimerase, xylose reductase, D-xylulose reductase, arabinose reductase, L-arabitol 4-dehydrogenase, L-xylulose reductase, L-arabinose isomerase, ribulokinase, ribulose phosphate 4-epimerase, D-lyxose isomerase, D-ribose isomerase, xylulokinase, D-ribulokinase, ribulose-5-phosphate epimerase, ribose-5-phosphate isomerase, transaldolase, and transketolase.

In one aspect, an expression vector as mentioned herein, may further encode one or more enzymes selected from the group consisting of aldose-1-epimerase, xylulokinase, D-ribulokinase, ribose-5-phosphate isomerase, D-ribulose-5-phosphate epimerase, transaldolase, transketolase and any other enzyme of the pentose phosphate pathway. Preferably, said expression vector as mentioned herein further encodes xylulokinase.

In a preferred aspect, the microorganism capable of converting xylose to xylulose as mentioned herein further comprises at least one expression vector encoding an aldose-1-epimerase.

Preferably an expression vector as mentioned herein further comprises a nucleotide sequence encoding an aldose-1-epimerase.

Regulatory Sequences

In some applications, the nucleotide sequence(s) mentioned herein is operably linked to a regulatory sequence which is capable of providing for the expression of the nucleotide sequence, such as by the chosen microorganism. By way of example, the present invention covers the use of a vector comprising the nucleotide sequence(s) mentioned herein operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

In one embodiment, the regulatory sequence enables the nucleotide sequence(s) operably linked to the regulatory sequence to be constitutively expressed in a host cell.

As used herein the terms "constitutively expressed" and "constitutive expression" refer to the continual transcription of a nucleotide sequence operably linked to the regulatory sequence (such as a constitutive promoter). Thus, for example, the culture medium does not need to comprise a substrate in order to activate the expression of the nucleotide sequence encoding the xylose isomerase. In another example, the culture medium could not comprise a substrate which inhibits the regulatory sequence and, therefore, inhibits the expression of the nucleotide sequence encoding the xylose isomerase.

The term "promoter" is used in the normal sense of the art, e.g. an RNA polymerase binding site.

Enhanced expression of the nucleotide sequence(s) encoding the enzyme(s) mentioned herein may also be achieved by the selection of heterologous regulatory regions, e.g. promoter, secretion leader and terminator regions.

Preferably, the nucleotide sequence(s) mentioned herein is operably linked to at least a promoter.

Other promoters may even be used to direct expression of the polypeptide(s) mentioned herein.

Examples of suitable promoters for directing the transcription of the nucleotide sequence in a bacterial, fungal or yeast cell are well known in the art.

The promoter can additionally include features to ensure or to increase expression in a suitable host. For example, the features can be conserved regions such as a Pribnow Box or a TATA box.

In one embodiment, the promoter enables the nucleotide sequence(s) operably linked to the promoter to be constitutively expressed in a host cell.

Constructs

The term "construct"—which is synonymous with terms such as "conjugate", "cassette" and "hybrid"—includes a nucleotide sequence mentioned herein directly or indirectly attached to a promoter.

An example of an indirect attachment is the provision of a suitable spacer group such as an intron sequence, such as the Sh1-intron or the ADH intron, intermediate the promoter and the nucleotide sequence(s) mentioned herein. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct comprises at least the nucleotide sequence(s) mentioned herein operably linked to a promoter.

Promoters

As mentioned herein, in one aspect the present invention relates to a microorganism that has been transformed with a nucleotide sequence, such as a promoter, that causes the microorganism to overexpress xylose isomerase.

For instance, the promoter is inserted into the genome of a microorganism which enables the microorganism to overexpress (e.g. upregulate) an endogenous nucleotide sequence encoding xylose isomerase.

In one embodiment, the promoter is inserted into the genome of a microorganism which enables the microorganism to constitutively express an endogenous nucleotide sequence encoding xylose isomerase.

In another aspect, the promoter is operably linked to a nucleotide sequence in, for example, an expression vector.

In one embodiment, the promoter enables the nucleotide sequence(s) operably linked to the promoter to be constitutively expressed in a host cell.

In another aspect, the promoter is not repressed by the presence of glucose.

Examples of suitable promoters that could be used in microorganisms according to the present invention, such as *Saccharomyces cerevisiae*, include: the promoter of the glyceraldehyde-3-phosphate dehydrogenase (GPD) gene; the promoter of the alcohol dehydrogenase (ADH) gene; and the promoter of the Thyrotrophic embryonic factor (TEF) gene.

Preferred promoters which may be used to overexpress xylose isomerase can be any of the regulatory elements controlling the expression of nucleotide sequences encoding proteins involved in glycolysis and glucose fermentation in yeast, in particular *Saccharomyces* such as *S. cerevisiae*. Examples of these are the glucokinase (GLK1) promoter, the phosphoglucose isomerase (PGI1) promoter, the phosphofructokinase (PFK1) promoter and the glyceraldehyde-3-phosphate dehydrogenase (TDH3) promoter.

Biofuel

As used herein, the term "biofuel" refers to a fuel (e.g. a liquid fuel) suitable for use in (for example) combustion engines. Said biofuel is derived from biological matter comprising pentose sugars and/or from which pentose sugars can be derived by hydrolysis by enzymatic means and/or by acidic treatment. Preferably said pentose sugar is the aldopentose xylose.

Plant materials—including plant waste comprising lignocellulosic material (for instance: cereal straw, such as wheat straw; sugar beet pulp; sugar cane bagasse; sorghum stover; Soya bean stover; maize stover; corn stover; wood-chips; and paper-pulp) and whole plants (such as those which are grown for energy purposes e.g. switchgrass)—are suitable sources for pentose sugars, in particular aldopentose sugars (such as xylose), for the present invention. Other suitable sources of plant material include non-waste products (in other words, food and feed sources) such as sugar cane extract, sugar beet extract, sorghum, Soya beans, wheat starch and corn starch.

Preferably the biofuel mentioned herein comprises at least one alcohol.

In a preferred aspect, the alcohol is selected from the group consisting of methanol, ethanol, propanol and butanol. More preferably the biofuel comprises ethanol.

Preferably, said biofuel is obtained (or obtainable)—in other words, extracted (or extractable)—from the culture medium in which one or more transformed microorganisms according to the present invention have been cultured under suitable conditions. Said biofuel may be obtained (or obtainable) from the culture medium using techniques which are routine in the art such as the removal of microorganism by centrifugation, isolation of the supernatant followed by distillation, and a further dehydration step to yield a 99.5% pure alcohol such as ethanol.

The biofuel may comprise one or more further biofuel components such as butanol.

The one or more further biofuel components may be admixed with the biofuel before and/or after the biofuel is obtained or extracted (obtainable or extractable) from a culture.

Alternatively or in addition, one or more further biofuel components may be produced by culturing a microorganism in a culture medium before and/or after and/or at the same time as a transformed microorganism according to the present invention is/has been cultured in a culture medium in order to produce the biofuel.

The present invention further provides a transportation fuel which comprises a biofuel produced using the microorganisms according to the present invention.

Ethanol used as a transportation fuel may serve two different purposes:
(i) it can act as an oxygenated additive that raises the octane value and reduces emission in ReFormulated Gasoline (RFG) (tetraethyl lead or MTBE replacement);
(ii) it can act as a partial or full substitute for Regular Gasoline (RG) to reduce dependency on gasoline supply.

Anhydrous ethanol has an octane value of 130, and can be added in concentrations of 5-10% (depending on the season) to Regular Gasoline obtained directly from refineries. Traditionally, tetra-ethyl lead has been used for octane boosting however, due to health issues, the use of lead has been banned almost worldwide. The addition of oxygenates to Regular Gasoline lowers the carbon monoxide emissions as well as other particles contributing to air pollution. Methyl tert-butyl ether (MTBE) was initially used as a oxygenate additive, however the occurrence of MTBE contamination in drinking water aquifers has prompted some states to ban the use of this oxygenate. Ethanol is increasingly used worldwide as a replacement for MTBE as an oxygenate additive for the manufacturing of RFG.

Apart from serving as an oxygenate additive in the production of ReFormulated Gasoline, ethanol can be used as a general substitute for regular gasoline. Cars can use E10 blends (10% added ethanol) without any modification of the engine.

Further, vehicles have been manufactured which can run on 100% ethanol—in other words, there is no requirement for a fossil based fuel.

The transformed microorganisms according to the present invention or the microorganisms prepared by a method according to the present invention are capable of producing a biofuel at a higher rate than the equivalent microorganism prior to transformation. As used here, the term "higher rate" refers to a transformed microorganism which is capable of producing in the culture medium at least 5%, 10%, 20%, 25%, 30% or 35% more biofuel (such as bioethanol) per cell than that of the equivalent microorganism prior to transformation when cultured under the same culture conditions for a given time period within the exponential growth phase.

Xylose Derived Product

As used herein, the term "xylose derived product" or "product derived from xylose" refers to any compound derived from xylose.

Examples of products derived from xylose include, but are not limited to: ethanol, aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene.

A product derived from xylose may be converted to another product. For example, the ketopentose D-xylulose, derived from the aldopentose D-xylose, may be converted via the pentose phosphate pathway into ethanol.

Preferably said product derived from xylose is one or more selected from the group consisting of ethanol, aromatic amino acids, lactic acid, succinic acid, acetic acid, acetaldehyde, furfural, itaconic acid, glutamic acid, citric acid, cresol, lysine, 3-hydroxypropionic acid, poly-3-hydroxyalkanoates, protocatechuic acid, pyrocatechol, guaiacol, veratrol, resveratrol, vanillin, vanillic acid, vanillyl alcohol, muconic acid, adipic acid, 4-hydroxybenzoic acid, 4-hydroxybenzaldehyde, 4-methoxybenzoic acid, 4-aminobenzoate, 4-hydroxyaniline, 4-methoxyaniline, quinol, anisole, phenol, anthranilic acid, 3-hydroxyanthranilate, 2,3-dihydroxybenzoic acid, 2-aminophenol, 1,4-cyclohexanedione, isoprene and styrene.

More preferably said product derived from xylose is ethanol.

Culture Medium

In one embodiment, the culture medium comprises xylose and/or a source of xylose.

In addition, the culture medium may comprise at least one further pentose. In a preferred aspect the culture medium further comprises at least one aldopentose.

Preferably the transformed microorganisms are grown in the optimal culture medium for said microorganism. Using routine techniques, the optimal culture medium can be determined; in addition, the optimal growth conditions can be determined.

In one embodiment, the culture medium comprises one or more substrates capable of activating the expression of a nucleotide sequence encoding the xylose isomerase in a microorganism according to the present invention but said culture medium does not comprise any substrate which is capable of inhibiting the expression of a nucleotide sequence encoding the xylose isomerase in a microorganism according to the present invention. For example: if the nucleotide sequence encoding the xylose isomerase comprises a xylose inducible promoter then the medium comprises xylose.

In one aspect said culture medium comprises about 1%, about 2%, about 4%, about 8%, about 15% or about 25% xylose before inoculation with the microorganism (i.e. at time zero).

Preferably said culture medium comprises the optimal amounts of salts, vitamins and other nutrients necessary for the microorganism.

The microorganisms are preferably cultured at their optimal growth temperature. The skilled person would have readily been able to determine the optimal temperature at which to culture microorganisms mentioned herein.

In one embodiment the microorganisms are cultured at about 20° C., 25° C., 30° C., 35° C., or 37° C.

In one embodiment the microorganisms are cultured at about 35° C. to 39° C., preferably about 36° C. to 38° C., more preferably at about 35.5° C. to 37.5° C.

In one embodiment the microorganisms are cultured for about 3 to 96 hours; preferably about 3 to 48 hours, about 3 to 24 hours, about 3 to 15 hours and about 3 to 6 hours.

Preferably the microorganisms are cultured for about 3 hours, about 6 hours, about 15 hours, about 24 hours, about 48 hours or about 96 hours.

In one aspect, the microorganism, in particular the transformed microorganism, is alcohol tolerant and/or acid tolerant.

The term "alcohol tolerant" in relation to the present invention refers to microorganisms which are capable of growth in a culture medium which comprises at least 2%, 5%, 10% or 15% alcohol.

As mentioned herein, the term "acid tolerant" refers to microorganisms which are capable of growth in a culture medium which has a pH equal to or less than 6.5, 6.0, 5.0, 4.0 or 3.0.

In a preferred aspect, the culture medium is inoculated with at least $5 \times 10^7$ to $5 \times 10^{11}$ cells per kg of culture medium, preferably $5 \times 10^8$ to $5 \times 10^{10}$ cells per kg of culture medium, preferably $1 \times 10^9$ to $1 \times 10^{10}$ cells per kg of culture medium and more preferably about $5 \times 10^9$ cells per kg of culture medium.

The terms "inoculum" and "starter culture" are interchangeable.

The culture conditions permit, at least, the maintenance of the microorganism according to the present invention or the microorganism prepared by a method according to the present invention. The culture conditions may optionally permit the growth of the microorganism according to the present invention or the microorganism prepared by a method according to the present invention.

Sources of Xylose

Xylose is an aldopentose. Xylose may be derived from: plant materials typically used as food or feed sources (such as: sugar cane, sugar beet, sorghum, wheat and corn—which are starch-rich and sugar-rich plant materials); whole plants (such as those which are grown for energy purposes e.g. switchgrass); and, in particular, waste agricultural (plant) materials (such as: cereal straw, for instance, wheat straw; sugar beet pulp; bagasse, for instance, sugar cane bagasse; stovers, for instance, sorghum, Soya bean, maize or corn stovers; and wood chips).

Sources of xylose for the culture medium described herein include lignocellulosic materials normally regarded as agricultural waste material. Stems, stalks and leaves contain lignocellulosic material and are, therefore, sources of lignocellulosic material. Sugar cane bagasses, corn stovers and wood chips (hemicellulose only) are three easily accessible sources of lignocellulosic material as these are already collected or stocked in large amounts for various reasons.

Lignocellulosic material consists primarily of long sugar chains. On average, two thirds of these sugars are hexose sugars, which are mainly present in cellulose, and one third of the sugars are pentose sugars present mainly in arabinoxylan polymers.

A significant amount of hemicellulose derived pentose sugar is xylose.

Lignocellulosic materials can be hydrolysed in order to release the hexose and/or pentose sugars in the long-chain sugars of the cellulose, hemicellulose and lignin.

Hydrolysis of lignocellulosic materials can be carried out by acidic treatment at elevated temperature. However, this treatment may generate sugar derived by-products that are toxic to the majority of microorganisms and prevent the conversion of the sugars to ethanol. Such toxic by-products (if generated) can be removed but this is generally uneconomical.

Alternatively, lignocellulosic materials can be hydrolysed using cellulose and hemicellulose hydrolyzing enzymes. Advantageously, this process avoids the generation of toxic side-products.

In a preferred aspect, the culture medium comprises material derived from one or more lignocellulosic materials which have been treated (examples of such treatment techniques include: steam treatment, steam explosion, wet oxidation, acid hydrolysis, alkaline wet oxidation and ammonia fibre expansion) to release xylose. Preferably the lignocellulosic material is treated by an enzymatic hydrolysis process. Said hydrolysed lignocellulosic material may be further treated in order to extract the sugars before the use of said extract in a culture medium.

Hydrolysis of Lignocellulosic Material

Initial Mechanical Treatment:

The lignocellulosic material is chopped into smaller pieces as and when deemed necessary. For example, wheat straw is cut into pieces of approximately 5 cm in length.

Subsequent Hydrothermal Pretreatment:

The hydrothermal pretreatment of the lignocellulosic material may be carried out as a steam pretreatment followed by a washing step, thereby producing a fibre fraction and a liquid fraction. The fibre fraction contains more than 90% of the cellulose, the lignin originally present in the cellulosic material, and some of the hemicelluloses. The liquid fraction contains sugars from the hemicelluloses (C5 sugars), more than 90% of alkali chlorides comprised in the lignocellulosic biomass, and the majority of fermentation inhibitors arising from pretreatment of lignocellulosic feedstock.

Typically, wheat straw is heated by steam to a temperature between 180 and 200° C. with a residence time of 5-15 min. The pretreated biomass is unloaded from the pressure reactor and washed and pressed. Released steam is collected and reused for evaporation of the liquid fraction to feed molasses.

Enzymatic Hydrolysis:

Subsequent hydrolysis of sugar polymers may be carried out by the addition of cellulases and hemicellulases, either prior to fermentation or during fermentation or both inter alia a simultaneous saccharification and fermentation process.

Hexose

Hexose sugars have 6 carbon atoms. Aldohexoses have an aldehyde at position 1, and ketohexoses having a ketone at position 2. Glucose is an example of an aldohexose. Fructose is an example of a ketohexose.

Pentose

Pentose sugars have 5 carbon atoms. Pentoses either have an aldehyde functional group in position 1 (aldopentoses) or a ketone functional group in position 2 (ketopentoses). Xylose, arabinose, ribose, lyxose, xylulose and ribulose are examples of pentoses.

Aldopentose

Xylose, arabinose, ribose and lyxose are examples of aldopentoses.

In one aspect, preferably said aldopentose is xylose.

Xylose may be L-xylose or D-xylose.

Preferably said xylose is D-xylose.

Ketopentose

Xylulose and ribulose are examples of ketopentoses.

In one aspect said ketopentose is xylulose or ribulose.

In one preferred aspect said ketopentose is xylulose.

Xylulose may be L-xylulose or D-xylulose.

Preferably said xylulose is D-xylulose.

In an alternative embodiment, said ketopentose is ribulose. More preferably said ribulose is D-ribulose.

Enzymes

The enzyme nomenclature numbers (EC numbers) mentioned herein refer to the recommendations of the Nomenclature Committee of the International Union of Biochemistry and Molecular Biology on the nomenclature and classification of enzymes published in 1992 (ISBN 0-12-227165-3).

The enzymes mentioned herein can be produced by nucleotide sequences derived from a wide variety of sources. In one aspect, the nucleotide sequences encoding the enzymes mentioned herein may be derived or derivable from *Lactococcus* species (such as *Lactococcus lactis* and *Lactococcus lactis* subsp. *lactis*), *Geobacillus stearothermophilus*, *Enterococcus faecalis*, *Piromyces* sp, *Thermoanaerobacter* species (such as *Thermoanaerobacter thermohydrosulfuricus* and *Thermoanaerobacter thermosulphurigenes*), *Pichia stipitis*, or *Saccharomyces cerevisiae*. Preferably the nucleotide sequences encoding the enzymes mentioned herein are derived or derivable from *Lactococcus* species (such as *Lactococcus lactis* and *Lactococcus lactis* subsp. *lactis*).

Xylose Isomerase (EC 5.3.1.5)

Xylose isomerase has the EC nomenclature number EC 5.3.1.5. Xylose isomerase may be referred to as D-xylose isomerase, D-xylose ketoisomerase or D-xylose ketolisomerase.

The term xylose isomerase refers to an enzyme which is capable of converting D-xylose to D-xylulose and vice versa.

A xylose isomerase mentioned herein is capable of acting on D-xylose.

Xylose isomerase may be derived from a bacterial species such as *Lactococcus* species. In particular, xylose isomerase may be derived from *Lactococcus lactis* subsp. *lactis*; *Lactococcus lactis* subsp. *lactis* strain NRRL B-449; *Lactococcus lactis* subsp. *lactis* strain KF147; *Lactococcus lactis* subsp. *lactis* strain DSM20175; and *Lactococcus lactis* subsp. *lactis* strain IO-1.

Examples of xylose isomerases suitable for use as described herein include xylose isomerases comprising: the amino acid sequence shown as SEQ ID No 14, SEQ ID No 11, SEQ ID No 18, SEQ ID No 13, SEQ ID No 19 or SEQ ID No 20, or a variant, homologue or derivative thereof; the amino acid sequence shown as GenBank accession number ABX75758; or the amino acid sequence shown as GenBank accession number AAD20249.

Examples of xylose isomerases suitable for use as described herein include xylose isomerase encoded by: the nucleotide sequence shown as SEQ ID No 1, SEQ ID No 10, SEQ ID No 17, SEQ ID No 12, SEQ ID No 27 or SEQ ID No 28, or a variant, homologue or derivative thereof; a nucleotide sequence encoding the amino acid sequence shown as SEQ ID No 14, SEQ ID No 11, SEQ ID No 18, SEQ ID No 13, SEQ ID No 19 or SEQ ID No 20, or a variant, homologue or derivative thereof.

Aldose-1-Epimerase (EC 5.1.3.3)

An aldose-1-epimerase mentioned herein is capable of acting on the aldopentose.

Aldose-1-epimerase has the EC nomenclature number 5.1.3.3. Aldose-1-epimerase may be referred to as a mutarotase or an aldose mutarotase.

The term aldose-1-epimerase refers to an enzyme which is capable of converting an α-aldopentose to a β-aldopentose and vice versa.

In a preferred embodiment the aldose-1-epimerase is encoded by a nucleotide sequence selected from the group consisting of: AAD20257, ABX75760, AAK05605, AAD20245, AAD20251, ABJ73095, ABI49935 and AAO80762 (NCBI accession numbers). More preferably the aldose-1-epimerase is selected from the group consisting of: AAD20257, ABX75760, AAK05605, AAD20245 and AAD20251.

Examples of aldose-1-epimerases suitable for use as described herein include aldose-1-epimerase encoded by: the nucleotide sequence of the *Lactococcus lactis* aldose-1-epimerase gene (NCBI accession number AAD20245); the nucleotide sequence of the *Saccharomyces cerevisiae* GAL10 gene (in particular, the part encoding an amino acid sequence having mutarotase activity); and the nucleotide sequence of the *Saccharomyces cerevisiae* strain D0002 GAL10 gene (in particular, the part encoding an amino acid sequence having mutarotase activity).

Aldose Reductase (EC 1.1.1.21)

Aldose reductase has the EC nomenclature number 1.1.1.21. Aldose reductase may be referred to as: polyol dehydrogenase, aldehyde reductase, ALR2, NADPH-aldopentose reductase, NADPH-aldose reductase, alditol:NADP oxidoreductase or alditol:NADP$^+$ 1-oxidoreductase.

The term aldose reductase refers to an enzyme which is capable of converting an alditol to an aldose and vice versa.

An aldose reductase may reduce more than one type of aldose. For example, the same enzyme may be capable of reducing both D-xylose and L-arabinose such an enzyme may thus be called aldose reductase or, it may be called more specifically after one of the substrates, e.g. xylose reductase.

Xylose Reductase (EC 1.1.1.21)

In one embodiment, the aldose reductase is a xylose reductase. Xylose reductase has the EC nomenclature number 1.1.1.21.

The term xylose reductase refers to an enzyme which is capable of converting D-xylose to xylitol and vice versa.

A xylose reductase mentioned herein is capable of acting on D-xylose.

Examples of xylose reductases suitable for use as described herein include xylose reductase encoded by: the nucleotide sequence of *Pichia stipitis* xylose reductase gene (PsXR); the nucleotide sequence of *Pichia stipitis* strain DSM3651 xylose reductase gene (PsXR)—NCBI accession number X59465; the nucleotide sequence of *Candida tenuis* (said nucleotide sequence encoding xylose reductase can be obtained as described by Kavanagh et al, 2003); and the nucleotide sequence of *Neurospora crassa* (said nucleotide sequence encoding xylose reductase can be obtained as described by Woodyer et al, 2005).

Arabinose Reductase (EC 1.1.1.21)

In another embodiment, the aldose reductase is an arabinose reductase. Arabinose reductase has the EC nomenclature number 1.1.1.21.

The term arabinose reductase refers to an enzyme which is capable of converting L-arabinose to L-arabitol and vice versa.

An arabinose reductase mentioned herein is capable of acting on L-arabinose.

D-xylose reductases currently known in the art may also act on L-arabinose as a substrate with similar activity. Hence, the term L-arabinose reductase may also refer to enzymes which are classified as being D-xylose reductases, and the xylose reductases mentioned herein as suitable for introducing xylose metabolism are similarly suitable for use in introducing arabinose metabolism to a microorganism.

In a further embodiment, the aldose reductase may be capable of converting L-lyxose to L-arabitol and vice versa. In another embodiment, the aldose reductase may be capable of converting D-lyxose to D-arabitol and vice versa.

In another embodiment, the aldose reductase may be capable of converting ribose to ribitol (in particular D-ribose to D-ribitol) and vice versa.

Xylulose Reductase (EC 1.1.1.9 and EC 1.1.1.10)

The term xylulose reductase encompasses D-xylulose reductase and L-xylulose reductase.

D-Xylulose Reductase (EC 1.1.1.9)

D-xylulose reductase has the EC nomenclature number 1.1.1.9. D-xylulose reductase may be referred to as xylitol dehydrogenase, xylitol-2-dehydrogenase, 2,3-cis-polyol (DPN)dehydrogenase (C3-5), NAD-dependent xylitol dehydrogenase, erythritol dehydrogenase or pentitol-DPN dehydrogenase.

The term D-xylulose reductase refers to an enzyme which is capable of converting xylitol to D-xylulose and vice versa.

A D-xylulose reductase mentioned herein is capable of acting on xylitol.

Examples of D-xylulose reductases suitable for use as described herein include D-xylulose reductase encoded by: the nucleotide sequence of *Pichia stipitis* D-xylulose gene (PsXDH); and the nucleotide sequence of *Pichia stipitis* strain DSM3651 D-xylulose reductase gene (PsXDH)—NCBI accession number X55392.

L-Xylulose Reductase (EC 1.1.1.10)

L-xylulose reductase has the EC nomenclature number 1.1.1.10. L-xylulose reductase may be referred to as L xylitol dehydrogenase.

The term L-xylulose reductase refers to an enzyme which is capable of converting L-xylulose to xylitol and vice versa.

An L-xylulose reductase mentioned herein is capable of acting on L-xylulose.

A nucleotide sequence encoding L-xylulose reductase may be obtained from *Aspergillus niger* as described by Witteveen et at (1994) or from the yeast *Ambrosiozyma monospora* (Verho et al, 2004).

Xylulokinase (EC 2.7.1.17)

Xylulokinase has the EC nomenclature number 2.7.1.17. Xylulokinase may be referred to as D-xylulokinase.

The term xylulokinase refers to an enzyme which is capable of converting D-xylulose to D-xylulose 5-phosphate and vice versa.

A xylulokinase mentioned herein is capable of acting on D-xylulose.

Examples of xylulokinases suitable for use as described herein include xylulokinase encoded by: the nucleotide sequence of *Pichia stipitis* xylulokinase gene (PsXKS); the nucleotide sequence of *Pichia stipitis* strain DSM3651 xylulokinase gene (PsXKS)—NCBI accession number AF127802; the nucleotide sequence of *S. cerevisiae* xylulokinase gene (ScXKS); and the nucleotide sequence of *S. cerevisiae* strain D0002 xylulokinase gene (ScXKS)—NCBI accession number X61377.

D-Arabinitol 4-Dehydrogenase (EC 1.1.1.11)

D-arabinitol 4-dehydrogenase has the EC nomenclature number 1.1.1.11. D-arabinitol 4-dehydrogenase may be referred to as D-arabitol dehydrogenase or arabitol dehydrogenase.

The term D-arabinitol 4-dehydrogenase refers to an enzyme which is capable of converting D-arabinitol to D-xylulose and vice versa.

A D-arabinitol 4-dehydrogenase mentioned herein is capable of acting on D-arabinitol.

A suitable D-arabinitol 4-dehydrogenase and the corresponding gene is described by Cheng et al 2005.

L-arabinitol 4-dehydrogenase (EC 1.1.1.12)

L-arabinitol 4-dehydrogenase has the EC nomenclature number 1.1.1.12. L-arabinitol 4-dehydrogenase may be referred to as L-arabitol 4-dehydrogenase or pentitol-DPN dehydrogenase.

The term L-arabinitol 4-dehydrogenase refers to an enzyme which is capable of converting L-arabinitol to L-xylulose and vice versa.

An L-arabinitol 4-dehydrogenase mentioned herein is capable of acting on L-arabinitol.

A suitable L-arabinitol 4-dehydrogenase and the corresponding gene is described in Richard et al (2001).

L-Arabinose Isomerase (EC 5.3.1.4)

L-arabinose isomerase has the EC nomenclature number 5.3.1.4. L-arabinose isomerase may be referred to as L-arabinose ketol-isomerase.

The term L-arabinose isomerase refers to an enzyme which is capable of converting L-arabinose to L-ribulose and vice versa.

An L-arabinose isomerase mentioned herein is capable of acting on L-arabinose.

An example of a nucleotide sequence encoding L-arabinose isomerase is the nucleotide sequence which may be obtained from *Lactobacillus plantarum* strain NCIMB8826 (ATCC 14917) (gene described in NCBI accession code NC_004567).

Ribulokinase (EC 2.7.1.16)

Ribulokinase has the EC nomenclature number 2.7.1.16. Ribulokinase may be referred to as L-ribulokinase.

The term ribulokinase refers to an enzyme which is capable of converting (i) L-ribulose to L-ribulose 5-phosphate and vice versa; and/or (ii) D-ribulose to D-ribulose 5-phosphate and vice versa.

A ribulokinase mentioned herein is capable of acting on L-ribulose and/or D-ribulose.

A suitable nucleotide sequence encoding ribulokinase may be obtained from *Lactobacillus plantarum* strain NCIMB8826 (ATCC 14917) (gene described in NCBI accession code NC_004567).

D-Ribulokinase (EC 2.7.1.47)

D-ribulokinase has the EC nomenclature number 2.7.1.47.

The term ribulokinase refers to an enzyme which is capable of converting D-ribulose to D-ribulose 5-phosphate and vice versa.

An example of a nucleotide sequence encoding D-ribulokinase may be obtained from *Botryotinia fuckeliana* (GenBank accession code CH476984). GenBank accession number EDN20859 details the amino acid sequence of a D-ribulokinase.

L-Ribulose Phosphate 4-Epimerase (EC 5.1.3.4)

L-ribulose phosphate 4-epimerase has the EC nomenclature number 5.1.3.4. L-ribulose phosphate 4-epimerase may be referred to as ribulose phosphate 4-epimerase, phosphoribulose isomerase, L-ribulose 5-phosphate 4-epimerase, AraD or L-Ru5P.

The term L-ribulose phosphate 4-epimerase refers to an enzyme which is capable of converting L-ribulose 5-phosphate to D-xylulose 5-phosphate and vice versa.

An L-ribulose phosphate 4-epimerase mentioned herein is capable of acting on L-ribulose 5-phosphate.

A suitable nucleotide sequence encoding L-ribulose phosphate 4-epimerase may be obtained from *Lactobacillus plantarum* strain NCIMB8826 (ATCC 14917) (gene described in NCBI accession code NC_004567).

D-ribitol 4-dehydrogenase (EC 1.1.1.56)

D-ribitol 4-dehydrogenase has the EC nomenclature number 1.1.1.56. This enzyme may also be referred to as ribitol 2-dehydrogenase, adonitol dehydrogenase or ribitol dehydrogenase.

The term D-ribitol 4-dehydrogenase refers to an enzyme which is capable of converting ribitol to D-ribulose and vice versa.

A D-ribitol 4-dehydrogenase mentioned herein is capable of acting on D-ribitol.

A suitable D-ribitol 4-dehydrogenase and the corresponding gene is described by Dothie et al, 1985.

D-Lyxose Isomerase (EC 5.3.1.15)

D-lyxose isomerase has the EC nomenclature number 5.3.1.15. This enzyme may also be referred to as D-lyxose ketol-isomerase.

The term D-lyxose isomerase refers to an enzyme which is capable of converting D-lyxose to D-xylulose and vice versa.

A D-lyxose isomerase mentioned herein is capable of acting on D-lyxose.

A nucleotide sequence encoding a D-lyxose/L-ribose isomerase may be cloned from the organism *Acinetobacter* sp. strain DL-28 (Shimonishi and Izumori, 1996) or from *Aerobacter aerogenes* (Anderson and Allison, 1965).

Ribose Isomerase (EC 5.3.1.20)

Ribose isomerase has the EC nomenclature number 5.3.1.20. This enzyme may also be referred to as D-ribose isomerase or D-ribose ketol-isomerase.

The term ribose isomerase refers to an enzyme which is capable of converting D-ribose to D-ribulose and vice versa.

A ribose isomerase mentioned herein is capable of acting on D-ribose.

D-ribose isomerase has been found in the organism *Mycobacterium smegmatis* (Izumori et al, 1975), from where it may be cloned.

Ribulose-5-phosphate 3-epimerase (EC 5.1.3.1)

Ribulose-5-phosphate 3-epimerase has the EC nomenclature number 5.1.3.1. This enzyme may also be referred to as: pentose-5-phosphate 3-epimerase, phosphoketopentose 3-epimerase, phosphoketopentose epimerase, phosphoribulose epimerase, ribulose-phosphate 3-epimerase; D-ribulose 5-phosphate epimerase; D-ribulose phosphate-3-epimerase; D-ribulose-5-P 3-epimerase; D-xululose-5-phosphate 3-epimerase; erythrose-4-phosphate isomerase; ribulose 5-phosphate 3-epimerase; and xylulose phosphate 3-epimerase.

The term ribulose-5-phosphate 3-epimerase refers to an enzyme which is capable of converting D-ribulose 5-phosphate to D-xylulose 5-phosphate and vice versa.

Examples of ribulose-5-phosphate 3-epimerase suitable for use as described herein include ribulose-5-phosphate 3-epimerase encoded by: the nucleotide sequence of the *S. cerevisiae* RPE1 gene; the nucleotide sequence of the *S. cerevisiae* strain D0002 RPE1 gene; the nucleotide sequence of NCBI accession code NP_012414; and the ribulose-5-phosphate isomerase from *P. stiptitis* that can be found in NCBI accession number NP_012414.

Ribose-5-Phosphate Isomerase (EC 5.3.1.6)

Ribose-5-phosphate isomerase has the EC nomenclature number 5.3.1.6. This enzyme may also be referred to as phosphopentoisomerase, phosphopentoseisomerase, phosphopentosisomerase, phosphoriboisomerase, ribose 5-phosphate epimerase, ribose phosphate isomerase, 5-phosphoribose isomerase, or D-ribose-5-phosphate ketol-isomerase.

The term ribose-5-phosphate isomerase refers to an enzyme which is capable of converting D-ribose 5-phosphate to D-ribulose 5-phosphate and vice versa.

Examples of ribose-5-phosphate isomerase suitable for use as described herein include ribose-5-phosphate ketol-isomerase encoded by: the nucleotide sequence of the *S. cerevisiae* RKI1 gene; the nucleotide sequence of the *S. cerevisiae* strain D0002 RKI1 gene; the nucleotide sequence of NCBI accession code X94335; the nucleotide sequence of NCBI accession code NP_014738, and the ribose-5-phosphate isomerase from *P. stiptitis* that can be found in accession NC_009043.

Transketolase (EC 2.2.1.1)

Transketolase has the EC nomenclature number 2.2.1.1. This enzyme may also be referred to as glycolaldehydetransferase.

The term transketolase refers to an enzyme which is capable of converting sedoheptulose 7-phosphate+D-glyceraldehyde 3-phopshate to D-ribose 5-phospate+D-xylulose 5-phosphate and vice versa.

Examples of transketolases suitable for use as described herein include transketolase encoded by: the nucleotide sequence of the *Saccharomyces cerevisiae* TKL1 gene; the nucleotide sequence of the *Saccharomyces cerevisiae* strain D0002 TKL1 gene; the nucleotide sequence of NCBI accession code X73224; the nucleotide sequence of NCBI accession code NP 015399, and the transketolase from *P. stiptitis* that can be found in accession CP000496.

Transaldolase (EC 2.2.1.2)

Transaldolase has the EC nomenclature number 2.2.1.2. This enzyme may also be referred to as dihydroxyacetonetransferase, dihydroxyacetone synthase, formaldehyde transketolase or glycerone transferase.

The term transaldolase refers to an enzyme which is capable of converting sedoheptulose 7-phosphate+D-glyceraldehyde 3-phopshate to D-erythrose 4-phospate+D-fructose 6-phosphate and vice versa.

Examples of transaldolases suitable for use as described herein include transaldolase encoded by: the nucleotide sequence of the *Saccharomyces cerevisiae* TAL1 gene; the nucleotide sequence of the *Saccharomyces cerevisiae* strain D0002 TAL1 gene; the nucleotide sequence of NCBI accession code X15953; the nucleotide sequence of NCBI accession code NP_013458, and the transaldolase from *P. stiptitis* that can be found in accession CP000502.

Exogenous Xylose Isomerase

In one aspect, the xylose isomerase mentioned herein is an exogenous xylose isomerase.

In one aspect, the nucleotide sequence encoding the xylose isomerase mentioned herein encodes an exogenous xylose isomerase.

Preferably, the exogenous xylose isomerase is derived from a mesophilic microorganism. More preferably the exogenous xylose isomerase is derived from a mesophilic bacterium.

As used herein the term "mesophilic microorganism" refers to a microorganism which grows and/or thrives best at a temperature between 15° C. and 40° C. Examples of mesophilic microorganisms include *Lactococcus* species, *Saccharomyces* species (such as *S. cerevisiae*), *Escherichia* species (such as *E. coli*) and *Bacillus* species (such as *B. subtilis*).

In one embodiment, the exogenous xylose isomerase is derived from a *Lactococcus* species. Preferably, the exogenous xylose isomerase is derived from a *Lactococcus* species capable of growing on xylose. Preferably, the exogenous xylose isomerase is derived from a *Lactococcus lactis*. More preferably, the exogenous xylose isomerase is derived from a *Lactococcus lactis* subsp. *lactis*. In a highly preferred embodiment, the exogenous xylose isomerase is derived from *Lactococcus lactis* strain NRRL B-4449, strain DSM 20175, strain KF147 or strain IO-1.

The microorganism *Lactococcus lactis* subsp. *lactis* may be referred to as *Lactobacillus xylosus*.

Aldopentose Assay

The amount of an aldopentose (such as xylose) in a solution (such as a culture medium) may be determined colorimetrically by the phloroglucinol method, as described by Ebert et al (A Simplified, Colorimetric Micromethod for Xylose in Serum or Urine, with Phloroglucinol, 1979, *Clin. Chem.* 25, no. 8, pp. 1440-1443).

The colour reagent consists of 0.5 g phloroglucinol (1,3,5 trihydroxybenzene), 100 ml glacial acetic acid and 10 ml conc. HCl. 50 µl of sample is added 950 µl of the colour reagent. The mixture is heated to 100° C. for 4 minutes, and the absorbance of the mixture is read at 554 nm. The amount of an aldopentose (such as xylose) in the sample is determined according to a standard curve made with the same aldopentose as standard. This method may also be used to determine the amount of arabinose, lyxose and ribose in a culture medium.

Ketopentose Assay

The amount of a ketopentose (such as xylulose) in a solution (such as a culture medium) may be determined colorimetrically by the cysteine-carbazole method as described by Zacharias Dische and Ellen Borenfreund (1951; *J. Biol. Chem.* 192 (2): 583).

Xylose Isomerase Assay

The amount of xylose isomerase activity in a solution may be determined as follows.

The conversion of xylose into xylulose is determined in a solution containing an amount of the xylose isomerase, 2% xylose and 2 mM $MgCl_2$ in 20 mM TRIS buffer, pH 7.4, and incubated at the temperature of choice. The reaction is started by the addition of the xylose and stopped by placing the reaction or sample of the reaction on ice. The reaction time is typically 30 or 60 minutes, or samples for following the reaction may be taken at different time points. The generated xylulose is quantified using the cysteine/carbazole method (Dische and Borenfreund, 1951). One unit of xylose isomerase activity is defined as the amount of activity that catalyses the conversion of 1 micromole of xylose into xylulose per minute.

In a highly preferred aspect, the transformed microorganism has a xylose isomerase activity of at least 0.2 xylose isomerase units per mg of microorganism protein. The amount of xylose isomerase activity is assayed as mentioned herein and the protein content is determined as described below. The microorganisms having been cultured beforehand for 96 hours or less in a culture medium comprising xylose.

Protein Content

The amount of protein (i.e. the protein content) in a solution was determined by the use of the commercially available BCA assay kit (Pierce Biotechnology inc., USA) based on the bicinchoninic acid assay (Smith et al, 1985), using bovine serum albumin as standard.

Ethanol Assay

The amount of the biofuel as ethanol, in a solution (such as a culture medium) may be determined by the use of a commercially available ethanol assay, the K-ETOH Kit, manufactured and sold by Megazyme International, Bray Business Park, Bray, Co. Wicklow, Ireland; or it may be determined by, for example, the use of gas chromatography.

Pentose Phosphate Pathway

Ketopentoses (such as xylulose) are converted into ethanol via the pentose phosphate pathway. An example of this is shown in FIG. 4.

Examples of enzymes involved in the pentose phosphate pathway include: transketolase, transaldolase, ribose-5-phosphate ketol-isomerase and ribulose-5-phosphate 3-epimerase.

In one embodiment the microorganism according to the present invention has also been transformed to express or overexpress one or more enzymes involved in the pentose phosphate pathway.

In one embodiment the microorganism according to the present invention has also been transformed with one or more nucleotide sequences that cause the microorganism to overexpress one or more enzymes involved in the pentose phosphate pathway. For example, a promoter is inserted into the genome of a microorganism which enables the microorganism to overexpress an endogenous nucleotide sequence encoding an enzyme involved in the pentose phosphate pathway.

In another embodiment the microorganism has been transformed with one or more nucleotide sequences encoding one or more enzymes involved in the pentose phosphate pathway. For example, the microorganism is transformed with an expression vector comprising a nucleotide sequence encoding one or more enzymes involved in the pentose phosphate pathway.

Preferably the expression vector mentioned herein comprises one or more promoters capable of overexpressing one or more nucleotide sequences encoding one or more enzymes involved in the pentose phosphate pathway. Examples of such promoters include the GPD promoter, the TEF promoter and the ADP promoter. Preferred promoters which may be used to overexpress one or more nucleotide sequences encoding one or more enzymes involved in the pentose phosphate pathway can be any of the regulatory elements controlling the expression of nucleotide sequences encoding proteins involved in glycolysis and glucose fermentation.

As used herein, the term "overexpress" in the phrase "one or more nucleotide sequences that cause the microorganism to overexpress one or more enzymes involved in the pentose phosphate pathway" and "one or more promoters capable of overexpressing one or more nucleotide sequences encoding one or more enzymes involved in the pentose phosphate pathway" refers to an increase in expression from zero to a level of expression or going from a lower level of expression to a higher level of expression (e.g. upregulation) when the transformed microorganism is compared to the equivalent microorganism prior to transformation. Microorganisms overexpressing one or more enzymes involved in the pentose phosphate pathway have an increased ability to catalyse the conversion of a ketopentose (such as xylulose 5-phosphate) to a biofuel (such as ethanol).

Preferably said transformed microorganism which overexpresses one or more enzymes involved in the pentose phosphate pathway is able to catalyse the conversion of a ketopentose (such as xylulose 5-phosphate) to a biofuel (such as ethanol) by a rate which is at least 10%, 15%, 20% or 25% higher than an untransformed microorganism.

Examples of microorganisms overexpressing one or more enzymes involved in the pentose phosphate pathway include: (i) microorganisms transformed with one or more expression vectors encoding one or more of transketolase, transaldolase, ribose-5-phosphate ketol-isomerase and ribulose-5-phosphate 3-epimerase; and (ii) microorganisms transformed to upregulate the expression of one or more endogenous nucleotide sequences encoding one or more of transketolase, transaldolase, ribose-5-phosphate ketol-isomerase and ribulose-5-phosphate 3-epimerase (prior to transformation said microorganism was capable of expressing one or more of these enzymes for a given set of culture conditions during exponential growth but after transformation said microorganism is capable of expression one or more of these enzymes at a higher level, in the same culture conditions, during exponential growth).

Variants/Homologues/Derivatives

The present invention encompasses the use of variants, homologues and derivatives of any amino acid sequence of a protein or of any nucleotide sequence encoding such a protein.

In particular, the present invention encompasses the use of variants, homologues and derivatives of the amino acid sequence encoded by SEQ ID No 14, SEQ ID No 11, SEQ ID No 18, SEQ ID No 13, SEQ ID No 19 or SEQ ID No 20.

Further, the present invention encompasses the use of variants, homologues and derivatives of the nucleotide sequence encoding the amino acid sequence shown as SEQ ID No 14, SEQ ID No 11, SEQ ID No 18, SEQ ID No 13, SEQ ID No 19 or SEQ ID No 20; and the nucleotide sequence shown as SEQ ID No 1, SEQ ID No 10, SEQ ID No 17, SEQ ID No 12, SEQ ID No 27 or SEQ ID No 28.

For example, a variant, homologue or derivative of a nucleotide sequence (such as SEQ ID No 1, SEQ ID No 10, SEQ ID No 17, SEQ ID No 12, SEQ ID No 27 or SEQ ID No 28; or the nucleotide sequence encoding the amino acid sequence shown as SEQ ID No 14, SEQ ID No 11, SEQ ID No 18, SEQ ID No 13, SEQ ID No 19 or SEQ ID No 20) may comprise up to 30, 21, 15, 9, 6 or 3 nucleic acid substitutions.

For example, a variant, homologue or derivative of an amino acid sequence (such as SEQ ID No 14, SEQ ID No 11, SEQ ID No 18, SEQ ID No 13, SEQ ID No 19 or SEQ ID No 20) may comprise up to 10, 7, 5, 3, 2 or 1 amino acid substitutions.

Without wishing to be bound by theory, two amino acid residues (namely D296 and D339) in xylose isomerase may be involved in the binding of divalent metal ions in the active site (Meng, M. et al, 1993). In one embodiment, D296 and D339 are important for the binding of divalent metal ions in the active site. Thus, in one embodiment, the variant, homologue or derivative of an amino acid sequence (such as SEQ ID No 14, SEQ ID No 11, SEQ ID No 18, SEQ ID No 13, SEQ ID No 19 or SEQ ID No 20) comprises the amino acid aspartic acid (D) at residue 296 and/or the amino acid aspartic acid (D) at residue 339 of SEQ ID No 14, SEQ ID No 11, SEQ ID No 18, SEQ ID No 13, SEQ ID No 19 and SEQ ID No 20 or equivalent substitution(s) in other suitable amino acid sequences.

Further, without wishing to be bound by theory, the amino acid residue (histidine 101) in xylose isomerase may be involved in the active site (Lee et al 1989). In one embodiment, H101 is important for the active site. Thus, in one embodiment, the variant, homologue or derivative of an amino acid sequence (such as SEQ ID No 14, SEQ ID No 11, SEQ ID No 18, SEQ ID No 13, SEQ ID No 19 or SEQ ID No 20) comprises the amino acid histidine (H) at residue 101 of SEQ ID No 14, SEQ ID No 11, SEQ ID No 18, SEQ ID No 13, SEQ ID No 19 and SEQ ID No 20 or equivalent substitution in other suitable amino acid sequences.

In one embodiment, the variant, homologue or derivative of an amino acid sequence (such as SEQ ID No 14, SEQ ID No 11, SEQ ID No 18, SEQ ID No 13, SEQ ID No 19 or SEQ ID No 20) comprises the amino acid arginine (R) at residue 391 and/or the amino acid lysine (K) at residue 407 of SEQ ID No 14, SEQ ID No 11, SEQ ID No 18, SEQ ID No 13, SEQ ID No 19 and SEQ ID No 20 or equivalent substitutions in other suitable amino acid sequences.

In one embodiment, a variant, homologue or derivative of a nucleotide sequence (such as SEQ ID No 1, SEQ ID No 10, SEQ ID No 17, SEQ ID No 12, SEQ ID No 27 or SEQ ID No 28; or the nucleotide sequence encoding the amino acid sequence shown as SEQ ID No 14, SEQ ID No 11, SEQ ID No 18, SEQ ID No 13, SEQ ID No 19 or SEQ ID No 20) comprises silent codon sequence changes in order that the sequence is optimised for the codon preferences of a particular host cell in which the sequence is expressed. For example, codon usage in a sequence may be optimised based on the yeast codon usage table from the Kazusa codon usage database (Nakamura et al., 2000).

Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 75, 80, 85 or 90% identical; preferably at least 95, 96, 97, 98 or 99% identical to the subject sequence; and in a highly preferred embodiment at least 98, 99 or 99.5% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 80, 85 or 90% identical; preferably at least 95, 96, 97, 98 or 99% identical; and in a highly preferred embodiment at least 98, 99 or 99.5% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software that can perform sequence comparisons include, but are not limited to, the BLAST package (see Ausubel et al., 1999 Short Protocols in Molecular Biology, 4$^{th}$ Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins DG & Sharp PM (1988), Gene 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allylglycine*, β-alanine*, L-α-amino butyric acid*, L-γ-amino butyric acid*, L-α-amino isobutyric acid*, L-ε-amino caproic acid$^{#}$, 7-amino heptanoic acid*, L-methionine sulfone$^{#*}$, L-norleucine*, L-norvaline*, p-nitro-L-phenylalanine*, L-hydroxyproline$^{#}$, L-thioproline*, methyl derivatives of phenylalanine (Phe) such as 4-methyl-Phe*, pentamethyl-Phe*, L-Phe (4-amino)$^{#}$, L-Tyr (methyl)*, L-Phe (4-isopropyl)*, L-Tic (1,2,3,4-tetrahydroisoquinoline-3-carboxyl acid)*, L-diaminopropionic acid$^{#}$ and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences mentioned herein can be obtained in a number of ways. Other variants of the sequences described herein may be obtained for example by probing DNA libraries. In addition, other homologues may be obtained and such homologues and fragments thereof in general will be capable of selectively hybridising to the sequences shown in the sequence listing herein. Such sequences may be obtained by probing cDNA libraries with probes comprising all or part of any one of the sequences in the attached sequence listings under conditions of medium to high stringency.

Variants and strain/species homologues may also be obtained using degenerate PCR which will use primers designed to target sequences within the variants and homologues encoding conserved amino acid sequences within the sequences mentioned herein. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) mentioned herein may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides as used herein.

Polynucleotides such as DNA polynucleotides and probes mentioned herein may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

The invention will now be further described by way of Examples, which are meant to serve to assist one of ordinary skill in the art in carrying out the invention and are not intended in any way to limit the scope of the invention.

EXAMPLES

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Sambrook J., et al (1989) *Molecular Cloning: A Laboratory Manual,* 2nd ed., Vol. 1-3. Cold Spring Harbor Laboratory Press; and Ausubel F. M., et al (1995 (and periodic supplements)) *Current Protocols in Molecular Biology, Vol. ch.* 9, 13 and 16. John Wiley & Sons, New York, N.Y. Each of these general texts is herein incorporated by reference.

Organisms:

*Lactococcus* is family of Gram positive bacteria, commonly found throughout many parts of the world. Strains of this family have a long history of safe use for fermentation of dairy products for production of e.g. cheese. Such a strain is used in these examples, *Lactococcus lactis* strain DSM 20175, which can be obtained from the deposit institute DSMZ—Deutsche Sammlung von Mikroorganismen and Zellkulturen GmbH (German collection of Microorganisms and Cell Cultures).

*Saccharomyces* is a family of yeast strains commonly found throughout many parts of the world. They have a long history of safe use for baking, brewing and winemaking purposes, and are at the present time the most well characterized eucaryotic organism. It is therefore a very popular organism for experimental use in molecular biology and microbiology laboratories. The strain *S. cerevisiae* BY4741 is used in the examples here. The strain can be obtained from Euroscarf (EUROpean *Saccharomyces Cerevisiae* ARchive for Functional Analysis—Germany).

The *S. cerevisiae* strain T0040, *S. cerevisiae* strain T0028, *S. cerevisiae* strain T0049 and *S. cerevisiae* strain T0004 used in the following examples are all isogenic variants, constructed from BY4741 obtained from Euroscarf.

*Escherichia coli* is a Gram negative bacterium that is commonly found in the lower intestine of higher animals and human beings. Many strains of the organism have a long history of safe use in microbiological and molecular biology laboratories. The strain used in the following examples is the *E. coli* DH5-alpha strain, commonly used in molecular biology laboratories for cloning and propagation of genetic material. The strain may be obtained from the company "InVitrogen" (InVitrogen Corporation, California, USA).

*Thermoanaerobacter* is a family of thermophilic, anaerobically growing, Gram positive bacterial strains. The two strains from which enzymes are used in the following examples, *Thermoanaerobacter thermohydrosulfuricus* (DSM no. 15750) and *Thermoanaerobacterium thermosulfurigenes* (ATCC 33743) are both originally isolated from thermal springs, DSM no. 15750 in Ayas, Turkey and ATCC 33743 in Yellowstone National Park, USA. They can be obtained from DSMZ—Deutsche Sammlung von Mikroorganismen und Zellkulturen GmbH (German collection of Microorganisms and Cell Cultures). The genetic material encoding the enzymes from these strains and used in the examples is however made synthetically, based on a back-translation of the amino acid sequences as specified in the sequence listing as SEQ ID No 15 and SEQ ID No 16.

*Pichia stipitis* is a yeast species that has been isolated from the guts of insect larvae and thermites. The *Pichia stipitis* strain from which genes have been used in the following examples is the strain *Pichia stipitis* DSM no. 3651, which can be obtained from DSMZ—Deutsche Sammlung von Mikroorganismen und Zellkulturen GmbH (German collection of Microorganisms and Cell Cultures).

*Pseudomonas* is a diverse family of rodshaped, aerobic Gram negative bacteria commonly found in water and in plant seeds and plant tissue. The strain used in these examples is the *Pseudomonas syringae* strain DSM 50315, originally isolated from wounded plant tissue. The strain can be obtained from the deposit institute DSMZ—Deutsche Sammlung von Mikroorganismen und Zellkulturen GmbH (German collection of Microorganisms and Cell Cultures).

Example 1

Construction of an *S. Cerevisiae* Strain Expressing the *Lactobacillus xylosus* XI and the *Pichia stipitis* Xylulose Kinase Example 1a TOPO Cloning of the D-Xylose Isomerase Gene from *Lactobacillus xylosus* (*Lactococcus Lactis*, Strain DSM 20175), Using Primer Sequences that are Based on NCBI Accession Code AF092042 (SEQ ID No 1)

The entire *L. xylosus* D-xylose isomerase gene (Lx XI) was PCR amplified from DNA obtained from the strain DSM 20175 using the primers identified by SEQ. ID. NO. 2 and SEQ. ID. NO. 3. The coding region of xylose isomerase gene cloned by PCR of *Lactococcus lactis* strain DSM 20175, using primers shown in SEQ ID No 2 and SEQ ID No 3, is shown in SEQ ID No 17. A restriction-site for NheI, proximal to the ATG-start codon and a restriction-site for XhoI, distal to the stop-codon was introduced flanking the Lx XI gene. As template, DNA from the *L. xylosus* strain was used in a concentration of 0.2 ng/µl PCR-reaction. PCR was performed at 30 cycles of 30 seconds at 96° C., 30 seconds at 50° C., and 150 seconds at 72° C., followed by a final incubation of 10 minutes at 72° C. using Phusion High Fidelity DNA polymerase (Finnzymes Oy, Finland). The PCR product was electrophoretically separated on a 1% low melt agarose gel and a 1339 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named pCR-Blunt 2 LxXI.

Example 1b

Construction of Plasmid LxXI-2a Containing the *L. Xylosus* Xylose Isomerase (LxXI) Gene Under Control of the GPD Promoter and the CYC1 Terminator from *S. cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *L. xylosus* xylose isomerase gene was released from the vector pCR-Blunt 2 LxXI (described in Example 1a) by digestion with NheI and XhoI. The resulting linearized plasmid P426-GPD and the DNA fragment encoding ThXI were electrophoretically separated on a 1% low melt agarose gel and isolated. The two DNA fragments were ligated together resulting in the plasmid named LxXI-2a.

Example 1c

TOPO Cloning of the D-Xylulokinase Gene from the *Pichia stipitis* Strain DSM3651 Based on NCBI Accession Code AF127802

The entire *P. stipitis* D-xylulokinase gene (PsXKS) was PCR amplified from DNA obtained from the strain DSM3651 using the primers identified by SEQ. ID. NO. 4 and SEQ. ID. NO. 5. A restriction-site for NheI, proximal to the ATG-start codon and a restriction-site for XhoI, distal to the stop-codon was introduced flanking the PsXKS gene. As template, DNA from the *P. stipitis* strain was used in a concentration of 0.2 ng/µl PCR-reaction. PCR was performed at 30 cycles of 30 seconds at 96° C., 30 seconds at 50° C., and 150 seconds at 72° C., followed by a final incubation of 10 minutes at 72° C. using Phusion High Fidelity DNA polymerase (Finnzymes Oy, Finland). The PCR product was electrophoretically separated on a 1% low melt agarose gel and a 1891 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named pCR-Blunt 2 P.stip XKS.

Example 1d

Construction of Plasmid PsXKS-14a Containing the *P. Stipitis* D-Xylulokinase (PsXKS) Gene Under Control of the GPD Promoter and the CYC1 Terminator from *S. Cerevisiae*

The *E. coli/S. cerevisiae* high-copy shuttle vector P425-GPD (Mumberg et al., 1995) was digested with SpeI and XhoI and the resulting termini were dephosphorylated with alkaline phosphatase. Similarly, the DNA fragment encoding the *P. stipitis* xylulose kinase gene was released from the vector pCR-Blunt 2 P.stip XKS (described in Example 1c), by digestion with NheI and XhoI. The resulting linearized plasmid P425-GPD and the DNA fragment encoding PsXKS were electrophoretically separated on a 1% low melt agarose gel and isolated. The two DNA fragments were ligated together resulting in the plasmid named PsXKS-14a.

Example 1e

Construction of *S. Cerevisiae* Strains Containing the LxXI-2a and the PsXKS-14a 200 ng each of the plasmids were combined and used for the transformation of *S. cerevisiae* yeast strain BY4741 (Euroscarf, Germany) by means of electroporation using the Biorad Gene Pulser II system (Biorad, USA) according to the manufacturer's instruction. Yeast cells were made competent according to a standard protocol (Becker and Guarente, 1991). Selection for clones transformed with both plasmids was done on solid synthetic complete dropout media omitting uracil and leucine and supplemented with 2% D-glucose (SC-Ura, Leu) (Rose et al., 1990). Medium-size primary clones were restreaked on SC-Ura, Leu and one colony of strain T0004 transformed with the plasmids LxXI-2a and PsXKS-14a was obtained.

Example 2

Construction of an *S. Cerevisiae* Strain Expressing the *Thermoanaerobacter thermohydrosulfuricus* XI and the *Pichia stipitis* Xylulose Kinase Example 2a Construction of Synthetic Xylose Isomerase Gene Encoding *Thermoanaerobacter thermohydrosulfuricus* Xylose Isomerase Based on NCBI Accession Code D00756

The entire *T. thermohydrosulfuricus* xylose isomerase gene (ThXI) was synthesized and assembled by Geneart AG (Regensburg, Germany). Codon usage in the sequence was optimised based on the yeast codon usage table from the Kazusa codon usage database (Nakamura et al., 2000). Flanking the open reading frame, a restriction-site for NheI, proximal to the ATG-start codon and a restriction-site for XhoI, distal to the stop-codon, were included in the synthetic construct. The integrity of the ThXI synthetic gene was determined by sequencing of both strands. The nucleotide sequence of ThXI including flanking restriction-sites is identified as SEQ. ID. NO. 6, showing the synthesized DNA sequence with the amino acid translation of the coding region shown above the nucleotide sequence. The harbouring plasmid was named 0717046pGA14.

Example 2b

Construction of Plasmid ThXI-5a Containing the *T. thermohydrosulfuricus* Xylose Isomerase (ThXI) Gene Under Control of the GPD Promoter and the CYC1 Terminator from *S. Cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *T. thermohydrosulfuricus* xylose isomerase gene was released from the vector 0717046pGA14 (described in Example 2a) by digestion with NheI and XhoI. The resulting linearized plasmid P426-GPD and the DNA fragment encoding ThXI were electrophoretically separated on a 1% low melt agarose gel and isolated. The two DNA fragments were ligated together resulting in the plasmid named ThXI-5 a.

Example 2c

Construction of *S. Cerevisiae* Strains Containing the ThXI-5a and the PsXKS-14a 200 ng each of the plasmids were combined and used for the transformation of *S. cerevisiae* yeast strain BY4741 (Euroscarf, Germany) by means of electroporation using the Biorad Gene Pulser II system (Biorad, USA) according to the manufacturer's instruction. Yeast cells were made competent according to a standard protocol (Becker and Guarente, 1991). Selection for clones transformed with both plasmids was done on solid synthetic complete dropout media omitting uracil and leucine and supplemented with 2% D-glucose (SC-Ura, Leu) (Rose et al., 1990). Medium-size primary clones were restreaked on SC-Ura, Leu and one colony of strain T0049 transformed with the plasmids ThXI-5a and PsXKS-14a was obtained.

Example 3

Construction of an *S. Cerevisiae* Strain Expressing the *Thermoanaerobacter thermosulphurigenes* Xylose Isomerase and the *Pichia stipitis* Xylulose Kinase Example 3a Construction of Synthetic Xylose Isomerase Gene Encoding *Thermoanaerobacter thermosulphurigenes* Xylose Isomerase Based on NCBI Accession code J05650

The entire *T. thermosulphurigenes* xylose isomerase gene (TsXI) was synthesized and assembled by Geneart AG (Regensburg, Germany). Codon usage in the sequence was optimised based on the yeast codon usage table from the Kazusa codon usage database (Nakamura et al., 2000). Flanking the open reading frame, a restriction-site for NheI, proximal to the ATG-start codon and a restriction-site for XhoI, distal to the stop-codon, were included in the synthetic construct. The integrity of the TsXI synthetic gene was determined by sequencing of both strands. The nucleotide sequence of TsXI including flanking restriction-sites is identified as SEQ. ID. NO. 7, showing the synthesized DNA sequence with the amino acid translation of the coding region shown above the nucleotide sequence. The harbouring plasmid was named 0717047pGA18.

Example 3b

Construction of Plasmid TsXI-28a Containing the *T. thermosulphurigenes* Xylose Isomerase (TsXI) Gene Under Control of the GPD Promoter and the CYC1 Terminator from *S. Cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *T. thermosulphurigenes* xylose isomerase gene was released from the vector 0717047pGA18 (described in Example 3a) by digestion with NheI and XhoI. The resulting linearized plasmid P426-GPD and the DNA fragment encoding TsXI were electrophoretically separated on a 1% low melt agarose gel and isolated. The two DNA fragments were ligated together resulting in the plasmid named TsXI-28a.

Example 3c

Construction of *S. cerevisiae* strains containing the TsXI-28a and the PsXKS-14a 200 ng each of the plasmids were combined and used for the transformation of *S. cerevisiae* yeast strain BY4741 (Euroscarf, Germany) by means of electroporation using the Biorad Gene Pulser II system (Biorad, USA) according to the manufacturer's instruction. Yeast cells were made competent according to a standard protocol (Becker & Guarente, 1991). Selection for clones transformed with both plasmids was done on solid synthetic complete dropout media omitting uracil and leucine and supplemented with 2% D-glucose (SC-Ura, Leu) (Rose et al., 1990). Medium-size primary clones were restreaked on SC-Ura, Leu and one colony of strain T0028 transformed with the plasmids TsXI-28a and PsXKS-14a was obtained.

Example 4

Construction of a *S. Cerevisiae* Strain Expressing the *Pseudomonas syringae* XylA (PsXI) and the *Pichia stipitis* Xylulose Kinase Example 4a—TOPO Cloning of the D-Xylose Isomerase Gene (PsXI) from *Pseudomonas syringae* pv Tomato The entire *P. syringae* D-xylose isomerase gene (Ps XI) was PCR amplified from DNA obtained from the strain DSM 50315 using the primers identified by SEQ. ID. NO. 8 and SEQ. ID. NO. 9. A restriction-site for NheI, proximal to the ATG-start codon and a restriction-site for XhoI, distal to the stop-codon was introduced flanking the PsXI gene. As template, DNA from the *P. syringae* strain was used in a concentration of 0.2 ng/µl PCR-reaction. PCR was performed at 30 cycles of 30 seconds at 96° C., 30 seconds at 50° C., and 150 seconds at 72° C., followed by a final incubation of 10 minutes at 72° C. using Phusion High Fidelity DNA polymerase (Finnzymes Oy, Finland). The PCR product was electrophoretically separated on a 1% low melt agarose gel and a 1323 bp fragment was isolated. The DNA fragment was TOPO cloned into the pCR-Blunt II-TOPO vector (Invitrogen, USA) according to the manufacturer's instructions and the resulting plasmid was used for the transformation of *E. coli* TOP10. The plasmid was named pCR-Blunt 2 PsXI.

Example 4b

Construction of Plasmid PsXI-34a Containing the *P. Syringae* Xylose Isomerase (PsXI) Gene Under Control of the GPD Promoter and the CYC1 Terminator from *S. cerevisiae*

The *E. coli/S. cerevisiae* high-copy shuttle vector P426-GPD (Mumberg et al., 1995) was digested with SpeI and XhoI and the resulting termini were dephosphorylated with alkaline phosphatase. Similarly, the DNA fragment encoding the *P. syringae* xylose isomerase gene was released from the vector pCR-Blunt 2 PsXI (described in Example 4a) by digestion with NheI and XhoI. The resulting linearized plasmid P426-GPD and the DNA fragment encoding PsXI were electrophoretically separated on a 1% low melt agarose gel and isolated. The two DNA fragments were ligated together resulting in the plasmid named PsXI-34a.

Example 4c

Construction of *S. Cerevisiae* Strains Containing the PsXI-34a and the PsXKS-14a 200 ng each of the plasmids were combined and used for the transformation of *S. cerevisiae* yeast strain BY4741 (Euroscarf, Germany) by means of electroporation using the Biorad Gene Pulser II system (Biorad, USA) according to the manufacturer's instruction. Yeast cells were made competent according to a standard protocol (Becker and Guarente, 1991). Selection for clones transformed with both plasmids was done on solid synthetic complete dropout media omitting uracil and leucine and supplemented with 2% D-glucose (SC-Ura, Leu) (Rose et al., 1990). Medium-size primary clones were restreaked on SC-Ura, Leu and one colony of strain T0040 transformed with the plasmids PsXI-34a and PsXKS-14a was obtained.

Example 5

Determination and Comparing of Specific Xylose Isomerase Activities Obtained by Expression of Four Different Bacterial Xylose Isomerases in *Saccharomyces cerevisiae*

The four different strains:
- *S. cerevisiae* strain T0040 containing the PsXI-34a and the PsXKS-14a;
- *S. cerevisiae* strains T0028 containing the TsXI-28a and the PsXKS-14a;
- *S. cerevisiae* strains T0049 containing the ThXI-5a and the PsXKS-14a; and
- *S. cerevisiae* strains T0004 containing the LxXI-2a and the PsXKS-14a; were streaked on plates and grown overnight on solid synthetic complete dropout media omitting uracil and leucine and supplemented with 2% D-glucose (SC-Ura, Leu) (Rose et al., 1990).

50 ml tubes containing 10 ml synthetic complete dropout media omitting uracil and leucine and supplemented with 2% D-glucose (SC-Ura, Leu) (Rose et al, 1990), were then inoculated with colonies from the streaked plates to an adjusted OD600 of 0.1 and grown for 18 hours under shaking, 200 rpm, at 30° C. The cultures were harvested by centrifugation, 4000 rpm for 15 minutes, washed by resuspension in 2 ml of water and spun down again. Cells were lysed by addition of 300 µl of CelLytic Y Plus Kit (Sigma-Aldrich) followed by incubation at room temperature for 30 minutes under gentle shaking and centrifugation at 16000×g for 10 minutes to remove the cell debris. The supernatant was isolated and used for determination of xylose isomerase activity and protein content. Xylose isomerase activity was determined using the cysteine-carbazole method as described by Dische and Borenfreund (Dische and Borenfreund, 1951). Protein content was determined by the use of commercially available bicinchoninic acid assay based protein assay (BCA assay kit, Pierce Biotechnology inc., USA).

Results are shown in FIG. 5. The highest total xylose isomerase activity per mg total yeast protein, obtained by expressing the *L. xylosus* xylose isomerase, is about 10 times higher than the second best result, obtained by expressing the xylose isomerase from *T. thermohydrosulphuricus*. It is clear that the *L. xylosus* xylose isomerase is far superior to the other bacterial isomerases. The obtained results, xylose isomerase units/mg yeast protein for the two thermophilic bacteria, are in line with other obtained results using xylose isomerases from thermophilic bacteria (Walfriedsson et al, 1996; Lönn et al, 2003), and *L. xylosus* isomerase specific activity equals or tops the specific activity obtained by the use of the xylose isomerase from the fungus *Piromyces* sp. EII (Kuyper et al, 2003).

Example 6

Growth on Xylose as the Carbon Source of *S. Cerevisiae* Strains Expressing LxXI-2a and PsXKS-14a (strain T0004)

*S. cerevisiae* strain T0004, described in Example 1e, comprises an expression cassette containing SEQ ID No 17 (which encodes xylose isomerase) and an expression cassette containing the nucleotide sequence encoding *P. stipitis* xylulokinase.

Strain T0004, described in Example 1e, was gradually adapted to growth on xylose by serial dilution of the glucose content, followed by growth on xylose as the only carbon source. This was carried out using the following procedure:

Recipe of Synthetic Complete growth medium without uracil and leucine (SC-Ura&Leu medium):

Bacto-yeast nitrogen base without amino acids: 6.7 g/l; supplied with 40 mg/l of all amino acids except Leucine; and supplied with p-aminobenzoic acid, 40 mg/l.

Inoculating a first culture tube containing 10 ml SC-Ura&Leu medium containing 2% xylose+0.5% glucose with strain T0004. Incubating the tube at 30° C. and 150 rpm rotary shaking until OD600 reached 1.5. This culture is herein referred to as '1. culture'.

Inoculating a second culture tube containing 9 ml SC-Ura&Leu medium containing 2% xylose with 1 ml of the above described '1. culture'. Incubating the culture tube at 30° C. and 150 rpm rotary shaking until OD600 reached approximately 1.0. This culture is herein referred to as '2. culture'.

Inoculating a third culture tube containing 9 ml SC-Ura&Leu medium containing 2% xylose with 1 ml of the above described '2. culture'. Incubating the culture tube at 30° C. and 150 rpm rotary shaking until OD600 was between 0.5 and 1.0. This culture is herein referred to as '3. culture'.

Inoculating a 250 ml shakeflask with baffles, containing 50 ml SC-Ura&Leu medium containing 2% xylose with an amount of the '3. culture' to reach an OD600 value of 0.05. Incubating the culture tube at 30° C. and 150 rpm rotary shaking and following the growth by OD600 measurements through a culture period of 240 hours.

The growth of strain T0004 on xylose as the carbon source can be seen in FIG. 6. After a lag phase, the maximum growth rate reached 0.05/h without other modifications of the strain.

Example 7

Demonstration of High Xylose Isomerase Activity in *S. Cerevisiae* Cells by Intracellular Expression of Three Naturally Occurring Variants and Two Artificial Variants of a *Lactococcus* Isomerase The naturally occurring xylose isomerases with amino acid sequences as shown in SEQ ID NO 13, SEQ ID NO 14 and SEQ ID NO 18 where expressed intracellular in *Saccharomyces cerevisiae* strain BY4741 (Euroscarf, Germany). In addition, two related variants, not found in any organism, were generated (as detailed below) and also expressed. The amino acid sequences of these two variants are shown in SEQ ID NO 19 and SEQ ID NO 20. Except for variation in amino acid position 391 (arginine or lysine), position 407 (glutamic acid or lysine) or 416 (tyrosine or histidine), all variants have identical amino acid sequences. This means that when compared to SEQ ID No 18, SEQ ID No 13 has the amino acid K at position 391, the amino acid K at position 407 and the amino acid H at position 416. These amino acids in SEQ ID No 13 are underlined in the sequence listing. Compared to SEQ ID No 18, SEQ ID No 14 has the amino acid K at position 391. This amino acid in SEQ ID No 14 is underlined in the sequence listing. Compared to SEQ ID No 18, SEQ ID No 19 has the amino acid K at position 407 and the amino acid H at position 416. These amino acids in SEQ ID No 19 are underlined in the sequence listing. Compared to SEQ ID No 18, SEQ ID No 20 has the amino acid K at position 407. This amino acid in SEQ ID No 20 is underlined in the sequence listing.

DNA sequences encoding the amino acid sequences SEQ ID NO 13, SEQ ID NO 14, SEQ ID NO 19 and SEQ ID NO 20 used in this example were all generated by site directed mutagenesis of the DNA sequence shown as SEQ ID NO 17, using the construct obtained as described in Example 1a as initial template. (The amino acid sequence SEQ ID No 18 is encoded by SEQ ID No 17.) Site directed mutagenesis was done by using the "Quick Change" kit (Stratagene, La Jolla, USA) to change the codons encoding amino acid residues 391, 407 and 416 respectively. The kit was used according to the manufacturer's protocol. The sequences of the mutagenic DNA primers used are shown in SEQ ID NO 21 and SEQ ID NO 22 (R391K substitution and removal of a Psp14061 restriction site), SEQ ID NO 23 and SEQ ID NO 24 (E407K substitution and addition of a HindIII restriction site) and SEQ ID NO 25 and SEQ ID NO 26 (combined E407K and Y416H substitution and addition of a HindIII restriction site). The addition or removal of restriction sites allow for easy identification of mutated vectors. The correct overall DNA sequences of the generated DNA constructs were subsequently confirmed by DNA sequencing.

A modified version of the *E. coli/S. cerevisiae* high-copy shuttle vector pRS426-gpd (Mumberg et al., 1995) was used for intracellular expression of the xylose isomerase variants. The vector was modified by exchanging the URA3 marker in pRS426-gpd with the nourseothricin resistance marker from vector pAG35 (Euroscarf, Germany), using standard molecular biology subcloning techniques. The resultant shuttle vector confers nourseothricin resistance to *S. cerevisiae*.

The five different xylose isomerase genes were isolated and inserted into the modified expression vector according to the description in Example 1b. The resulting plasmid constructs were named pRS426gpd_nat::XI13, pRS426gpd_nat::XI14, pRS426gpd_nat::XI18, pRS426gpd_nat::XI19 and pRS426gpd_nat::XI20, respectively.

Each variant plasmid construct was transformed into a strain of *S. cerevisiae* BY4741 (Euroscarf, Germany) by means of electroporation using the Biorad Gene Pulser II system (Biorad, USA) according to the manufacturer's instruction. Yeast cells were made competent according to a standard protocol (Becker and Guarente, 1991). Selection for transformed clones was done on YPD plates (20 g/l tryptone, 10 g/l yeast extract and 20 g/l glucose with 15 g/l bactoagar added for solidification) containing 100 mg/l nourseothricin.

Five cell lines, each expressing one of the variant *Lactococcus* xylose isomerases were obtained.

The specific xylose isomerase activity of each cell line was determined in duplicate and compared as described in Example 5, except that the medium used for yeast growth was YPD (20 g/l tryptone, 10 g/l yeast extract and 20 g/l glucose) supplied with 100 mg/l nourseothricin The obtained average specific xylose isomerase activity of the duplicate determinations, calculated as xylose isomerase units/mg of total extracted yeast protein, of the five strains is shown in FIG. 7.

All tested *Lactococcus* xylose isomerase variants are highly active when expressed in *S. cerevisiae*. This can be therefore be regarded to be general for *lactococcus* xylose isomerase genes that encodes active xylose isomerases in *Lactococcus*. It appears that, comparing the activity of SEQ ID 19 and SEQ ID 20, the Y416H substitution makes very little difference in activity. In contrast, the K391R substitution and the E407K substitution both increase the specific activity in yeast by approximately 15-20%, an effect that appears to be additive if those two substitutions are combined as in SEQ ID NO 19 and SEQ ID NO 20.

REFERENCES

Anderson R. L. and Allison D. P. (1965) Purification and Characterization of D-Lyxose Isomerase. *J. Biol. Chem.* 240, 2367-2372.

Ausubel F. M., Brent R., Kingston R. E., Moore D., Seidman J. G., Smith J. A., and Struhl K., eds (1995 (and periodic supplements)) *Current Protocols in Molecular Biology*, Vol. ch. 9, 13 and 16. John Wiley & Sons, New York, N.Y.

Bao X., Gao D., and Wang Z. (1999) Expression of xylose isomerase gene (xylA) in *Saccharomyces cerevisiae* from *Clostridium thermohydrosulphuricum. Wei Sheng Wu Xue Bao* 39, 49-54.

Becker D. M. and Guarente L. (1991) High-efficiency transformation of yeast by electroporation. *Methods Enzymol.* 194, 182-187.

Cheng H., Jiang N., Shen A., and Feng Y. (2005) Molecular cloning and functional expression of D-arabitol dehydrogenase gene from *Gluconobacter oxydans* in *Escherichia coli. FEMS Microbiol. Lett.* 252, 35-42.

Dische Z. and Borenfreund E. (1951) A new spectrophotometric method for the detection and determination of keto sugars and trioses. *J. Biol. Chem.* 192, 583.

Dothie J. M., Giglio J. R., Moore C. B., Taylor S. S., and Hartley B. S. (1985) Ribitol dehydrogenase of *Klebsiella aerogenes*. Sequence and properties of wild-type and mutant strains. *Biochem. J.* 230, 569-578.

Gait M. J., ed (1984) *Oligonucleotide Synthesis: A Practical Approach*. Oxford University Press.

Izumori K., Rees A. W., and Elbein A. D. (1975) Purification, Crystallization, and Properties of D-Ribose Isomerase from *Mycobacterium smegmatis. J. Biol. Chem.* 250, 8085-8087.

Kavanagh K., Klimcek M., Nidetsky B., and Wilson D. K. (2003) Structure of xylose reductase bound to NAD+ and the basis for single and dual co-substrate specificity in family 2 aldo-keto reductases. *Biochem. J.* 373, 319-326.

Kuyper M., Harhangi H. R., Stave A. K., Winkler A. A., Jetten M. S., de Laat W. T., den Ridder J. J., Op den Camp H. J., van Dijken J. P., and Pronk J. T. (2003) High-level functional expression of a fungal xylose isomerase: the key to efficient ethanolic fermentation of xylose by *Saccharomyces cerevisiae. FEMS Yeast Research* 4, 69-78.

Lee C., Bagdasarian M., Meng M., and Zeikus J. G. (1989) Catalytic Mechanism of Xylose (Glucose) Isomerase from *Clostridium thermosulfurogenes*. Characterization of the structural gene and function of active site histidine. *J. Biol. Chem.* 265, 19082-19090.

Lee Y. E., Jan M. K., Lee C., Lowe S. E., and Zeikus J. G. (1993) Taxonomic distinction of saccharolytic thermophilic anaerobes: description of *Thermoanaerobacterium xylanolyticum* gen. nov., sp. nov., and *Thermoanaerobacterium saccharolyticum* gen. nov., sp. nov.; reclassification of *Thermoanaerobium brockii, Clostridium thermosulfurogenes*, and *Clostridium thermohydrosulfuricum* E100-69 as *Thermoanaerobacter brockii* comb. nov., *Thermoanaerobacterium thermosulfurigenes* comb. nov., and *Thermoanaerobacter thermohydrosulfuricus* comb. nov., respectively; and transfer of *Clostridium thermohydrosulfuricum* 39E to *Thermoanaerobacter ethanolicus. Int. J. Syst. Bacteriol.* 43, 41-51.

Lilley D. M. J. and Dahlberg J. E., eds (1992) *Methods in Enzymology: DNA Structures Part A: Synthesis and Physical Analysis of DNA*, Vol. 211. Academic Press.

Lönn A., Gardonyi M., van Zyl W., Hahn-Hägerdahl B., and Otero R. C. (2002) Cold adaptation of xylose isomerase from *Thermus thermophilus* through random PCR mutagenesis. *Eur. J. Biochem.* 269, 157-163.

Meng M., Bagdasarian M., and Zeikus J. G. (1993) The role of active-site aromatic and polar residues in catalysis and substrate discrimination by xylose isomerase. *Proc. Natl. Acad. Sci. USA* 90, 8459-8463.

Mumberg D., Mailer R., and Funk M. (1995) Yeast vectors for the controlled expression of heterologous proteins in different genetic backgrounds. *Gene* 156, 119-122.

Nakamura Y., Gojobori T., and Ikemura T. (2000) Codon Usage tabulated from international DNA sequence databases: status for the year 2000. *Nucleic Acids Res.* 28, 292.

Richard P., Londesborough J., Putkonen M., Kalkkinen N., and Penttila M. (2001) Cloning and Expression of a Fungal L-Arabinitol 4-Dehydrogenase Gene. *J. Biol. Chem.* 276, 40631-40637.

Roe B., Crabtree J., and Kahn A., eds (1996) *DNA Isolation and Sequencing: Essential Techniques*. John Wiley & Sons.

Rose M. D., Winston F., and Hieter P., eds (1990) *Methods in Yeast Genetics: A Laboratory Course Manual*. Cold Spring Harbor Laboratory Press.

Sambrook J., Fritsch E. F., and Maniatis T., eds (1989) *Molecular Cloning: A Laboratory Manual*, 2nd ed., Vol. 1-3. Cold Spring Harbor Laboratory Press.

Shimonishi T. and Izumori K. (1996) A new enzyme, L-ribose isomerase from *Acinetobacter* sp. strain DL-28. *J. Ferment. Bioeng.* 81, 493-497.

Smith P. K., Krohn R. I., Hermanson G. T., Mallia A. K., Gartner F. H., Provenzano M. D., Fujimoto E. K., Goeke N. M., Olson B. J., and Klenk D. C. (1985) Measurement of protein using bicinchoninic acid. *Anal. Biochem.* 150, 76-85.

Verho R., Putkonen M., Londesborough J., Penttila M., and Richard P. (2004) A Novel NADH-linked L-Xylulose Reductase in the L-Arabinose Catabolic Pathway of Yeast. *J. Biol. Chem.* 279, 14746-14751.

Walfridsson M., Bao X., Anderlund M., Lilius G., and Hahn-Hagerdal B. (1996) Ethanolic Fermentation of Xylose with *Saccharomyces cerevisiae* Harboring the *Thermus thermophilus* xylA Gene, Which Expresses an Active Xylose (Glucose) Isomerase. *Appl. Environ. Microbiol.* 62, 4648-4651.

Wang P. Y. and Schneider H. (1980) Growth of yeasts on D-xylulose. *Can. J. Microbiol.* 26, 1165-1168.

Witteveen C. F. B., Weber F., Busink R., and Visser J. (1994) Isolation and characterisation of two xylitol dehydrogenases from *Aspergillus niger. Microbiol.* 140, 1679-1685.

Woodyer R., Simurdiak M., van der Donk W. A., and Zhao H. (2005) Heterologous Expression, Purification, and Characterization of a Highly Active Xylose Reductase from *Neurospora crassa. Appl. Environ. Microbiol.* 71, 1642-1647.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

```
SEQUENCE LISTING
SEQ ID No. 1:
Coding region of Lactococcus lactis subsp. lactis (Lactobacillus xylosus) strain NRRL-
4449 xylose isomerase gene as described in accession number AF092042. The amino acid
sequence encoded by this nucleotide sequence is shown as SEQ ID No 14.
            M   A   Y   F   N   D   I   A   P   I   K   Y   E   G   T   K
    1     ATG GCT TAC TTT AAC GAC ATC GCA CCT ATC AAA TAC GAA GGT ACA AAA T   K   N   M   F   A   F   R   H   Y   N   P   E   E   V   V
   49     ACT AAA AAT ATG TTT GCC TTT CGC CAT TAT AAT CCA GAA GAA GTA GTT A   G   K   T   M   E   E   Q   L   H   F   A   L   A   F   W
   97     GCT GGT AAA ACA ATG GAA GAA CAA CTT CAT TTT GCC CTT GCA TTT TGG H   T   I   T   M   D   G   S   D   P   F   G   G   A   T   M
  145     CAT ACA ATT ACA ATG GAT GGG TCA GAT CCC TTT GGG GGA GCA ACA ATG E   R   P   W   D   L   E   G   G   S   E   L   D   R   A   H
  193     GAA CGC CCT TGG GAT TTG GAA GGT GGT TCT GAA CTT GAC CGT GCT CAC R   R   V   D   A   F   F   E   I   A   E   K   L   G   V   K
  241     CGT CGA GTA GAT GCT TTC TTT GAA ATT GCT GAA AAA TTA GGT GTT AAA Y   Y   C   F   H   D   I   D   I   A   P   T   G   N   S   L
  289     TAT TAT TGT TTC CAT GAT ATT GAT ATT GCA CCT ACT GGA AAT TCT TTG K   E   F   Y   A   N   L   D   E   I   T   D   H   L   L   E
  337     AAA GAA TTT TAT GCT AAT TTG GAC GAA ATT ACT GAC CAC CTT CTT GAA K   Q   K   A   T   G   I   K   L   L   W   N   T   A   N   M
  385     AAA CAA AAA GCA ACA GGG ATT AAA TTA CTT TGG AAT ACA GCA AAC ATG F   S   N   P   R   Y   M   N   G   V   S   T   S   N   R   A
  433     TTT TCA AAT CCC CGC TAT ATG AAT GGT GTT TCA ACT TCT AAT CGT GCT E   V   F   A   Y   G   A   A   Q   V   K   K   G   L   E   L
  481     GAA GTC TTT GCT TAT GGT GCT GCA CAA GTT AAA AAA GGT CTT GAA CTT S   K   K   L   G   G   E   N   Y   V   F   W   G   G   R   E
  529     TCT AAA AAA CTC GGT GGT GAA AAT TAC GTC TTC TGG GGT GGT CGT GAA G   Y   E   S   L   L   N   T   D   M   G   L   E   M   D   H
  577     GGT TAT GAA TCA CTT TTG AAT ACA GAT ATG GGT CTT GAA ATG GAT CAT M   A   K   F   F   H   L   A   I   D   Y   A   K   S   I   N
  625     ATG GCA AAA TTC TTC CAT TTG GCA ATT GAT TAT GCA AAA TCA ATC AAC H   L   P   I   F   L   I   E   P   K   P   K   E   P   M   T
  673     CAC TTG CCC ATT TTC TTG ATT GAA CCA AAA CCA AAA GAA CCA ATG ACT H   Q   Y   D   F   D   S   A   T   A   L   A   F   L   Q   K
  721     CAC CAA TAT GAT TTT GAC TCA GCA ACA GCT CTT GCT TTC TTG CAA AAA Y   D   L   D   K   Y   F   K   L   N   L   E   T   N   H   A
  769     TAT GAT TTG GAC AAA TAT TTC AAA CTC AAT CTT GAA ACA AAT CAT GCT
```

```
              W   L   A   G   H   T   F   E   H   E   L   N   T   A   R   T
817          TGG TTG GCT GGA CAC ACT TTT GAA CAC GAA TTA AAT ACT GCT CGT ACT

F   N   A   L   G   S   I   D   A   N   Q   G   N   Y   L   L
865          TTC AAT GCT TTG GGT TCT ATT GAT GCC AAT CAA GGA AAT TAC TTG CTT

G   W   D   T   D   E   F   P   T   L   V   I   D   I   T   L
913          GGT TGG GAT ACA GAT GAA TTC CCA ACA CTT GTT ATT GAT ATC ACA CTT

A   M   H   Q   I   L   L   N   G   G   L   G   K   G   G   I
961          GCG ATG CAC CAA ATT CTT TTG AAC GGT GGA CTT GGC AAA GGT GGA ATT

N   F   D   A   K   V   R   R   T   S   F   K   A   E   D   L
1009         AAC TTT GAT GCG AAA GTA CGT CGT ACA AGT TTC AAA GCA GAA GAT TTA

I   L   A   H   I   A   G   M   D   T   Y   A   R   A   L   K
1057         ATT CTT GCT CAT ATT GCA GGG ATG GAT ACT TAT GCG CGT GCT TTG AAA

G   A   A   A   I   I   E   D   K   F   L   S   D   I   V   D
1105         GGT GCA GCA GCA ATC ATT GAA GAT AAA TTC TTG TCT GAT ATT GTT GAC

E   R   Y   S   S   Y   K   N   T   E   V   G   Q   S   I   E
1153         GAA CGT TAT AGT TCA TAC AAA AAT ACA GAA GTT GGT CAA TCC ATT GAA

N   G   T   A   T   F   E   S   L   A   A   F   A   L   E   Y
1201         AAT GGA ACA GCA ACT TTT GAA AGT CTT GCC GCA TTT GCA CTT GAA TAT

G   D   D   I   E   L   D   S   N   H   L   E   Y   I   K   S
1249         GGT GAT GAT ATT GAA CTT GAT TCT AAT CAC TTG GAA TAC ATC AAA TCA

V   L   N   D   Y   L   V   *
1297         GTA TTG AAT GAC TAT CTT GTT TAA

SEQ ID No. 2:
GCTAGCCATGGCTTACTTTAACGACATCGCACCTATC

SEQ ID No. 3:
CTCGAGCCTAGGCTAAACAAGATAGTCATTCAATACTGATTTG

SEQ ID No. 4:
GCTAGCCATGGCCACTACCCCATTTGATGCTCCAGATAAG

SEQ ID No. 5:
CTCGAGCCTAGGCTAGTGTTTCAATTCACTTTCCATCTTGGCC

SEQ ID No. 6:
Artificial Thermoanaerobacter thermohydrosulfuricus xylose isomerase gene, with N-
terminal and C-terminal flanking regions. The coding region is based on the amino acid
sequence from GenBank Accession code D00756. The amino acid sequence encoded by
the coding nucleotide sequence is shown as SEQ ID No 15.
   1         GAATTCCTAGAAATAATTTTGTTTAACTTTAAGAAGGAGGAGCTAGCC M   E   Y   F   K   N   V   P   Q   I   K   Y   E   G   P   K
49           ATG GAA TAT TTC AAA AAC GTG CCA CAG ATC AAG TAT GAA GGT CCT AAA S   N   N   P   Y   A   F   K   F   Y   N   P   D   E   I   I
97           AGC AAT AAC CCT TAT GCA TTT AAG TTC TAT AAC CCA GAT GAA ATT ATA D   G   K   P   L   K   E   H   L   R   F   S   V   A   Y   W
145          GAT GGA AAA CCA TTA AAA GAA CAC TTA AGA TTT AGC GTA GCC TAC TGG H   T   F   T   A   N   G   T   D   P   F   G   A   P   T   M
193          CAT ACA TTT ACC GCT AAC GGA ACG GAT CCA TTT GGT GCA CCG ACT ATG Q   R   P   W   D   H   F   T   D   P   M   D   I   A   K   A
241          CAG CGT CCT TGG GAT CAT TTT ACC GAC CCT ATG GAC ATA GCA AAA GCA R   V   E   A   A   F   E   L   F   E   K   L   D   V   P   F
289          CGT GTG GAA GCC GCA TTC GAG CTT TTT GAA AAA TTG GAT GTT CCA TTC F   C   F   H   D   R   D   I   A   P   E   G   E   T   L   R
337          TTC TGT TTT CAT GAC AGA GAT ATA GCT CCG GAA GGT GAA ACA TTG AGA E   T   N   K   N   L   D   T   I   V   A   M   I   K   D   Y
385          GAA ACC AAC AAA AAC TTA GAT ACT ATC GTT GCT ATG ATT AAA GAC TAC L   K   T   S   K   T   K   V   L   W   G   T   A   N   L   F
433          TTA AAA ACG TCA AAG ACT AAA GTT CTT TGG GGC ACT GCT AAT TTG TTT S   N   P   R   F   V   H   G   A   A   T   S   C   N   A   D
481          TCT AAT CCA CGT TTC GTG CAT GGC GCT GCC ACA TCA TGT AAT GCA GAC
```

```
       V   F   A   Y   A   A   A   Q   V   K   K   A   L   E   I   T
529    GTA TTT GCT TAT GCA GCC GCT CAA GTT AAA AAG GCC TTA GAG ATT ACC

K   E   L   G   G   Q   N   Y   V   F   W   G   G   R   E   G
577    AAA GAG TTA GGA GGC CAG AAT TAT GTT TTC TGG GGT GGT CGT GAG GGA

Y   E   T   L   L   N   T   D   M   E   L   E   L   D   N   L
625    TAT GAG ACA CTT TTA AAT ACT GAT ATG GAG TTG GAA TTA GAT AAT TTA

A   R   F   L   H   M   A   V   E   Y   A   Q   E   I   G   F
673    GCA AGA TTC TTA CAC ATG GCA GTA GAA TAT GCT CAG GAA ATT GGT TTT

E   G   Q   F   L   I   E   P   K   P   K   E   P   T   K   H
721    GAA GGA CAG TTC TTG ATC GAG CCT AAA CCA AAG GAA CCA ACA AAG CAT

Q   Y   D   F   D   A   A   S   V   H   A   F   L   K   K   Y
769    CAG TAT GAT TTC GAC GCT GCT TCT GTA CAC GCC TTT TTG AAG AAG TAT

D   L   D   K   Y   F   K   L   N   I   E   A   N   H   A   T
817    GAT TTG GAT AAA TAC TTT AAG TTG AAC ATA GAG GCT AAT CAC GCA ACG

L   A   G   H   D   F   Q   H   E   L   R   Y   A   R   I   N
865    TTG GCA GGT CAC GAT TTT CAA CAC GAA TTG AGA TAC GCC CGT ATT AAT

N   M   L   G   S   I   D   A   N   M   G   D   M   L   L   G
913    AAC ATG TTA GGT TCC ATA GAT GCC AAC ATG GGT GAC ATG TTG CTG GGT

W   D   T   D   Q   Y   P   T   D   I   R   M   T   T   L   A
961    TGG GAT ACT GAT CAA TAC CCA ACG GAT ATT AGA ATG ACA ACT TTA GCA

M   Y   E   V   I   K   M   G   G   F   N   K   G   G   L   N
1009   ATG TAC GAG GTC ATT AAA ATG GGA GGT TTT AAC AAA GGA GGT TTG AAT

F   D   A   K   V   R   R   A   S   F   E   P   E   D   L   F
1057   TTC GAT GCT AAA GTG CGT CGT GCC TCT TTT GAA CCT GAA GAC CTT TTT

L   G   H   I   A   G   M   D   A   F   A   K   G   F   K   V
1105   CTT GGA CAT ATT GCC GGA ATG GAT GCA TTT GCA AAA GGT TTC AAG GTC

A   Y   K   L   V   K   D   G   V   F   D   R   F   I   E   E
1153   GCT TAT AAG CTT GTT AAG GAT GGT GTA TTT GAT AGA TTC ATT GAA GAG

R   Y   K   S   Y   R   E   G   I   G   A   E   I   V   S   G
1201   AGA TAC AAA TCC TAT CGT GAA GGT ATA GGT GCT GAA ATC GTT TCA GGT

K   A   N   F   K   T   L   E   E   Y   A   L   N   N   P   K
1249   AAG GCC AAT TTT AAG ACT TTA GAG GAA TAT GCA TTG AAT AAC CCA AAA

I   E   N   K   S   G   K   Q   E   L   L   E   S   I   L   N
1297   ATC GAA AAC AAA AGC GGT AAA CAG GAA CTG CTG GAA TCT ATT TTG AAT

Q   Y   L   F   S   E   *
1345   CAA TAT TTG TTC TCT GAA TAG CCTAGGCTCGAGGAATTC
```

SEQ ID No. 7:
Artificial *Thermoanaerobacter thermosulphurigenes* xylose isomerase gene, with N-terminal and C-terminal flanking regions. The coding region is based on amino acid sequence from GenBank Accession code J05650, except that the second amino acid has been changed from N into A, in order to enable the use of the "Kozak consensus sequence" for eucaryotic expression. *C. thermosulfurogenes* is an alternative name for *Thermoanaerobacter thermosulphurigenes* (Lee et al 1993). The amino acid sequence encoded by the coding region of this nucleotide sequence is shown as SEQ ID No 16.

```
   1   GAATTCCTAGAAATAATTTTGTTTAACTTTAAGAAGGAGGAGCTAGCC

M   A   K   Y   F   E   N   V   S   K   I   K   Y   E   G   P
  49   ATG GCC AAG TAT TTT GAG AAT GTT TCC AAG ATT AAG TAT GAA GGT CCT

K   S   N   N   P   Y   S   F   K   F   Y   N   P   E   E   V
  97   AAG TCA AAC AAC CCT TAC TCC TTC AAA TTC TAT AAT CCA GAA GAA GTT

I   D   G   K   T   M   E   E   H   L   R   F   S   I   A   Y
 145   ATA GAC GGT AAA ACG ATG GAG GAA CAC TTA AGA TTT TCT ATT GCT TAC

W   H   T   F   T   A   D   G   T   D   Q   F   G   K   A   T
 193   TGG CAC ACA TTT ACT GCC GAC GGC ACA GAC CAA TTC GGA AAG GCT ACT

M   Q   R   P   W   N   H   Y   T   D   P   M   D   I   A   K
 241   ATG CAA AGA CCG TGG AAC CAT TAC ACT GAT CCA ATG GAC ATA GCC AAA
```

-continued

```
         A   R   V   E   A   A   F   E   F   F   D   K   I   N   A   P
289     GCC AGA GTG GAG GCT GCA TTC GAG TTC TTC GAT AAG ATA AAC GCC CCT

Y   F   C   F   H   D   R   D   I   A   P   E   G   D   T   L
337     TAC TTC TGC TTC CAT GAT CGT GAC ATT GCT CCG GAA GGC GAT ACC TTG

R   E   T   N   K   N   L   D   T   I   V   A   M   I   K   D
385     AGA GAA ACC AAC AAA AAT CTT GAC ACC ATT GTC GCA ATG ATA AAA GAT

Y   L   K   T   S   K   T   K   V   L   W   G   T   A   N   L
433     TAT TTG AAG ACG TCT AAA ACC AAA GTT TTG TGG GGT ACG GCA AAC TTA

F   S   N   P   R   F   V   H   G   A   S   T   S   C   N   A
481     TTT TCT AAT CCG AGA TTT GTT CAT GGT GCT TCC ACA TCC TGC AAC GCA

D   V   F   A   Y   S   A   A   Q   V   K   K   A   L   E   I
529     GAT GTC TTT GCT TAT TCC GCT GCT CAA GTC AAA AAG GCT CTT GAG ATA

T   K   E   L   G   G   E   N   Y   V   F   W   G   G   R   E
577     ACC AAA GAA TTA GGT GGT GAA AAC TAC GTT TTC TGG GGT GGC AGA GAA

G   Y   E   T   L   L   N   T   D   M   E   F   E   L   D   N
625     GGT TAT GAG ACT CTT TTA AAT ACA GAT ATG GAA TTT GAA CTT GAC AAT

F   A   R   F   L   H   M   A   V   D   Y   A   K   E   I   G
673     TTC GCA AGA TTC TTG CAC ATG GCT GTC GAT TAT GCC AAG GAG ATA GGT

F   E   G   Q   F   L   I   E   P   K   P   K   E   P   T   K
721     TTT GAA GGC CAG TTC TTG ATT GAA CCG AAA CCA AAG GAA CCT ACC AAA

H   Q   Y   D   F   D   V   A   N   V   L   A   F   L   R   K
769     CAT CAG TAT GAC TTT GAT GTC GCA AAT GTT TTG GCT TTC TTG AGA AAA

Y   D   L   D   K   Y   F   K   V   N   I   E   A   N   H   A
817     TAC GAT TTA GAT AAG TAT TTC AAA GTA AAT ATT GAA GCT AAT CAT GCA

T   L   A   F   H   D   F   Q   H   E   L   R   Y   A   R   I
865     ACG TTG GCC TTC CAT GAT TTC CAG CAC GAG TTG AGA TAC GCT AGA ATC

N   G   V   L   G   S   I   D   A   N   T   G   D   M   L   L
913     AAT GGA GTC TTA GGA TCT ATC GAT GCT AAT ACC GGT GAT ATG CTG CTG

G   W   D   T   D   Q   F   P   T   D   I   R   M   T   T   L
961     GGA TGG GAT ACT GAT CAA TTT CCG ACC GAT ATT CGT ATG ACT ACC CTG

A   M   Y   E   V   I   K   M   G   G   F   D   K   G   G   L
1009    GCA ATG TAT GAA GTT ATT AAG ATG GGT GGA TTT GAT AAA GGC GGT CTG

N   F   D   A   K   V   R   R   A   S   F   E   P   E   D   L
1057    AAC TTC GAT GCA AAA GTA AGA AGA GCT TCT TTT GAA CCT GAA GAT TTG

F   L   G   H   I   A   G   M   D   A   F   A   K   G   F   K
1105    TTT TTA GGA CAC ATC GCT GGC ATG GAC GCA TTT GCT AAA GGT TTT AAG

V   A   Y   K   L   V   K   D   R   V   F   D   K   F   I   E
1153    GTA GCC TAT AAG CTT GTA AAA GAT AGA GTG TTC GAC AAA TTC ATC GAA

E   R   Y   A   S   Y   K   D   G   I   G   A   D   I   V   S
1201    GAG AGA TAT GCT TCT TAT AAG GAC GGA ATA GGA GCC GAT ATA GTT TCC

G   K   A   D   F   R   S   L   E   K   Y   A   L   E   R   S
1249    GGT AAG GCC GAT TTC AGA TCT CTT GAG AAA TAC GCC TTG GAA AGA TCA

Q   I   V   N   K   S   G   R   Q   E   L   L   E   S   I   L
1297    CAA ATC GTG AAC AAA TCA GGC CGT CAA GAA TTG TTA GAA TCA ATT CTT

N   Q   Y   L   F   A   E   *
1345    AAT CAA TAC CTG TTC GCT GAA TAG CCTAGGCTCGAGGAATTC
```

SEQ ID No. 8:
TAGCTAGCATGTCGTACTTCCCCACTGTCGAC

SEQ ID No. 9:
ATAAGCTTTCAGGTGTAGATAAAGCGGTTGACC

SEQ ID No. 10:
*Lactococcus lactis* subsp. *lactis*, strain KF147 xylose isomerase gene.
Based on GenBank accession number EU255918. The amino acid sequence
encoded by this nucleotide sequence is shown as SEQ ID No 11.

```
   1    atg gct tac ttt aac gac atc gca cct atc aaa tac gaa ggt aca aaa 49    act aaa aat atg ttt gcc ttt cgt cat tat aat cca gaa gaa gta gtt
```

-continued

```
  97   gct ggt aaa aca atg gaa gaa caa ctt cat ttt gcc ctt gca ttt tgg 145   cat aca att acg atg gat ggg tca gat ccc ttt ggg gga gca aca atg 193   gaa cgt cct tgg gat ttg gaa ggt ggt tct gaa ctt gac cgt gct cac 241   cgt cga gta gat gct ttc ttt gaa att gct gaa aaa tta ggt gtt aaa 289   tat tat tgt ttc cat gat att gat att gca cct act gga aat tct ttg 337   aaa gaa ttt tat gct aat ttg gac gaa att act gac cac ctt ctt gaa 385   aaa caa aaa gca aca ggc att aaa tta ctt tgg aat aca gca aac atg 433   ttt tca aat ccc cgc tat atg aat ggt gtt tca act tct aat cgt gct 481   gaa gtc ttt gct tat ggt gct gca caa gtt aaa aaa ggt ctt gaa ctt 529   tct aaa aaa ctc ggt ggt gaa aat tat gtc ttc tgg ggt ggt cgt gaa 577   ggt tat gaa tca ctt ttg aat aca gat atg ggt ctt gaa atg gat cat 625   atg gca aaa ttc ttc cat ttg gca att gat tat gca aaa tca atc aac 673   cac ttg cct att ttc ttg att gaa cca aaa cca aaa gaa cca atg act 721   cac caa tat gat ttt gac tca gca aca gct ctt gct ttc ttg caa aaa 769   tat gac ttg gac aaa tac ttc aaa ctc aat ctt gaa aca aat cat gct 817   tgg ttg gct ggg cac act ttt gaa cac gaa tta aat act gca cgt act 865   ttc aat gct ttg ggt tct att gat gcc aat caa gga aat tac ttg ctt 913   ggt tgg gat aca gat gaa ttc cca aca ctt gtt att gat atc aca ctt 961   gcg atg cac caa att ctt ttg aac ggt gga ctt ggc aaa ggt gga att 1009   aac ttt gat gcg aaa gta cgt cgt aca agt ttc aaa gca gaa gat tta 1057   att ctt gct cat att gca ggg atg gat act tat gcg cgt gct ttg aaa 1105   ggt gca gca gca atc att gaa gat aaa ttc ttg tct gat att gtt gac 1153   gaa cgt tat agt tca tac aaa aat aca gaa gtt ggt caa tcc att gaa 1201   aat gga aca gca act ttt gaa agt ctt gct gca ttt gca ctt gaa cat 1249   ggt gac gat att gaa ctt gat tct aat cac ttg gaa tac atc aaa tca 1297   gta ttg aat gac tat ctt gtt taa
```

SEQ ID No. 11:
*Lactococcus lactis* subsp. *lactis* Strain KF147 xylose isomerase gene.
Based on GenBank accession number ABX75758.
The amino acid sequence encoded by the nucleotide sequence of SEQ ID No 10.

MAYFNDIAPIKYEGTKTKNMFAFRHYNPEEVVAGKTMEEQLHFALAFWHTITMDGSDPFG

GATMERPWDLEGGSELDRAHRRVDAFFEIAEKLGVKYYCFHDIDIAPTGNSLKEFYANLD

EITDHLLEKQKATGIKLLWNTANMFSNPRYMNGVSTSNRAEVFAYGAAQVKKGLELSKKL

GGENYVFWGGREGYESLLNTDMGLEMDHMAKFFHLAIDYAKSINHLPIFLIEPKPKEPMT

HQYDFDSATALAFLQKYDLDKYFKLNLETNHAWLAGHTFEHELNTARTFNALGSIDANQG

NYLLGWDTDEFPTLVIDITLAMHQILLNGGLGKGGINFDAKVRRTSFKAEDLILAHIAGM

DTYARALKGAAAIIEDKFLSDIVDERYSSYKNTEVGQSIENGTATFESLAAFALEHGDDI

ELDSNHLEYIKSVLNDYLV

SEQ ID No 12:
*Lactococcus lactis* subsp. *lactis*, strain IO-1 xylose isomerase gene. Based on GenBank accession number AF092041. The amino acid sequence encoded by this nucleotide sequence is shown as SEQ ID No 13.

```
   1   atg gct tac ttt aac gac atc gca cct atc aaa tac gaa ggt aca aaa 49   act aaa aat atg ttt gcc ttt cgc cat tat aat cca gaa gaa gta gtt
```

```
 97  gct ggt aaa aca atg gaa gaa caa ctt cat ttt gcc ctt gca ttt tgg
145  cat aca att aca atg gat ggg tca gac ccc ttt ggg gga gca aca atg
193  gaa cgt cct tgg gat ttg gaa ggt ggt tct gaa ctt gac cgt gct cac
241  cgt cga gta gat gct ttc ttt gaa att gct gaa aaa tta ggt gtt aaa
289  tat tat tgt ttc cat gat att gat att gca cct act gga aat tct ttg
337  aaa gaa ttt tat gct aat ttg gac gaa att act gac cac ctt ctt gaa
385  aaa caa aaa gca aca ggg att aaa tta ctt tgg aat aca gca aac atg
433  ttt tca aat ccc cgc tat atg aat ggt gtt tca act tct aac cgt gct
481  gaa gtc ttt gct tat ggt gct gca caa gtt aaa aaa ggt ctt gaa ctt
529  tct aaa aaa ctc ggt ggt gaa aat tac gtc ttc tgg ggt ggt cgt gaa
577  ggt tat gaa tca ctt ttg aat aca gat atg ggt ctt gaa atg gat cat
625  atg gca aaa ttc ttc cat ttg gca att gat tat gca aaa tca atc aac
673  cac ttg ccc att ttc ttg atc gaa cca aaa cca aaa gaa cca atg act
721  cac caa tat gat ttt gac tca gca aca gct ctt gct ttc ttg caa aaa
769  tat gat ttg gac aaa tat ttc aaa ctc aat ctt gaa aca aat cat gct
817  tgg ttg gct gga cac act ttt gaa cac gaa tta aat act gct cgt act
865  ttc aat gct ttg ggt tct att gat gcc aat caa gga aat tac ttg ctt
913  ggt tgg gat aca gat gaa ttc cca aca ctt gtt att gat atc aca ctt
961  gcg atg cac caa att ctt ttg aac ggt gga ctt ggc aaa ggt gga att
1009 aac ttt gat gcg aaa gta cgt cgt aca agt ttc aaa gca gaa gat tta
1057 att ctt gct cat att gca ggg atg gat act tat gcg cgt gct ttg aaa
1105 ggt gca gca gca atc att gaa gat aaa ttc ttg tct gat att gtt gac
1153 gaa cgt tat agt tca tac aaa aat aca gaa gtt gga caa tcc att gaa
1201 aat gga aca gca act ttt aaa agt ctt gcc gca ttt gca ctt gaa cat
1249 ggt gac gat att gaa ctt gat tct aat cac ttg gaa tac atc aaa tca
1297 gta ttg aat gac tat ctt gtt taa
```

SEQ ID No 13:
Lactococcus lactis subsp. lactis, Strain IO-1 xylose isomerase. Based on GenBank
accession number AAD20249. The amino acid sequence encoded by the nucleotide
sequence of SEQ ID No 12. The amino acids which differ to SEQ ID No 18 are
underlined.
MAYFNDIAPIKYEGTKTKNMFAFRHYNPEEVVAGKTMEEQLHFALAFWHTITMDGSDPFG

GATMERPWDLEGGSELDRAHRRVDAFFEIAEKLGVKYYCFHDIDIAPTGNSLKEFYANLD

EITDHLLEKQKATGIKLLWNTANMFSNPRYMNGVSTSNRAEVFAYGAAQVKKGLELSKKL

GGENYVFWGGREGYESLLNTDMGLEMDHMAKFFHLAIDYAKSINHLPIFLIEPKPKEPMT

HQYDFDSATALAFLQKYDLDKYFKLNLETNHAWLAGHTFEHELNTARTFNALGSIDANQG

NYLLGWDTDEFPTLVIDITLAMHQILLNGGLGKGGINFDAKVRRTSFKAEDLILAHIAGM

DTYARALKGAAAIIEDKFLSDIVDERYSSY<u>K</u>NTEVGQSIENGTATF<u>K</u>SLAAFALE<u>H</u>GDDI

ELDSNHLEYIKSVLNDYLV

SEQ ID No 14:
The amino acid sequence encoded by the nucleotide sequence of SEQ ID No 1. The amino
acid which differs to SEQ ID No 18 is underlined.
M A Y F N D I A P I K Y E G T K

T K N M F A F R H Y N P E E V V

AGKTMEEQLHFALAFW

HTITMDGSDPFGGATM

ERPWDLEGGSELDRAH

RRVDAFFEIAEKLGVK

YYCFHDIDIAPTGNSL

KEFYANLDEITDHLLE

KQKATGIKLLWNTANM

FSNPRYMNGVSTSNRA

EVFAYGAAQVKKGLEL

SKKLGGENYVFWGGRE

GYESLLNTDMGLEMDH

MAKFFHLAIDYAKSIN

HLPIFLIEPKPKEPMT

HQYDFDSATALAFLQK

YDLDKYFKLNLETNHA

WLAGHTFEHELNTART

FNALGSIDANQGNYLL

GWDTDEFPTLVIDITL

AMHQILLNGGLGKGGI

NFDAKVRRTSFKAEDL

ILAHIAGMDTYARALK

GAAAIIEDKFLSDIVD

ERYSSY<u>K</u>NTEVGQSIE

NGTATFESLAAFALEY

GDDIELDSNHLEYIKS

VLNDYLV

SEQ ID No 15:
GenBank accession number BAA00652. The amino acid sequence encoded by
the coding region of nucleotide sequence of SEQ ID No 6.
MEYFKNVPQIKYEGPK

SNNPYAFKFYNPDEII

DGKPLKEHLRFSVAYW

HTFTANGTDPFGAPTM

QRPWDHFTDPMDIAKA

RVEAAFELFEKLDVPF

FCFHDRDIAPEGETLR

ETNKNLDTIVAMIKDY

LKTSKTKVLWGTANLF

SNPRFVHGAATSCNAD

VFAYAAAQVKKALEIT

KELGGQNYVFWGGREG

YETLLNTDMELELDNL

ARFLHMAVEYAQEIGF

EGQFLIEPKPKEPTKH

QYDFDAASVHAFLKKY

DLDKYFKLNIEANHAT

LAGHDFQHELRYARIN

NMLGSIDANMGDMLLG

WDTDQYPTDIRMTTLA

MYEVIKMGGFNKGGLN

FDAKVRRASFEPEDLF

LGHIAGMDAFAKGFKV

AYKLVKDGVFDRFIEE

RYKSYREGIGAEIVSG

KANFKTLEEYALNNPK

IENKSGKQELLESILN

QYLFSE

SEQ ID No 16:
GenBank accession number AAA23285. The amino acid sequence encoded by
the coding region of nucleotide sequence of SEQ ID No 7.
MAKYFENVSKIKYEGP

KSNNPYSFKFYNPEEV

IDGKTMEEHLRFSIAY

WHTFTADGTDQFGKAT

MQRPWNHYTDPMDIAK

ARVEAAFEFFDKINAP

YFCFHDRDIAPEGDTL

RETNKNLDTIVAMIKD

YLKTSKTKVLWGTANL

FSNPRFVHGASTSCNA

DVFAYSAAQVKKALEI

TKELGGENYVFWGGRE

GYETLLNTDMEFELDN

FARFLHMAVDYAKEIG

FEGQFLIEPKPKEPTK

HQYDFDVANVLAFLRK

YDLDKYFKVNIEANHA

TLAFHDFQHELRYARI

NGVLGSIDANTGDMLL

GWDTDQFPTDIRMTTL

AMYEVIKMGGFDKGGL

NFDAKVRRASFEPEDL

FLGHIAGMDAFAKGFK

VAYKLVKDRVFDKFIE

E R Y A S Y K D G I G A D I V S

G K A D F R S L E K Y A L E R S

Q I V N K S G R Q E L L E S I L

N Q Y L F A E

SEQ ID No 17:
Coding region of Xylose isomerase gene cloned by PCR out of *Lactococcus lactis* strain
designated DSM 20175, using primers shown in SEQ ID No 2 and SEQ ID No 3.

```
   1  atg gct tac ttt aac gac atc gca cct atc aaa tac gaa ggt aca aaa 49  act aaa aat atg ttt gcc ttt cgc cat tat aat cca gaa gaa gta gtt 97  gct ggt aaa aca atg gaa gaa caa ctt cat ttt gcc ctt gca ttt tgg 145  cat aca att aca atg gat ggg tca gat ccc ttt ggg gga gca aca atg 193  gaa cgc cct tgg gat ttg gaa ggt ggt tct gaa ctt gac cgt gct cac 241  cgt cga gta gat gct ttc ttt gaa att gct gaa aaa tta ggt gtt aaa 289  tat tat tgt ttc cat gat att gat att gca cct act gga aat tct ttg 337  aaa gaa ttt tat gct aat ttg gac gaa att act gac cac ctt ctt gaa 385  aaa caa aaa gca aca gga att aaa tta ctt tgg aat aca gca aac atg 433  ttt tca aat ccc cgc tat atg aat ggt gtt tca act tct aat cgt gct 481  gaa gtc ttt gct tat ggt gct gca caa gtt aaa aaa ggt ctt gaa ctt 529  tct aaa aaa ctc ggt ggt gaa aat tac gtc ttc tgg ggt ggt cgt gaa 577  ggt tat gaa tca ctt ttg aat aca gat atg ggt ctt gaa atg gat cat 625  atg gca aaa ttc ttc cat ttg gca att gat tat gca aaa tca atc aac 673  cac ttg ccc att ttc ttg att gaa cca aaa cca aaa gaa cca atg act 721  cac caa tat gat ttt gac tca gca aca gct ctt gct ttc ttg caa aaa 769  tat gat ttg gac aaa tat ttc aaa ctc aat ctt gaa aca aat cat gct 817  tgg ttg gct gga cac act ttt gaa cac gaa tta aat act gct cgt act 865  ttc aat gct ttg ggt tct att gat gcc aat caa gga aat tac ttg ctt 913  ggt tgg gat aca gat gaa ttc cca aca ctt gtt att gat atc aca ctt 961  gcg atg cac caa att ctt ttg aac ggt gga ctt ggc aaa ggt gga att 1009  aac ttt gat gcg aaa gta cgt cgt aca agt ttc aaa gca gaa gat tta 1057  att ctt gct cat att gca ggg atg gat act tat gcg cgt gct ttg aaa 1105  ggt gca gca gca atc att gaa gat aaa ttc ttg tct gat att gtt gac 1153  gaa cgt tat agt tca tac aga aat aca gaa gtt ggt caa tcc att gaa 1201  aat gga aca gca act ttt gaa agt ctt gcc gca ttt gca ctt gaa tat 1249  ggt gat gat att gaa ctt gat tct aat cac ttg gaa tac atc aaa tca 1297  gta ttg aat gac tat ctt gtt taa
```

SEQ ID No 18:
Amino acid sequence encoded by SEQ ID 17.
MAYFNDIAPIKYEGTKTKNMFAFRHYNPEEVVAGKTMEEQLHFALAFWHTITMD

GSDPFGGATMERPWDLEGGSELDRAHRRVDAFFEIAEKLGVKYYCFHDIDIAPTG

NSLKEFYANLDEITDHLLEKQKATGIKLLWNTANMFSNPRYMNGVSTSNRAEVFA

YGAAQVKKGLELSKKLGGENYVFWGGREGYESLLNTDMGLEMDHMAKFFHLAI

DYAKSINHLPIFLIEPKPKEPMTHQYDFDSATALAFLQKYDLDKYFKLNLETNHAW

LAGHTFEHELNTARTFNALGSIDANQGNYLLGWDTDEFPTLVIDITLAMHQILLNG

GLGKGGINFDAKVRRTSFKAEDLILAHIAGMDTYARALKGAAAIIEDKFLSDIVDE

RYSSYRNTEVGQSIENGTATFESLAAFALEYGDDIELDSNHLEYIKSVLNDYLV

SEQ ID No 19:
Artificial variant of Lactococcus xylose isomerase, amino acid sequence (SEQ ID No 18).
The amino acids which differ to SEQ ID No 18 are underlined. The nucleotide sequence
encoding this amino acid sequence is shown as SEQ ID No. 27
MAYFNDIAPIKYEGTKTKNMFAFRHYNPEEVVAGKTMEEQLHFALAFWHTITMDGSDPFG

GATMERPWDLEGGSELDRAHRRVDAFFEIAEKLGVKYYCFHDIDIAPTGNSLKEFYANLD

EITDHLLEKQKATGIKLLWNTANMFSNPRYMNGVSTSNRAEVFAYGAAQVKKGLELSKKL

GGENYVFWGGREGYESLLNTDMGLEMDHMAKFFHLAIDYAKSINHLPIFLIEPKPKEPMT

HQYDFDSATALAFLQKYDLDKYFKLNLETNHAWLAGHTFEHELNTARTFNALGSIDANQG

NYLLGWDTEFFTLVIDITLAMHQILLNGGLGKGGINFDAKVRRTSFKAEDLILAHIAGM

DTYARALKGAAAIIEDKFLSDIVDERYSSYRNTEVGQSIENGTATFKSLAAFALEHGDDI

ELDSNHLEYIKSVLNDYLV

SEQ ID No 20:
Artificial variant of Lactococcus xylose isomerase, amino acid sequence (SEQ ID No 18).
The amino acid which differs to SEQ ID No 18 is underlined. The nucleotide sequence
encoding this amino acid sequence is shown as SEQ ID No. 28
MAYFNDIAPIKYEGTKTKNMFAFRHYNPEEVVAGKTMEEQLHFALAFWHTITMDGSDPFG

GATMERPWDLEGGSELDRAHRRVDAFFEIAEKLGVKYYCFHDIDIAPTGNSLKEFYANLD

EITDHLLEKQKATGIKLLWNTANMFSNPRYMNGVSTSNRAEVFAYGAAQVKKGLELSKKL

GGENYVFWGGREGYESLLNTDMGLEMDHMAKFFHLAIDYAKSINHLPIFLIEPKPKEPMT

HQYDFDSATALAFLQKYDLDKYFKLNLETNHAWLAGHTFEHELNTARTFNALGSIDANQG

NYLLGWDTEFFTLVIDITLAMHQILLNGGLGKGGINFDAKVRRTSFKAEDLILAHIAGM

DTYARALKGAAAIIEDKFLSDIVDERYSSYRNTEVGQSIENGTATFKSLAAFALEYGDDI

ELDSNHLEYIKSVLNDYLV

SEQ ID No 21:
R391K Sense primer:
GTTGACGAACGATATAGTTCATACAAAAATACAGAAGTTGG

SEQ ID No 22:
R391K antisense primer:
CCAACTTCTGTATTTTTGTATGAACTATATCGTTCGTCAAC

SEQ ID No 23:
E407K sense primer:
ACAGCAACTTTTAAAAGCTTAGCCGCATTTGCACTTGAATATGGTGATGATATTG SEQ ID No 24:
E407K antisense primer:
CAATATCATCACCATATTCAAGTGCAAATGCGGCTAAGCTTTTAAAAGTTGCTGT SEQ ID No 25:
E407K-Y416H sense primer:
ACAGCAACTTTTAAAAGCTTAGCCGCATTTGCACTTGAACATGGTGATGATATTG SEQ ID No 26:
E407K-Y416H antisense primer:
CAATATCATCACCATGTTCAAGTGCAAATGCGGCTAAGCTTTTAAAAGTTGCTGT SEQ ID No 27:
The nucleotide sequence encoding the amino acid sequence shown as SEQ ID No. 19
  1   atg gct tac ttt aac gac atc gca cct atc aaa tac gaa ggt aca aaa 49   act aaa aat atg ttt gcc ttt cgc cat tat aat cca gaa gaa gta gtt 97   gct ggt aaa aca atg gaa gaa caa ctt cat ttt gcc ctt gca ttt tgg 145   cat aca att aca atg gat ggg tca gat ccc ttt ggg gga gca aca atg 193   gaa cgc cct tgg gat ttg gaa ggt ggt tct gaa ctt gac cgt gct cac 241   cgt cga gta gat gct ttc ttt gaa att gct gaa aaa tta ggt gtt aaa -continued

```
 289  tat tat tgt ttc cat gat att gat att gca cct act gga aat tct ttg
 337  aaa gaa ttt tat gct aat ttg gac gaa att act gac cac ctt ctt gaa
 385  aaa caa aaa gca aca ggg att aaa tta ctt tgg aat aca gca aac atg
 433  ttt tca aat ccc cgc tat atg aat ggt gtt tca act tct aat cgt gct
 481  gaa gtc ttt gct tat ggt gct gca caa gtt aaa aaa ggt ctt gaa ctt
 529  tct aaa aaa ctc ggt ggt gaa aat tac gtc ttc tgg ggt ggt cgt gaa
 577  ggt tat gaa tca ctt ttg aat aca gat atg ggt ctt gaa atg gat cat
 625  atg gca aaa ttc ttc cat ttg gca att gat tat gca aaa tca atc aac
 673  cac ttg ccc att ttc ttg att gaa cca aaa cca aaa gaa cca atg act
 721  cac caa tat gat ttt gac tca gca aca gct ctt gct ttc ttg caa aaa
 769  tat gat ttg gac aaa tat ttc aaa ctc aat ctt gaa aca aat cat gct
 817  tgg ttg gct gga cac act ttt gaa cac gaa tta aat act gct cgt act
 865  ttc aat gct ttg ggt tct att gat gcc aat caa gga aat tac ttg ctt
 913  ggt tgg gat aca gat gaa ttc cca aca ctt gtt att gat atc aca ctt
 961  gcg atg cac caa att ctt ttg aac ggt gga ctt ggc aaa ggt gga att
1009  aac ttt gat gcg aaa gta cgt cgt aca agt ttc aaa gca gaa gat tta
1057  att ctt gct cat att gca ggg atg gat act tat gcg cgt gct ttg aaa
1105  ggt gca gca gca atc att gaa gat aaa ttc ttg tct gat att gtt gac
1153  gaa cgt tat agt tca tac aga aat aca gaa gtt ggt caa tcc att gaa
1201  aat gga aca gca act ttt aaa agc tta gcc gca ttt gca ctt gaa cat
1249  ggt gat gat att gaa ctt gat tct aat cac ttg gaa tac atc aaa tca
1297  gta ttg aat gac tat ctt gtt taa
```

SEQ ID No 28:
The nucleotide sequence encoding the amino acid sequence shown as SEQ ID No. 20

```
   1  atg gct tac ttt aac gac atc gca cct atc aaa tac gaa ggt aca aaa
  49  act aaa aat atg ttt gcc ttt cgc cat tat aat cca gaa gaa gta gtt
  97  gct ggt aaa aca atg gaa gaa caa ctt cat ttt gcc ctt gca ttt tgg
 145  cat aca att aca atg gat ggg tca gat ccc ttt ggg gga gca aca atg
 193  gaa cgc cct tgg gat ttg gaa ggt ggt tct gaa ctt gac cgt gct cac
 241  cgt cga gta gat gct ttc ttt gaa att gct gaa aaa tta ggt gtt aaa
 289  tat tat tgt ttc cat gat att gat att gca cct act gga aat tct ttg
 337  aaa gaa ttt tat gct aat ttg gac gaa att act gac cac ctt ctt gaa
 385  aaa caa aaa gca aca ggg att aaa tta ctt tgg aat aca gca aac atg
 433  ttt tca aat ccc cgc tat atg aat ggt gtt tca act tct aat cgt gct
 481  gaa gtc ttt gct tat ggt gct gca caa gtt aaa aaa ggt ctt gaa ctt
 529  tct aaa aaa ctc ggt ggt gaa aat tac gtc ttc tgg ggt ggt cgt gaa
 577  ggt tat gaa tca ctt ttg aat aca gat atg ggt ctt gaa atg gat cat
 625  atg gca aaa ttc ttc cat ttg gca att gat tat gca aaa tca atc aac
 673  cac ttg ccc att ttc ttg att gaa cca aaa cca aaa gaa cca atg act
 721  cac caa tat gat ttt gac tca gca aca gct ctt gct ttc ttg caa aaa
 769  tat gat ttg gac aaa tat ttc aaa ctc aat ctt gaa aca aat cat gct
```

```
 817  tgg ttg gct gga cac act ttt gaa cac gaa tta aat act gct cgt act 865  ttc aat gct ttg ggt tct att gat gcc aat caa gga aat tac ttg ctt 913  ggt tgg gat aca gat gaa ttc cca aca ctt gtt att gat atc aca ctt 961  gcg atg cac caa att ctt ttg aac ggt gga ctt ggc aaa ggt gga att 1009  aac ttt gat gcg aaa gta cgt cgt aca agt ttc aaa gca gaa gat tta 1057  att ctt gct cat att gca ggg atg gat act tat gcg cgt gct ttg aaa 1105  ggt gca gca gca atc att gaa gat aaa ttc ttg tct gat att gtt gac 1153  gaa cgt tat agt tca tac aga aat aca gaa gtt ggt caa tcc att gaa 1201  aat gga aca gca act ttt aaa agc tta gcc gca ttt gca ctt gaa tat 1249  ggt gat gat att gaa ctt gat tct aat cac ttg gaa tac atc aaa tca 1297  gta ttg aat gac tat ctt gtt taa
```

---

The invention claimed is:

1. A transformed microorganism capable of:

xylose isomerase activity of at least xylose isomerase units per mg microorganism protein;

wherein said microorganism has been transformed with a nucleotide sequence encoding the amino acid sequence of an exogenous lactococcal xylose isomerase shown as SEQ ID No 18, or a nucleotide sequence encoding an amino acid sequence having at least 95% identity to the amino acid sequence of SEQ ID No 18;

and wherein said transformed microorganism is a transformed yeast wherein said transformed yeast is *Saccharomyces*.

2. The microorganism according to claim 1 wherein said microorganism has been transformed with the nucleotide sequence shown as SEQ ID No 17 or a nucleotide sequence having at least 95% identity to the nucleotide sequence shown as SEQ ID No 17.

3. A culture medium comprising a microorganism according to claim 1.

4. The culture medium according to claim 3 wherein said culture medium comprises a source of xylose.

5. The culture medium according to claim 3 wherein said culture medium comprises material derived from lignocelluosic material.

6. A method for preparing a transformed microorganism, said method comprising the step of transforming a microorganism such that said transformed microorganism is capable of:

xylose isomerase activity of at least xylose isomerase units per mg microorganism protein;

wherein said microorganism has been transformed with a nucleotide sequence encoding an exogenous lactococcal xylose isomerase shown as SEQ ID No 18, or a nucleotide sequence encoding an amino acid sequence having at least 95% identity to the amino acid sequence of SEQ ID No 18;

and wherein said transformed microorganism is a transformed yeast wherein said transformed yeast is *Saccharomyces*.

7. The method according to claim 6 wherein said nucleotide sequence encoding an exogenous lactococcal xylose isomerase comprises the nucleotide sequence shown as SEQ ID No 17, or nucleotide sequence having at least 95% identity to the nucleotide sequence shown as SEQ ID No 17.

8. The method according to claim 6 wherein said nucleotide sequence encoding an exogenous lactococcal xylose isomerase is in an expression vector encoding same.

* * * * *

UNITED STATES PATENT AND TRADEMARK OFFICE
CERTIFICATE OF CORRECTION

PATENT NO. : 9,523,095 B2
APPLICATION NO. : 14/078603
DATED : December 20, 2016
INVENTOR(S) : Birgitte Rönnow et al.

Page 1 of 1

It is certified that error appears in the above-identified patent and that said Letters Patent is hereby corrected as shown below:

In the Claims

In Column 105, Claim 1, Line 54:
INSERT --0.7-- after least and before xylose

In Column 106, Claim 6, Line 66:
INSERT --0.7-- after least and before xylose

Signed and Sealed this
Fourth Day of July, 2017

Joseph Matal
*Performing the Functions and Duties of the*
*Under Secretary of Commerce for Intellectual Property and*
*Director of the United States Patent and Trademark Office*